(12) United States Patent
Anderson et al.

(10) Patent No.: US 11,089,775 B2
(45) Date of Patent: *Aug. 17, 2021

(54) SYSTEM FOR HYPOTHERMIC TRANSPORT OF SAMPLES

(71) Applicant: Paragonix Technologies, Inc., Braintree, MA (US)

(72) Inventors: Lisa Maria Anderson, Boston, MA (US); Jared Alden Judson, Medford, MA (US)

(73) Assignee: Paragonix Technologies, Inc., Braintree, MA (US)

( * ) Notice: Subject to any disclaimer, the term of this patent is extended or adjusted under 35 U.S.C. 154(b) by 138 days.

This patent is subject to a terminal disclaimer.

(21) Appl. No.: 15/870,209

(22) Filed: Jan. 12, 2018

(65) Prior Publication Data

US 2018/0132478 A1 May 17, 2018

Related U.S. Application Data

(63) Continuation of application No. 14/378,034, filed as application No. PCT/US2013/054353 on Aug. 9, 2013, now Pat. No. 9,867,368, which is a continuation of application No. 13/572,315, filed on Aug. 10, 2012, now Pat. No. 8,828,710, which is a continuation-in-part of application No. 13/420,962, filed on Mar. 15, 2012, now Pat. No. 8,835,158.

(Continued)

(51) Int. Cl.
*A01N 1/00* (2006.01)
*C12M 3/00* (2006.01)
(Continued)

(52) U.S. Cl.
CPC ............ *A01N 1/0226* (2013.01); *A01N 1/00* (2013.01); *A01N 1/02* (2013.01); *A01N 1/0236* (2013.01);
(Continued)

(58) Field of Classification Search
CPC ...... C12M 21/08; A01N 1/0236; A01N 1/0242
See application file for complete search history.

(56) References Cited

U.S. PATENT DOCUMENTS 3,398,743 A 8/1968 Shalit
3,607,646 A 9/1971 de Roissart
(Continued)

FOREIGN PATENT DOCUMENTS

CA 2722615 A1 10/2009
CH 551741 A 7/1974
(Continued)

OTHER PUBLICATIONS

Bunegin, et al., Interstitial pO2 and High Energy Phosphates in the Canine Heart during Hypothermic Preservation in a New, Portable, Pulsatile Perfusion Device, from the Department of Anesthesiology University of Texas Health Science Center at San Antonio, Texas; and Center for Cardiovascular Surgery of the Republic of Lithuania, Vilnius, Lithuania, vol. 3, No. 3, Oct. 1998, pp. 1-6.
(Continued)

*Primary Examiner* — Nathan A Bowers
(74) *Attorney, Agent, or Firm* — Brown Rudnick LLP

(57) ABSTRACT

A system for the hypothermic transport of biological samples, such as tissues, organs, or body fluids. The system includes a self-purging preservation apparatus to suspend a sample in preservation fluid and perfuse a tissue with preservation fluid. The self-purging preservation apparatus is placed in an insulated transport container having a cooling medium. When assembled, the system allows for transport of biological samples for extended periods of time at a stable temperature.

13 Claims, 40 Drawing Sheets

Related U.S. Application Data

(60) Provisional application No. 61/541,425, filed on Sep. 30, 2011, provisional application No. 61/452,917, filed on Mar. 15, 2011.

(51) Int. Cl.
*A01N 1/02* (2006.01)
*C12M 1/00* (2006.01)

(52) U.S. Cl.
CPC ......... *A01N 1/0247* (2013.01); *A01N 1/0284* (2013.01); *C12M 21/08* (2013.01); *C12M 45/22* (2013.01)

(56) References Cited

U.S. PATENT DOCUMENTS

| | | | |
|---|---|---|---|
| 3,935,065 A | 1/1976 | Doerig | |
| 4,336,248 A | 6/1982 | Bonhard et al. | |
| 4,575,498 A | 3/1986 | Holmes et al. | |
| 4,643,713 A * | 2/1987 | Viitala | A61M 1/3627 128/DIG. 3 |
| 4,952,409 A | 8/1990 | Bando et al. | |
| 4,976,708 A * | 12/1990 | Oshiyama | A61M 1/3627 604/408 |
| 5,066,578 A | 11/1991 | Wikman-Coffelt | |
| 5,141,847 A | 8/1992 | Sugimachi et al. | |
| 5,149,321 A | 9/1992 | Klatz et al. | |
| 5,186,431 A | 2/1993 | Tamari | |
| 5,234,405 A | 8/1993 | Klatz et al. | |
| RE34,387 E | 9/1993 | Holmes et al. | |
| 5,252,537 A | 10/1993 | De Winter-Scailteur | |
| 5,306,711 A | 4/1994 | Andrews | |
| 5,320,846 A | 6/1994 | Bistrian et al. | |
| 5,326,706 A | 7/1994 | Yland et al. | |
| 5,356,771 A | 10/1994 | O'Dell | |
| 5,362,622 A | 11/1994 | O'Dell et al. | |
| 5,385,821 A | 1/1995 | O'Dell et al. | |
| 5,395,314 A | 3/1995 | Klatz et al. | |
| 5,434,045 A | 7/1995 | Jost | |
| 5,584,804 A | 12/1996 | Klatz et al. | |
| 5,586,438 A | 12/1996 | Fahy | |
| 5,599,659 A | 2/1997 | Brasile et al. | |
| 5,601,972 A | 2/1997 | Meryman | |
| 5,629,145 A | 5/1997 | Meryman | |
| 5,643,712 A | 7/1997 | Brasile | |
| 5,656,154 A | 8/1997 | Meryman | |
| 5,696,152 A | 12/1997 | Southard | |
| 5,699,793 A | 12/1997 | Brasile | |
| 5,702,881 A | 12/1997 | Brasile et al. | |
| 5,707,971 A | 1/1998 | Fahy | |
| 5,709,654 A | 1/1998 | Klatz et al. | |
| 5,712,084 A | 1/1998 | Osgood | |
| 5,716,378 A | 2/1998 | Minten | |
| 5,752,929 A | 5/1998 | Klatz et al. | |
| 5,827,222 A | 10/1998 | Klatz et al. | |
| 5,843,024 A | 12/1998 | Brasile | |
| 5,916,800 A | 6/1999 | Elizondo et al. | |
| 5,922,598 A | 7/1999 | Mintchev | |
| 5,963,335 A | 10/1999 | Boutelle | |
| 5,965,433 A | 10/1999 | Gardetto et al. | |
| 6,014,864 A | 1/2000 | Owen | |
| 6,020,575 A | 2/2000 | Nagle et al. | |
| 6,024,698 A | 2/2000 | Brasile | |
| 6,046,046 A | 4/2000 | Hassanein | |
| 6,060,232 A | 5/2000 | Von Baeyer et al. | |
| 6,100,082 A | 8/2000 | Hassanein | |
| 6,174,719 B1 | 1/2001 | Elizondo et al. | |
| 6,194,137 B1 | 2/2001 | Khirabadi et al. | |
| 6,209,343 B1 | 4/2001 | Owen | |
| 6,241,945 B1 | 6/2001 | Owen | |
| 6,280,925 B1 | 8/2001 | Brockbank | |
| 6,303,388 B1 | 10/2001 | Fahy | |
| D453,828 S | 2/2002 | Brassil et al. | |
| 6,375,613 B1 | 4/2002 | Brasile | |
| 6,406,839 B1 | 6/2002 | Segall et al. | |
| 6,413,713 B1 | 7/2002 | Serebrennikov | |
| 6,475,716 B1 | 11/2002 | Seki | |
| 6,485,450 B1 | 11/2002 | Owen | |
| 6,492,103 B1 | 12/2002 | Taylor | |
| D468,436 S | 1/2003 | Brassil et al. | |
| D470,594 S | 2/2003 | Brassil et al. | |
| 6,569,615 B1 | 5/2003 | Thatte et al. | |
| 6,582,953 B2 | 6/2003 | Brasile | |
| 6,596,531 B2 | 7/2003 | Campbell et al. | |
| 6,642,019 B1 | 11/2003 | Anderson et al. | |
| 6,642,045 B1 | 11/2003 | Brasile | |
| 6,656,380 B2 | 12/2003 | Wood et al. | |
| 6,673,008 B1 | 1/2004 | Thompson et al. | |
| 6,673,594 B1 | 1/2004 | Owen et al. | |
| 6,677,150 B2 | 1/2004 | Alford et al. | |
| 6,699,231 B1 | 3/2004 | Sterman et al. | |
| 6,736,836 B2 | 5/2004 | Montgomery | |
| 6,740,484 B1 | 5/2004 | Khirabadi et al. | |
| 6,773,877 B2 | 8/2004 | Fahy | |
| 6,794,124 B2 | 9/2004 | Steen | |
| 6,794,182 B2 | 9/2004 | Wolf, Jr. | |
| 6,905,871 B1 | 6/2005 | Doorschodt et al. | |
| 6,924,267 B2 | 8/2005 | Daemen et al. | |
| 6,953,655 B1 | 10/2005 | Hassanein et al. | |
| 6,977,140 B1 | 12/2005 | Owen et al. | |
| 6,994,954 B2 | 2/2006 | Taylor | |
| 7,005,253 B2 | 2/2006 | Polyak et al. | |
| 7,008,535 B1 | 3/2006 | Spears et al. | |
| 7,029,839 B2 | 4/2006 | Toledo-Pereyra et al. | |
| D531,319 S | 10/2006 | Schein et al. | |
| D531,320 S | 10/2006 | Garland et al. | |
| 7,157,222 B2 | 1/2007 | Khirabadi et al. | |
| 7,176,015 B2 | 2/2007 | Alford et al. | |
| 7,270,946 B2 | 9/2007 | Brockbank et al. | |
| 7,294,278 B2 | 11/2007 | Spears et al. | |
| 7,316,922 B2 | 1/2008 | Streeter | |
| 7,326,564 B2 | 2/2008 | Lundell et al. | |
| 7,361,365 B2 | 4/2008 | Birkett et al. | |
| 7,410,474 B1 | 8/2008 | Friend et al. | |
| 7,504,201 B2 | 3/2009 | Taylor et al. | |
| 7,572,622 B2 | 8/2009 | Hassanein et al. | |
| 7,651,835 B2 | 1/2010 | Hassanein et al. | |
| 7,678,563 B2 | 3/2010 | Wright et al. | |
| 7,691,622 B2 | 4/2010 | Garland et al. | |
| 7,749,693 B2 | 7/2010 | Brassil et al. | |
| 7,811,808 B2 | 10/2010 | van der Plaats et al. | |
| 7,824,848 B2 | 11/2010 | Owen et al. | |
| 7,897,327 B2 | 3/2011 | Millis et al. | |
| 8,097,449 B2 | 1/2012 | Garland et al. | |
| 8,268,547 B2 | 9/2012 | Owen et al. | |
| 8,268,612 B2 | 9/2012 | Owen et al. | |
| 8,304,181 B2 | 11/2012 | Hassanein et al. | |
| 8,420,380 B2 | 4/2013 | Fishman et al. | |
| 8,465,970 B2 | 6/2013 | Hassanein et al. | |
| 8,785,116 B2 | 7/2014 | Anderson et al. | |
| 8,828,710 B2 | 9/2014 | Anderson et al. | |
| 8,835,158 B2 | 9/2014 | Judson et al. | |
| 9,426,979 B2 | 8/2016 | Anderson et al. | |
| 2001/0025191 A1 | 9/2001 | Montgomery | |
| 2002/0042131 A1 | 4/2002 | Brockbank et al. | |
| 2002/0051779 A1 | 5/2002 | Gage et al. | |
| 2002/0064768 A1 | 5/2002 | Polyak et al. | |
| 2002/0068360 A1 | 6/2002 | Brockbank et al. | |
| 2002/0115634 A1 | 8/2002 | Polyak et al. | |
| 2002/0177117 A1 | 11/2002 | Wolf | |
| 2003/0022148 A1 | 1/2003 | Seki | |
| 2003/0053998 A1 | 3/2003 | Daemen et al. | |
| 2003/0118980 A1 | 6/2003 | Taylor | |
| 2003/0125804 A1 | 7/2003 | Kruse et al. | |
| 2003/0180704 A1 | 9/2003 | Brockbank et al. | |
| 2004/0014199 A1 | 1/2004 | Streeter | |
| 2004/0038192 A1 | 2/2004 | Brasile | |
| 2004/0038193 A1 | 2/2004 | Brasile | |
| 2004/0058432 A1 | 3/2004 | Owen et al. | |
| 2004/0067480 A1 | 4/2004 | Brockbank et al. | |
| 2004/0111104 A1 | 6/2004 | Schein et al. | |
| 2004/0170950 A1 | 9/2004 | Prien | |
| 2004/0171138 A1 | 9/2004 | Hassanein et al. | |

(56) References Cited

U.S. PATENT DOCUMENTS

| | | |
|---|---|---|
| 2004/0221719 A1 | 11/2004 | Wright et al. |
| 2004/0224298 A1 | 11/2004 | Brassil et al. |
| 2004/0224299 A1 | 11/2004 | Garland et al. |
| 2004/0241634 A1 | 12/2004 | Millis et al. |
| 2004/0248281 A1 | 12/2004 | Wright et al. |
| 2005/0100876 A1 | 5/2005 | Khirabadi et al. |
| 2005/0147958 A1 | 7/2005 | Hassanein et al. |
| 2005/0153271 A1 | 7/2005 | Wenrich |
| 2005/0221269 A1 | 10/2005 | Taylor et al. |
| 2005/0233299 A1 | 10/2005 | Sawa et al. |
| 2005/0255442 A1 | 11/2005 | Brassil et al. |
| 2005/0277106 A1 | 12/2005 | Daemen et al. |
| 2006/0019388 A1 | 1/2006 | Hutmacher et al. |
| 2006/0063142 A1 | 3/2006 | Owen et al. |
| 2006/0121439 A1 | 6/2006 | Baker |
| 2006/0121512 A1 | 6/2006 | Parenteau |
| 2006/0121605 A1 | 6/2006 | Parenteau |
| 2006/0141077 A1 | 6/2006 | Pettersson |
| 2006/0148062 A1 | 7/2006 | Hassanein et al. |
| 2006/0154357 A1 | 7/2006 | Hassanein et al. |
| 2006/0154358 A1 | 7/2006 | Hassanein et al. |
| 2006/0154359 A1 | 7/2006 | Hassanein et al. |
| 2006/0160204 A1 | 7/2006 | Hassanein et al. |
| 2006/0292544 A1 | 12/2006 | Hassanein et al. |
| 2007/0009881 A1 | 1/2007 | Arzt et al. |
| 2007/0015131 A1 | 1/2007 | Arzt et al. |
| 2007/0166292 A1 | 7/2007 | Brasile |
| 2007/0184545 A1 | 8/2007 | Plaats et al. |
| 2007/0190636 A1 | 8/2007 | Hassanein et al. |
| 2007/0243518 A1 | 10/2007 | Sema et al. |
| 2007/0275364 A1 | 11/2007 | Hassanein et al. |
| 2008/0017194 A1 | 1/2008 | Hassanein et al. |
| 2008/0070229 A1 | 3/2008 | Streeter |
| 2008/0070302 A1 | 3/2008 | Brockbank et al. |
| 2008/0096184 A1 | 4/2008 | Brasile |
| 2008/0145919 A1 | 6/2008 | Franklin et al. |
| 2008/0187901 A1 | 8/2008 | Doorschodt et al. |
| 2008/0234768 A1 | 9/2008 | Hassanein et al. |
| 2008/0286747 A1 | 11/2008 | Curtis et al. |
| 2008/0288399 A1 | 11/2008 | Curtis et al. |
| 2008/0311552 A1 | 12/2008 | Min |
| 2009/0197240 A1 | 8/2009 | Fishman et al. |
| 2009/0197241 A1 | 8/2009 | Fishman et al. |
| 2009/0197292 A1 | 8/2009 | Fishman et al. |
| 2009/0197324 A1 | 8/2009 | Fishman et al. |
| 2009/0197325 A1 | 8/2009 | Fishman et al. |
| 2009/0199904 A1 | 8/2009 | Babbitt et al. |
| 2009/0226878 A1 | 9/2009 | Taylor et al. |
| 2009/0240277 A1 | 9/2009 | Connors et al. |
| 2009/0291486 A1 | 11/2009 | Wenrich |
| 2010/0015592 A1 | 1/2010 | Doorschodt |
| 2010/0028850 A1 | 2/2010 | Brassil |
| 2010/0056966 A1 | 3/2010 | Toth |
| 2010/0086907 A1 | 4/2010 | Bunegin et al. |
| 2010/0112542 A1 | 5/2010 | Wright et al. |
| 2010/0151559 A1 | 6/2010 | Garland et al. |
| 2010/0171802 A1* | 7/2010 | Lee .................. B41J 2/17513 347/87 |
| 2010/0209902 A1 | 8/2010 | Zal et al. |
| 2010/0216110 A1 | 8/2010 | Brockbank |
| 2010/0221696 A1 | 9/2010 | Owen et al. |
| 2010/0233670 A1 | 9/2010 | Gavish |
| 2010/0234928 A1 | 9/2010 | Rakhorst et al. |
| 2011/0033916 A1 | 2/2011 | Hutzenlaub et al. |
| 2011/0039253 A1 | 2/2011 | Owen et al. |
| 2011/0053256 A1 | 3/2011 | Owen et al. |
| 2011/0059429 A1 | 3/2011 | Owen et al. |
| 2011/0129810 A1 | 6/2011 | Owen et al. |
| 2011/0129908 A1 | 6/2011 | Owen et al. |
| 2011/0136096 A1 | 6/2011 | Hassanein et al. |
| 2011/0177487 A1 | 7/2011 | Simsir et al. |
| 2011/0183310 A1 | 7/2011 | Kravitz et al. |
| 2011/0212431 A1 | 9/2011 | Bunegin et al. |
| 2011/0217689 A1 | 9/2011 | Bunegin et al. |
| 2012/0116152 A1 | 5/2012 | Faulkner et al. |
| 2012/0148542 A1 | 6/2012 | Kravitz |
| 2012/0309078 A1 | 12/2012 | Anderson et al. |
| 2014/0087357 A1 | 3/2014 | Kohl et al. |
| 2014/0314881 A1 | 10/2014 | Reynolds et al. |
| 2014/0349273 A1 | 11/2014 | Anderson et al. |
| 2014/0356850 A1 | 12/2014 | Anderson et al. |
| 2014/0356933 A1 | 12/2014 | Anderson et al. |
| 2015/0017627 A1 | 1/2015 | Anderson et al. |
| 2016/0074234 A1 | 3/2016 | Abichandani et al. |
| 2018/0352807 A1 | 12/2018 | Judson et al. |
| 2019/0320649 A1* | 10/2019 | Bunegin ............... A01N 1/0247 |

FOREIGN PATENT DOCUMENTS

| | | |
|---|---|---|
| CN | 101322861 A | 12/2008 |
| CN | 105660603 A | 6/2016 |
| CN | 205337358 U | 6/2016 |
| DE | 19922310 A1 | 11/2000 |
| DE | 102005048625 A1 | 4/2007 |
| EP | 0376763 A2 | 7/1990 |
| EP | 2278874 A1 | 2/2011 |
| EP | 2480069 A1 | 8/2012 |
| JP | 8-169801 | 7/1996 |
| JP | 2008-120713 A | 5/2008 |
| WO | 97/43899 A1 | 11/1997 |
| WO | 99/15011 A1 | 4/1999 |
| WO | 00/18225 A1 | 4/2000 |
| WO | 00/18226 A2 | 4/2000 |
| WO | 00/60935 A1 | 10/2000 |
| WO | 01/03505 A1 | 1/2001 |
| WO | 01/37719 A2 | 5/2001 |
| WO | 01/54495 A1 | 8/2001 |
| WO | 01/78504 A2 | 10/2001 |
| WO | 01/78505 A1 | 10/2001 |
| WO | 01/95717 A2 | 12/2001 |
| WO | 02/17714 A2 | 3/2002 |
| WO | 02/26034 A2 | 4/2002 |
| WO | 02/32225 A2 | 4/2002 |
| WO | 02/089571 A1 | 11/2002 |
| WO | 2004/017838 A2 | 3/2004 |
| WO | 2004/026031 A2 | 4/2004 |
| WO | 2004/052101 A1 | 6/2004 |
| WO | 2004/089085 A2 | 10/2004 |
| WO | 2004/089090 A1 | 10/2004 |
| WO | 2004/105484 A1 | 12/2004 |
| WO | 2004/110146 A1 | 12/2004 |
| WO | 2005/022994 A1 | 3/2005 |
| WO | 2005/074681 A2 | 8/2005 |
| WO | 2005/099588 A2 | 10/2005 |
| WO | 2006/033674 A1 | 3/2006 |
| WO | 2006/042138 A2 | 4/2006 |
| WO | 2006/052133 A2 | 5/2006 |
| WO | 2006/060709 A2 | 6/2006 |
| WO | 2007/111495 A1 | 10/2007 |
| WO | 2007/124044 A2 | 11/2007 |
| WO | 2008/108996 A1 | 9/2008 |
| WO | 2008/144021 A2 | 11/2008 |
| WO | 2008/150587 A2 | 12/2008 |
| WO | 2009/020412 A1 | 2/2009 |
| WO | 2009/041806 A1 | 4/2009 |
| WO | 2009/099939 A2 | 8/2009 |
| WO | 2009/132018 A1 | 10/2009 |
| WO | 2010/084424 A1 | 7/2010 |
| WO | 2010/096821 A2 | 8/2010 |
| WO | 2011/038251 A1 | 3/2011 |
| WO | 2012/125782 A2 | 9/2012 |
| WO | 2015/126853 A1 | 8/2015 |
| WO | 2018/015548 A2 | 1/2018 |
| WO | 2018/112072 A1 | 6/2018 |

OTHER PUBLICATIONS

Bunegin, et al., The Application of Fluidics Technology for Organ Preservation, Biomedical Instrumentation & Technology, Mar./Apr. 2004, pp. 155-164.

Calhoon, et al., Twelve-Hour Canine Heart Preservation With a Simple, Portable Hypothermic Organ Perfusion Device Ann Thorac Surg 1996:62:91-3.

(56) References Cited

OTHER PUBLICATIONS

International Preliminary Report on Patentability for PCT Application No. PCT/US2009/041274.
International Search Report and Written Opinion for PCT Application No. PCT/US2010/050230, (12 pages).
International Search Report and Written Opinion dated Dec. 16, 2013, for International Patent Application No. PCT/US2013/054353, filed Aug. 9, 2013 (8 pages).
International Search Report and Written Opinion dated Dec. 9, 2013, for International Patent Application No. PCT/US2013/054365, filed Aug. 9, 2013 (10 pages).
International Search Report for PCT Application No. PCT/US2009/041274, (2 pages).
Irish Medicines Board "Viaspan" Summary of Product Characteristics available online at <https://www.hpra.ie/img/.../LicenseSPC_PA0002-075-001_21112012111041.pdf>, Nov 21, 2012 (6 Pages).
LifePort Brochure, Organ Recovery Systems obtained from www.organ-recovery.com.
Steinbrook, The New England Journal of Medicine, Organ Donation after Cardiac Death, Jul. 19, 2007.
Tolstykh, et al., Novel portable hypothermic pulsatile perfusion preservation technology: Improved viability and function of rodent and canine kidneys, Ann Transplant, 2010; 15(3):1-9.
Tolstykh, et al., Perfusion Preservation of Rodent Kidneys in a Portable Preservation Device Based on Fluidics Technology, vol. 73, 1508-1526, No. 9, May 15, 2002.
Wandall, et al., Galactosylation does not prevent the rapid clearance of long-term 40C-stored platelets, Blood, 2008; 111(6):3249-3256.
Weegman, et al., Continuous Real-time Viability Assessment of Kidneys Based on Oxygen Consumption, Transplant Proc. 2010; 42(6): 2020-2023.
Extended European Search Report issued in European application No. 13828327.0 dated Feb. 9, 2016, 7 pages.
De Perrot, 2004, Lung preservation, Seminars in Thoracic and Cardiovascular Surgery, Saunders, Philadelphia, PA, US, 16(4):300-308.
Extended European Search Report issued in European Patent Application No. 18812781.5, dated Feb. 11, 2021, 8 pages.
Bunegin, et al., Interstitial pO2 and High Energy Phosphates in the Canine Heart during Hyopthermic Preservation in a New, Portable, Pulsatile Perfusion Device, from the Department of Anesthesiology University of Texas Health Science Center at San Antonio, Texas; and Center for Cardiovascular Surgery of the Republic of Lithuania, Vilnius, Lithuania, vol. 3, No. 3, Oct. 1998, pp. 1-6.
Bunegin, et al., The Application of Fluidics Based Technology for Perfusion Preservation of Adult, Human Sized, Canine Hearts, from the Department of Anesthesiology, HEalth Science Center at San Antonio, University of Texas, vol. 8, No. 1/2 (2003), pp. 73-78.
Bunegin, et al., The Application of Fluids Technology for Organ Preservation, Biomedical Instrumentation & Technology, Mar./Apr. 2004, pp. 155-164.
Calhoon, et al., Twelve-Hour Canine Heart Preservation With a Simple, Portable Hypothermic Organ Perfusion Device, Ann Thorac Surg, 1996;62:91-93.
Final Office Action issued in U.S. Appl. No. 16/542,050, dated Jan. 13, 2021, 17 pages.
International Preliminary Report on Patentability issued in International Application No. PCT/US2009/041274, dated Jun. 24, 2009 (5 pages).
International Search Report and Written Opinion issued in International Application No. PCT/US2009/041274, dated Jun. 24, 2009 (6 pages).
International Search Report and Written Opinion issued in International Application No. PCT/US2010/050230, dated Feb. 14, 2011 (12 pages).
International Search Report and Written Opinion issued in International Application No. PCT/US2013/054353, dated Dec. 16, 2013 (8 pages).
International Search Report and Written Opinion issued in International Application No. PCT/US2013/054365, dated Dec. 9, 2013 (10 pages).
International Search Report and Written Opinion issued in International Application No. PCT/US2018/036508, dated Aug. 30, 2018 (9 pages).
International Search Report and Written Opinion issued in International Application No. PCT/US2020/047324, dated Oct. 4, 2020 (15 pages).
International Search Report and Written Opinion issued in International Application No. PCT/US2021/15708, dated May 7, 2021 (10 pages).
International Search Report and Written Opinion of the International Searching Authority dated Aug. 30, 2018 for nternational Application No. PCT/US2018/036508 (14 pages).
Steinbrook, The New England Journal of Medicine, Organ Donation after Cardiac Death. Jul. 9, 2007 (5 pages).
Tolstykh, et al., Novel protable hypothermic pulsatile perfusion preservation technology: Improved viability and function of rodent and canine kidneys, Ann Transplant, 2010; 15(3):1-9.
Tolstykh, et al., Perfusion Preservation of Rodent Kidneys in a Portable Preservation Device Based on Fuidics Technology, May 15, 2002, vol. 73, No. 9, 1508-1526.
Wandall, et al., Galactosylation does not prevent the rapid clearance of long-term 40C-stored platelets, Blood, 2008; 11(6)3249-3256.
Weegman, et al., Continuous Real-time Viability Assessment of Kidneys Based on Oxygen Consumption, Transplant Proc. 2010; 42(6)1020-2023.

* cited by examiner

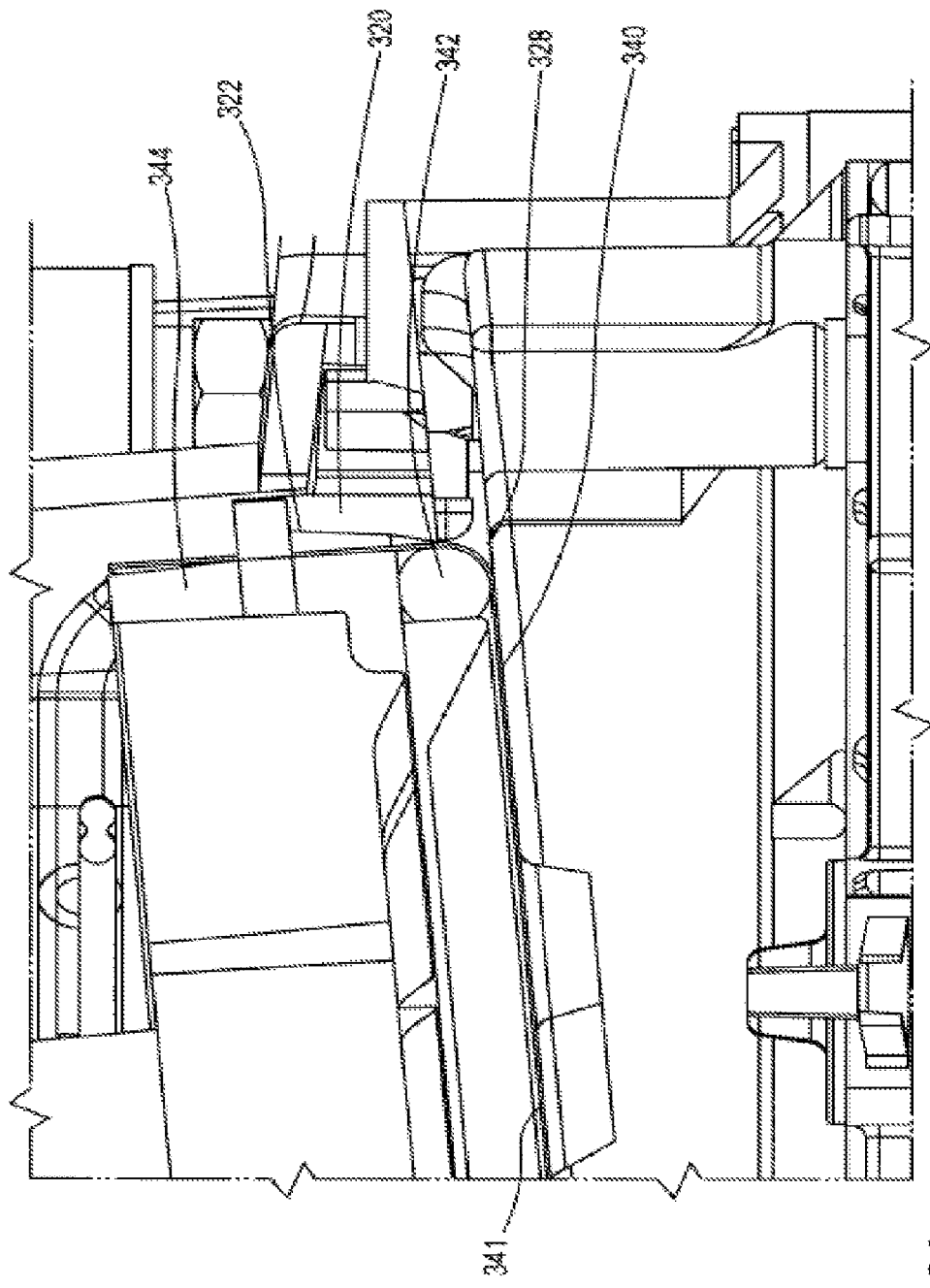

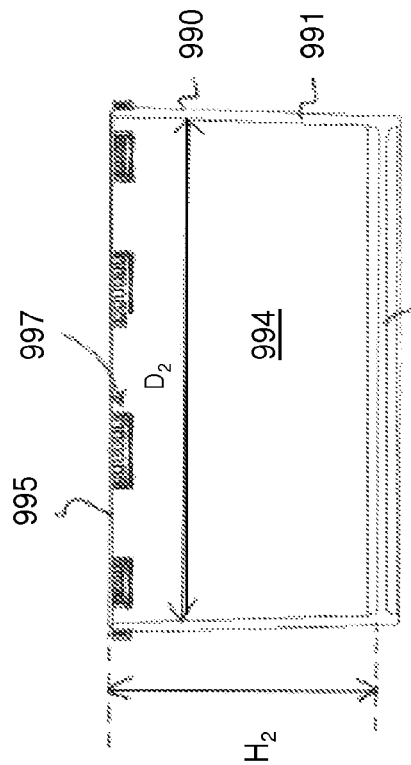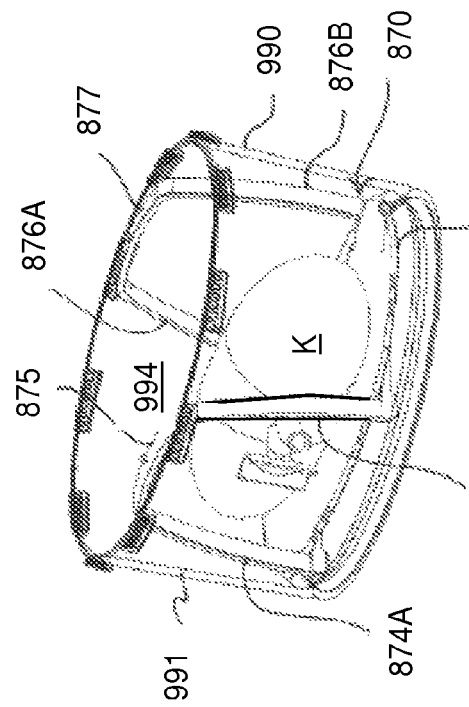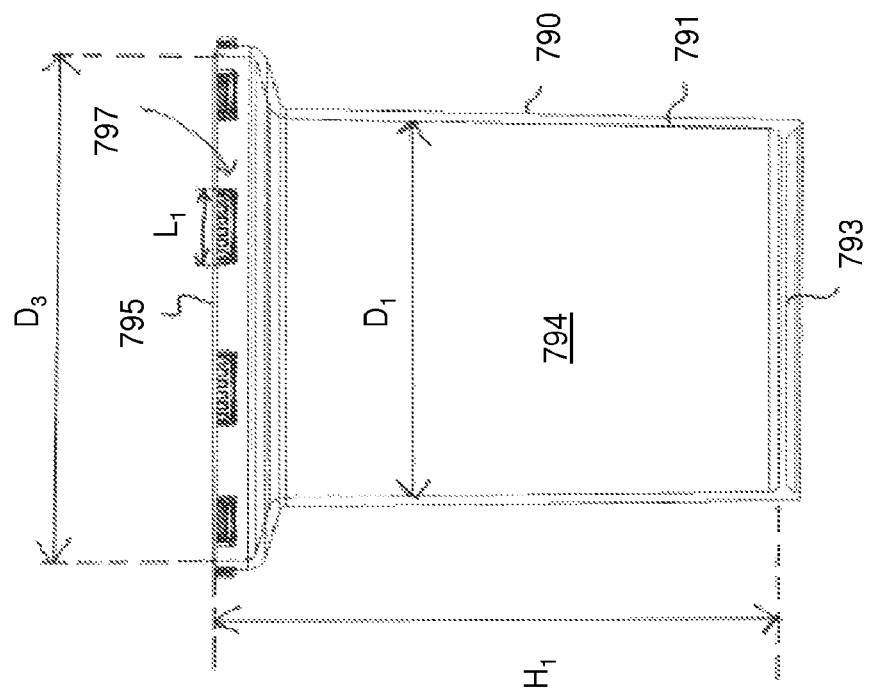

Physical Properties of Select Preservation Solutions

EC: Eurocollins, PBS: Phosphate-Buffered-Sucrose, HOC: Hypertonic Citrate, HTK: Histidine-Tryptophane-Ketoglutarate, UW: University of Wisconsin Cold Storage Solution, GSH: glutathion

|  | EC | PBS | HOC | HTK | UW | Celsior |
|---|---|---|---|---|---|---|
| Na/K ratio | K \| Na | Na \| K | Na \| K | Na \| K | K \| Na | Na \| K |
| Buffer | Phosphate | Phosphate | Citrate | Histidine | Phosphate | Phosphate |
| Impermeants | Glucose | Sucrose | Mannitol Citrate Magnesium | Mannitol Histidine bionate | Raffinose Lacto- bionate | Mannitol Lacto- |
| pH | 7.3 | 7.2 | 7.1 | 7.3 | 7.4 | 7.3 |
| Osmolality | 340 | 310 | 400 | 310 | 320 | 360 |

Substrates of Select Preservation Solutions

|  | EC | PBS | HOC | HTK | UW | Celsior |
|---|---|---|---|---|---|---|
| Scavengers |  |  |  | Mannitol | GSH | Mannitol |
| Substrates |  |  |  | Keto-glutarate | Adenosine | Glutamate |

FIG. 41

Compositions of Select Preservation Solutions

EC: EuroCollins, PBS: Phosphate-Buffered-Sucrose, HTK: Histidine-Tryptophan-Ketoglutarate,
UW: University of Wisconsin Cold Storage Solution, HOC: Hypertonic Citrate, HES: hydroxyethyl starch,
ROS: reactive-oxygen-species

| | Collins | EC | UW | PBS | HTK | HOC | Celsior |
|---|---|---|---|---|---|---|---|
| Electrolytes (mM) | | | | | | | |
| Calcium | - | - | - | - | - | - | 0.26 |
| Chloride | 15 | 15 | 20 | - | 32 | - | 41.5 |
| Magnesium | 30 | - | 5 | - | 4 | 35 | 13 |
| Phosphate | 50 | 50 | - | 60 | - | - | - |
| Potassium | 115 | 115 | 100 | - | 9 | 80 | 15 |
| Sodium | 10 | 10 | 25 | 125 | 15 | 80 | 100 |
| Sulphate | 30 | - | 5 | - | - | 40 | - |
| Buffers (mM) | | | | | | | |
| Citrate | - | - | - | - | - | 55 | - |
| Histidine | - | - | - | - | 198 | - | 30 |
| $K_2HPO_4$ | 15 | 15 | - | - | - | - | - |
| $KH_2PO_4$ | 42.5 | 42.5 | 25 | - | - | - | - |
| $Na_2HPO_4$ | - | - | - | 56 | - | - | - |
| $NaHCO_3$ | 10 | 10 | - | - | - | - | - |
| $NaH_2PO_4$ | - | - | - | 13 | - | - | - |
| Impermeants (mM) | | | | | | | |
| Glucose | 25 | 195 | - | - | - | - | - |
| Histidine | - | - | - | - | 198 | - | 30 |
| Lactobionate | - | - | 100 | - | - | - | 80 |
| Mannitol | - | - | - | - | 30 | 185 | 60 |
| Raffinose | - | - | 30 | - | - | - | - |
| Sucrose | - | - | - | 140 | - | - | - |
| Colloids (g/l) | | | | | | | |
| HES | - | - | 50 | - | - | - | - |
| ROS scavengers (mM) | | | | | | | |
| Allopurinol | - | - | 1 | - | - | - | - |
| Glutathione | - | - | 3 | - | - | - | 3 |
| Mannitol | - | - | - | - | 38 | 185 | 60 |
| Tryptophan | - | - | - | - | 2 | - | - |
| Substrates (mM) | | | | | | | |
| Adenosine | - | - | 5 | - | - | - | - |
| Glutamate | - | - | - | - | - | - | 20 |
| Ketoglutarate | - | - | - | - | 1 | - | - |

FIG. 42

SYSTEM FOR HYPOTHERMIC TRANSPORT OF SAMPLES

CROSS-REFERENCE TO RELATED APPLICATIONS

This application claims priority to U.S. patent application Ser. No. 13/572,315, filed Aug. 10, 2012, which is a continuation-in-part of U.S. patent application Ser. No. 13/420,962 filed Mar. 15, 2012, which claims priority to U.S. Provisional Application Ser. No. 61/541,425, filed Sep. 30, 2011, and U.S. Provisional Application Ser. No. 61/452,917, filed Mar. 15, 2011, all of which are incorporated herein by reference in their entireties.

FIELD OF THE INVENTION

The invention relates to systems and method for hypothermic transport of biological samples, for example tissues for donation. The systems and methods provide a secure, sterile, and temperature-controlled environment for transporting the samples

BACKGROUND

There is a critical shortage of donor organs. Hundreds of lives could be saved each day if more organs (heart, kidney, lung, etc.) were available for transplant. While the shortage is partly due to a lack of donors, there is a need for better methods of preserving and transporting donated organs. Current storage and preservation methods allow only a small time window between harvest and transplant, typically on the order of hours. These time windows dictate who is eligible to donate organs and who is eligible to receive the donated organs. These time windows also result in eligible organs going unused because they cannot be transported to a recipient in time.

The transport window is most acute for heart transplants. Current procedures dictate that hearts cannot be transplanted after four hours of ischemia (lack of blood supply). Because of this time limit, a donor heart cannot be transplanted into a recipient who is located more than 500 miles (800 km) from the harvest. In the United States, this means that a critically-ill patient in Chicago will be denied access to a matching donor heart from New York City. If the geographic range of donors could be extended, thousands of lives would be saved each year.

While several state-of-the-art preservation methods are available to keep organs viable within a hospital, transport preservation typically involves simple hypothermic (less than 10° C.) storage. Contemporary transport storage (i.e. "picnic cooler" storage) typically involves bagging the organ in cold preservation solution and placing the bagged organ in a portable cooler along with ice for the journey. There are no additional nutrients or oxygen provided to the organ. For the most part, the hope is that the preservation solution will reduce swelling and keep the tissues moist, while the cold reduces tissue damage due to hypoxia.

This method of transport has several known shortcomings, however. First, the temperature is not stabilized. Because the temperature of the organ is determined by the rate of melting and the thermal losses of the cooler, an organ will experience a wide range of temperatures during transport. For example, the temperatures can range from nearly 0° C., where the organ risks freezing damage, to 10-15° C., or greater, where the organ experiences greater tissue damage due to hypoxia.

Second, the organ does not receive sufficient oxygen and nutrients. Even though the metabolic rate is greatly slowed by the low temperatures, the tissues still require oxygen and nutrients to be able to function normally once the tissue is warmed. While some nutrients are provided by the preservation fluid surrounding the organ, the nutrients are not readily absorbed by the exterior of the organ due to the presence of a protective covering, e.g., the renal capsule.

Third, there is little protection against mechanical shock. An organ sealed in bag and then placed in a cooler with ice is subject to bruising and abrasion as the organ contacts ice chunks or the sides of the cooler. Mechanical damage can be especially problematic when the organ is airlifted and the aircraft experiences turbulence.

One newer alternative to "picnic cooler" transport is to transport the sample in a container that actively perfuses the sample with a preservation fluid, for example, University of Wisconsin solution. Such systems typically require a battery to power the pump, which means that the overall system is heavier, and limited to the useable lifespan of the battery. Perfusion transport systems also suffer from bubble formation within the perfusate due to constant jostling of the system during transport. In some cases, bubbles formed in the perfusate may be accidentally forced into the capillaries of the sample (e.g., donor heart) causing irreparable harm. An organ that is spoiled because of bubbles may not be identified as damaged until it is transplanted into a donor.

Improved transport and storage for organs would increase the pool of available organs while improving outcomes for recipients.

SUMMARY

The invention provides an improved system for transporting biological samples, e.g. tissues, such as donor organs. This improved system will greatly expand the window of time for organ transportation and will, consequently, make many more organs available for donation. Additionally, the samples will be healthier upon arrival, as compared to state-of-the-art transport methods.

The disclosed system for hypothermic transport overcomes the shortcomings of the prior art by providing a sterile, temperature-stabilized environment for the samples while providing the ability to monitor the temperature of the samples during transport. Additionally, because the samples are suspended in an oxygenated preservation fluid, the delivered samples avoid mechanical damage, remain oxygenated, and are delivered healthier than samples that have been merely sealed in a plastic bag. The systems additionally provide mechanisms, e.g. ports, to release trapped rising fluids, e.g., air, from the system while the system is being filled and operating. This feature prevents rising fluids from being recirculated in the preservation fluid and perfused into the tissues being preserved. This feature is especially important during loading, when air trapped in crevices of a container must be forced out so that the air will not form bubbles in the preservation fluid that could damage the tissues.

In some cases in which the sample is a tissue, the preservation solution is circulated through the tissue using the tissue's cardiovascular system. In this case, a pulsed flow is used to imitate the natural environment of the tissue. Such conditions improve absorption of nutrients and oxygen as compared to static storage. Additionally, because compressed oxygen is used to propel the pulsed circulation, the preservation fluid is reoxygenated during transport, replacing the oxygen that has been consumed by the tissue and displacing waste gases (i.e., $CO_2$). In some instances, a suite of sensors measures temperature, oxygen content, and pressure of the circulating fluids to assure that the tissue experiences a favorable environment during the entire transport.

The methods of the invention involve storing and/or transporting the severed tissue in a container in the presence of a preservation fluid, typically a pressurized, oxygenated preservation fluid. The container may additionally provide a time varying pressure greater than atmospheric pressure on the preservation fluid, thereby simulating for the interior tissues (muscles, nerves, etc.) a pressure environment analogous to that experienced when the tissue was attached. In some instances, the container will be kept at a hypothermal temperature in order to better preserve the tissue. In some instances the preservation solution will contain nutrients and/or electrolytes.

In one instance, a system for the hyporthermic transport of a biological sample includes a self-purging preservation apparatus and an insulated transport container for receiving the self-purging preservation apparatus and cooling media. The self-purging preservation apparatus includes an organ chamber and a lid assembly. The lid assembly has a pumping chamber with a semi-permeable membrane that is capable of exerting a force against a preservation fluid when a pressure is applied against the semi-permeable membrane. The self-purging preservation apparatus has a fill port to allow the preservation fluid to be added to the apparatus after the apparatus has been closed, and a purge port to allow the preservation fluid to exit the apparatus once filled. The purge port also allows a rising fluid to exit the apparatus during operation of the apparatus. In some instances, the self-purging preservation apparatus includes a temperature sensor. The self-purging preservation apparatus may also include a temperature display. The insulated transport container may be configured to hold a compressed oxygen source.

Systems for hypothermic transport of samples will be used to transport biological samples, such as tissues, organs, and body fluids. Methods may include providing a hypothermic transport system including a self-purging preservation apparatus and an insulated transport container for receiving the self-purging preservation apparatus and cooling media, suspending a biological sample in the preservation fluid in the first transport container, and maintaining a temperature of the preservation fluid between 2 and 8° C. for at least 60 minutes.

In one instance, a self-purging preservation apparatus of the invention is configured to oxygenate and perfuse the detached tissue. The self-purging preservation apparatus may also monitor the health of the tissue by measuring parameters such as oxygen consumption. The self-purging preservation apparatus includes a pneumatic system, a pumping chamber, and a tissue chamber. The pneumatic system is configured for the controlled delivery of fluid to and from the pumping chamber based on a predetermined control scheme. The predetermined control scheme can be, for example, a time-based control scheme or a pressure-based control scheme. The pumping chamber may additionally be configured to diffuse a gas into a perfusate and to generate a pulse wave for moving the perfusate through the tissue.

In some instances, the self-purging preservation apparatus is configured to substantially automatically purge excess fluid from the tissue chamber to the pumping chamber. The pumping chamber may then, in turn, be configured to self-purge excess fluid from the pumping chamber to an area external to the self-purging preservation apparatus. For example, the pumping chamber, disposed in the lid assembly, may be separated into first and second portions by a membrane, and the membrane disposed so that rising fluid will be directed to a highest point and then out of the container, for example, through a purge port.

In general, the design makes it easy for a doctor or technician to load an organ for transport securely and safely. Once loaded, the organ can be transported in a hyperthermic state with ongoing pulsatile perfusion, thereby extending the ex corporal longevity of the organ for twelve hours or more. This extended transit time will greatly expand the donor pool for organs, and make it possible to store tissues for much longer periods prior to transport.

BRIEF DESCRIPTION OF THE DRAWINGS

FIG. 16A is an enlarged cross-sectional view of the portion of FIG. 14 identified by the line 16A.

FIG. 29 is a front view of the canister of the self-purging preservation apparatus of FIG. 19.

FIG. 30 is a front view of a canister according to an embodiment.

FIG. 31 is a perspective view of the canister of FIG. 30 and a tissue.

FIG. 41 shows a table of physical properties of selected preservation solutions and a table of substrates of selected preservation solutions. The information in the tables is adapted from t'Hart et al. "New Solutions in Organ Preservation," *Transplantation Reviews* 2006, vol. 16, pp. 131-141 (2006).

FIG. 42 shows a table of compositions of selected preservation solutions. The information in the table is adapted from t'Hart et al. "New Solutions in Organ Preservation," *Transplantation Reviews* 2006, vol. 16, pp. 131-141 (2006).

DETAILED DESCRIPTION

Figure 1:
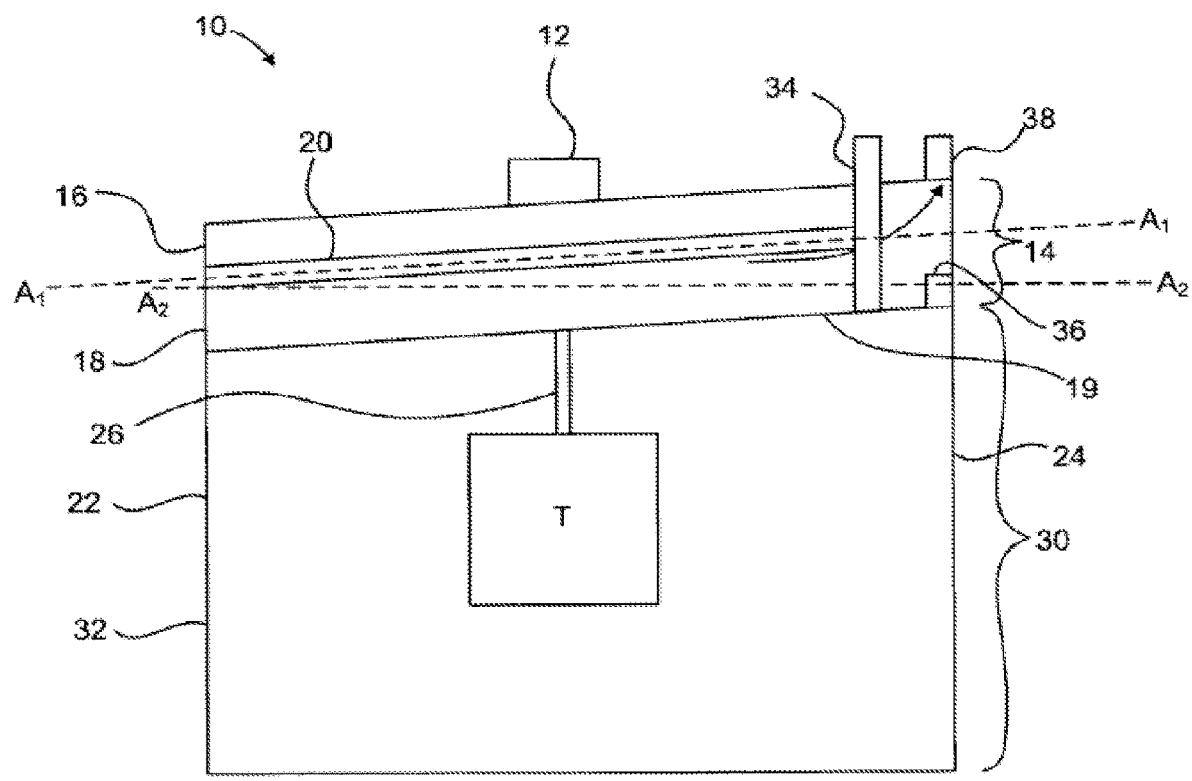
FIG. 1 is a schematic illustration of a self-purging preservation apparatus according to an embodiment.

The disclosed systems for hypothermic transport of samples provide a sterile, temperature-stabilized environment for transporting samples while providing an ability to self-purge the system of rising fluids, e.g., trapped gas. Some systems also provide the ability to monitor the temperature, or other properties of the samples, during transport. Because of these improvements, users of the invention can reliably transport samples over much greater distances, thereby substantially increasing the pool of available tissue donations. Additionally, because the tissues are in better condition upon delivery, the long-term prognosis for the recipient is improved.

Hypothermic transport systems of the invention comprise a self-purging preservation apparatus and an insulated transport container. The self-purging preservation apparatus will receive the tissue for transport, and keep it suspended or otherwise supported in a surrounding pool of preservation solution. The self-purging preservation apparatus may comprise a number of configurations suitable to transport tissues hypothermicly.

In some embodiments, the self-purging preservation apparatus will include a pumping mechanism to circulate the preservation solution or perfuse an organ with the preservation solution. A self-purging preservation apparatus comprising a pumping chamber will be referred to as "pulsatile." While the pumping is pulsating in preferred embodiments, the pumping is not intended to be limited to pulsating pumping, that is, the pumping may be continuous. In other embodiments, the self-purging preservation apparatus will not circulate or perfuse the preservation solution. A non-pumping self-purging preservation apparatus will be referred to as "static."

In some embodiments, a device is configured to self-purge excess fluid (e.g., liquid and/or gas). For example, in some embodiments, a device includes a lid assembly in which at least a portion of the lid assembly is inclined with respect to a horizontal axis. The inclined portion of the lid assembly is configured to facilitate the flow of fluid towards a purge port disposed at substantially the highest portion of a chamber of the lid assembly. In this manner, excess fluid can escape the device via the purge port. Also in this manner, when excess liquid is expelled from the device via the purge port, an operator of the device can determine that any excess gas has also been purged from the device, or at least from within a tissue chamber of the device, because the gas is lighter than the liquid and will move towards and be expelled via the purge port before excess liquid.

In some embodiments, a device is configured to pump oxygen through a pumping chamber to oxygenate a perfusate and to perfuse a tissue based on a desired control scheme. For example, in some embodiments, the device includes a pneumatic system configured to deliver oxygen to the pumping chamber on a time-based control scheme. The pneumatic system can be configured to deliver oxygen to the pumping chamber for a first period of time. The pneumatic system can be configured to vent oxygen and carbon dioxide from the pumping chamber for a second period of time subsequent to the first period of time. In another example, in some embodiments, the device includes a pneumatic system configured to deliver oxygen to the pumping chamber on a pressure-based control scheme. The pneumatic system can be configured to deliver oxygen to the pumping chamber until a first threshold pressure is reached within the pumping chamber. The pneumatic system can be configured to vent oxygen and carbon dioxide from the pumping chamber until a second threshold pressure is reached within the pumping chamber. In some embodiments, a power source of the device is in use when oxygen is being delivered to the pumping chamber and is not in use when oxygen and carbon dioxide are being vented from the pumping chamber. In this manner, the device is configured to help minimize usage of the power source, and thus the device can prolong the period of time a tissue is extracorporeally preserved within the device before the power source is depleted. Such an improvement increases the time available for transporting the tissue to a hospital for replantation.

As used in this specification, the singular forms "a," "an" and "the" include plural referents unless the context clearly dictates otherwise. Thus, for example, the term "a fluid" is intended to mean a single fluid or a combination of fluids.

As used herein, "a fluid" refers to a gas, a liquid, or a combination thereof, unless the context clearly dictates otherwise. For example, a fluid can include oxygen, carbon dioxide, or another gas. In another example, a fluid can include a liquid. Specifically, the fluid can be a liquid perfusate. In still another example, the fluid can include a liquid perfusate with a gas, such as oxygen, mixed therein or otherwise diffused therethrough.

As used herein, "tissue" refers to any tissue of a body of a patient, including tissue that is suitable for being replanted or suspected of being suitable for replantation. Tissue can include, for example, muscle tissue, such as, for example, skeletal muscle, smooth muscle, or cardiac muscle. Specifically, tissue can include a group of tissues forming an organ, such as, for example, the skin, lungs, cochlea, heart, bladder, liver, kidney, or other organ. In another example, tissue can include nervous tissue, such as a nerve, the spinal cord, or another component of the peripheral or central nervous system. In still another example, tissue can include a group of tissues forming a bodily appendage, such as an arm, a leg, a hand, a finger, a thumb, a foot, a toe, an ear, genitalia, or another bodily appendage. While the systems are described as relating to the transport of tissues, such as organs, it is also envisioned that the systems could be used for the transport of body fluids, which may be held in another container within the self-purging preservation apparatus. Body fluids may include blood and blood products (whole blood, platelets, red blood cells, etc.) as well as other body fluids for preservation.

A self-purging preservation apparatus 10 according to an embodiment is schematically illustrated in FIG. 1. The self-purging preservation apparatus 10 is configured to oxygenate a perfusate (not shown) received in a pumping chamber 14 of the self-purging preservation apparatus. The self-purging preservation apparatus 10 includes a valve 12 configured to permit a fluid (e.g., oxygen) to be introduced into a first portion 16 of the pumping chamber 14. A membrane 20 is disposed between the first portion 16 of the pumping chamber 14 and a second portion 18 of the pumping chamber. The membrane 20 is configured to permit the flow of a gas between the first portion 16 of the pumping chamber 14 and the second portion 18 of the pumping chamber through the membrane. The membrane 20 is configured to substantially prevent the flow of a liquid between the second portion 18 of the pumping chamber 14 and the first portion 16 of the pumping chamber through the membrane. In this manner, the membrane can be characterized as being semi-permeable.

The membrane 20 is disposed within the pumping chamber 14 along an axis A1 that is transverse to a horizontal axis A2. Said another way, the membrane 20 is inclined, for example, from a first side 22 to a second side 24 of the self-purging preservation apparatus 10. The membrane may be inclined at an angle between 0.5° and 40° relative to horizontal, e.g., between 1° and 30°, e.g., between 5° and 25°, e.g., between 10° and 20°. For example, the membrane may be inclined at an angle between 1° and 10°. As such, as described in more detail below, a rising fluid in the second portion 18 of the pumping chamber 14 will be directed by the inclined membrane 20 towards a port 38 disposed at the highest portion of the pumping chamber 14, thereby allowing the rising fluid to leave the apparatus during filling or during transport. The vent port 38 is configured to permit the fluid to flow from the pumping chamber 14 into the atmosphere external to the self-purging preservation apparatus 10. In some embodiments, the vent port 38 is configured for unidirectional flow, and thus is configured to prevent a fluid from being introduced into the pumping chamber 14 via the port (e.g., from a source external to the self-purging preservation apparatus 10). In some embodiments, the vent port 38 includes a luer lock.

The second portion 18 of the pumping chamber 14 is configured to receive a fluid. In some embodiments, for example, the second portion 18 of the pumping chamber 14 is configured to receive a liquid perfusate. The second portion 18 of the pumping chamber 14 is in fluid communication with an adapter 26. The adapter 26 is configured to permit movement of the fluid from the pumping chamber 14 to a tissue T. For example, in some embodiments, the pumping chamber 14 defines an aperture (not shown) configured to be in fluidic communication with a lumen (not shown) of the adapter 26. The adapter 26 is configured to be coupled to the tissue T. The adapter 26 can be coupled to the tissue T in any suitable manner. For example, in some embodiments, the adapter 26 is configured to be sutured to the tissue T. In another example, the adapter 26 is coupleable to the tissue T via an intervening structure, such as silastic or other tubing. In some embodiments, at least a portion of the adapter 26, or the intervening structure, is configured to be inserted into the tissue T. For example, in some embodiments, the lumen of the adapter 26 (or a lumen of the intervening structure) is configured to be fluidically coupled to a vessel of the tissue T.

In some embodiments, the adapter 26 is configured to support the tissue T when the tissue T is coupled to the adapter. For example, in some embodiments, the adapter 26 includes a retention mechanism (not shown) configured to be disposed about at least a portion of the tissue T and to help retain the tissue T with respect to the adapter. The retention mechanism can be, for example, a net, a cage, a sling, or the like. In some embodiments, the self-purging preservation apparatus 10 includes a basket (not shown) or other support mechanism configured to support the tissue T when the tissue T is coupled to the adapter 26 or otherwise received in the self-purging preservation apparatus 10.

The adapter 26 may be of a variety of structures suitable to suspend the tissue T in the preservation solution while minimizing the potential for mechanical damage, e.g., bruising or abrasion. In some embodiments, the adapter 26 is configured to be sutured to the tissue T. In another example, the adapter 26 is coupleable to the tissue T via an intervening structure, such as silastic or other tubing. In some embodiments, at least a portion of the adapter 26, or the intervening structure, is configured to be inserted into the tissue T. In some embodiments, the adapter 26 is configured to support the tissue T when the tissue T is coupled to the adapter. For example, in some embodiments, the adapter 26 includes a retention mechanism configured to be disposed about at least a portion of the tissue T and to help retain the tissue T with respect to the adapter. The retention mechanism can be, for example, a net, a cage, a sling, or the like.

In some embodiments, a self-purging preservation apparatus may additionally include a basket or other support mechanism configured to support the tissue T when the tissue T is coupled to the adapter 26 or otherwise suspended in the self-purging preservation apparatus. The support mechanism may be part of an insert which fits within the self-purging preservation apparatus. The basket may include connectors which may be flexible or hinged to allow the basket to move in response to mechanical shock, thereby reducing the possibility of damage to tissue T. In other embodiments, the basket may be coupled to the lid assembly so that it is easily immersed in and retracted from the preservation fluid held in the tissue chamber.

A tissue chamber 30 is configured to receive the tissue T and a fluid. In some embodiments, the self-purging preservation apparatus 10 includes a fill port 34 that is extended through the self-purging preservation apparatus 10 (e.g., through the pumping chamber 14) to the tissue chamber 30. The port 34 is configured to permit fluid (e.g., perfusate) to be introduced to the tissue chamber 30. In this manner, fluid can be introduced into the tissue chamber 30 as desired by an operator of the self-purging preservation apparatus. For example, in some embodiments, a desired amount of perfusate is introduced into the tissue chamber 30 via the port 34, such as before disposing the tissue T in the tissue chamber 30 and/or while the tissue T is received in the tissue chamber. In some embodiments, the fill port 34 is a unidirectional port, and thus is configured to prevent the flow of fluid from the tissue chamber 30 to an area external to the tissue chamber through the port. In some embodiments, the fill port 34 includes a luer lock. The tissue chamber 30 may be of any suitable volume necessary for receiving the tissue T and a requisite amount of fluid for maintaining viability of the tissue T. In one embodiment, for example, the volume of the tissue chamber 30 is approximately 2 liters.

The tissue chamber 30 is formed by a canister 32 and a bottom portion 19 of the pumping chamber 14. In a similar manner as described above with respect to the membrane 20, an upper portion of the tissue chamber (defined by the bottom portion 19 of the pumping chamber 14) can be inclined from the first side 22 towards the second side 24 of the self-purging preservation apparatus. In this manner, as described in more detail below, a rising fluid in the tissue chamber 30 will be directed by the inclined upper portion of the tissue chamber towards a valve 36 disposed at a highest portion of the tissue chamber. The valve 36 is configured to permit a fluid to flow from the tissue chamber 30 to the pumping chamber 14. The valve 36 is configured to prevent flow of a fluid from the pumping chamber 14 to the tissue chamber. The valve 36 can be any suitable valve for permitting unidirectional flow of the fluid, including, for example, a ball check valve.

The combination of fill port 34, valve 36, and vent port 38 allow the apparatus to be quickly and reliably filled with preservation fluid during an organ harvest or some other tissue storage procedure. Once the tissue T has been loaded, i.e., with a coupler, sling, or basket as described elsewhere, the pumping chamber 14 can be affixed to the tissue chamber 30, providing an airtight seal. A tube to a reservoir of perfusion fluid can be connected to the fill port 34 allowing the tissue chamber to be filled directly from the outside. Because of the incline of the bottom portion 19 of the pumping chamber 14, any trapped fluids that are less dense than the preservation fluid (e.g., air) will travel along the bottom portion 19 and move to the pumping chamber 14 via valve 36, that can be a one-way check valve. With the addition of more preservation fluid from the fill port 34, the perfusion fluid will also move from the tissue chamber 30 to the pumping chamber 14, driving any less dense fluid to higher points in the pumping chamber 14. When the pumping chamber 14 is finally filled with preservation fluid, all of the rising fluids will be driven out of the apparatus via vent port 38. Thus, a user can simply fill the apparatus via fill port 34 and know that the apparatus is filled with preservation fluid and that all rising fluids (i.e., air) has been driven out of the apparatus when preservation fluid first appears at vent port 38. Additionally, this design conserves preservation fluid ($400/L) when compared to competing designs that immerse an organ in an over-filled preservation fluid, attempting to drive air out of the system as the lid is placed on the device.

The canister 32 can be constructed of any durable materials that are suitable for use with a medical device. For example, it can be constructed of stainless steel. In other embodiments, because it is beneficial to be able to view the contents directly, the lid 6 and storage vessel may be constructed of medical acrylic (e.g., PMMA) or another clear medical polymer. In some embodiments, the canister 32 is constructed of a material that permits an operator of the self-purging preservation apparatus 10 to view at least one of the tissue T or the perfusate received in the tissue chamber 30. For example, in some embodiments, the canister 32 is substantially transparent. In another example, in some embodiments, the canister 32 is substantially translucent. The tissue chamber 30 can be of any suitable shape and/or size. For example, in some embodiments, the tissue chamber 30 can have a perimeter that is substantially oblong, oval, round, square, rectangular, cylindrical, or another suitable shape. Additionally, the self-purging preservation apparatus should be constructed of materials that conduct heat so that the sample within the container is adequately cooled by the cooling media (see discussion below).

It is additionally beneficial for the storage vessel 2, lid without a pumping chamber 6, and adapter to be sterilizable, i.e., made of a material that can be sterilized by steam (autoclave) or with UV irradiation, or another form of sterilization. Sterilization will prevent tissues from becoming infected with viruses, bacteria, etc., during transport. In a typical embodiment the self-purging preservation apparatus will be delivered in a sterile condition and sealed in sterile packaging. In some embodiments, the self-purging preservation apparatus will be sterilized after use prior to reuse, for example at a hospital. In other embodiments, the self-purging preservation apparatus will be disposable.

In use, the tissue T is coupled to the adapter 26. The pumping chamber 14 is coupled to the canister 32 such that the tissue T is received in the tissue chamber 30. In some embodiments, the pumping chamber 14 and the canister 32 are coupled such that the tissue chamber 30 is hermetically sealed. A desired amount of perfusate is introduced into the tissue chamber 30 via the port 34. The tissue chamber 30 can be filled with the perfusate such that the perfusate volume rises to the highest portion of the tissue chamber. The tissue chamber 30 can be filled with an additional amount of perfusate such that the perfusate flows from the tissue chamber 30 through the valve 36 into the second portion 18 of the pumping chamber 14. The tissue chamber 30 can continue to be filled with additional perfusate until all atmospheric gas that initially filled the second portion 18 of the pumping chamber 14 rises along the inclined membrane 20 and escapes through the port 38. Because the gas will be expelled from the pumping chamber 14 via the port 38 before any excess perfusate is expelled (due to gas being lighter, and thus more easily expelled, than liquid), an operator of the self-purging preservation apparatus 10 can determine that substantially all excess gas has been expelled from the pumping chamber when excess perfusate is released via the port. As such, the self-purging preservation apparatus 10 can be characterized as self-purging. When perfusate begins to flow out of the port 38, the self-purging preservation apparatus 10 is in a "purged" state (i.e., all atmospheric gas initially within the tissue chamber 30 and the second portion 18 of the pumping chamber 14 has been replaced by perfusate). When the purged state is reached, the operator can close both ports 34 and 38, preparing the self-purging preservation apparatus 10 for operation.

Oxygen (or another suitable fluid, e.g., dry air) is introduced into the first portion 16 of the pumping chamber 14 via the valve 12. A positive pressure generated by the introduction of oxygen into the pumping chamber 14 causes the oxygen to be diffused through the semi-permeable membrane 20 into the second portion 18 of the pumping chamber. Because oxygen is a gas, the oxygen expands to substantially fill the first portion 16 of the pumping chamber 14. As such, substantially the entire surface area of the membrane 20 between the first portion 16 and the second portion 18 of the pumping chamber 14 is used to diffuse the oxygen. The oxygen is diffused through the membrane 20 into the perfusate received in the second portion 18 of the pumping chamber 14, thereby oxygenating the perfusate.

In the presence of the positive pressure, the oxygenated perfusate is moved from the second portion 18 of the pumping chamber 14 into the tissue T via the adapter 26. For example, the positive pressure can cause the perfusate to move from the pumping chamber 14 through the lumen of the adapter 26 into the vessel of the tissue T. The positive pressure is also configured to help move the perfusate through the tissue T such that the tissue T is perfused with oxygenated perfusate.

After the perfusate is perfused through the tissue T, the perfusate is received in the tissue chamber 30. In this manner, the perfusate that has been perfused through the tissue T is combined with perfusate previously disposed in the tissue chamber 30. In some embodiments, the volume of perfusate received from the tissue T following perfusion combined with the volume of perfusate previously disposed in the tissue chamber 30 exceeds a volume (e.g., a maximum fluid capacity) of the tissue chamber 30. A portion of the tissue chamber 30 is flexible and expands to accept this excess volume. The valve 12 can then allow oxygen to vent from the first portion 16 of the pumping chamber 14, thus, reducing the pressure in the pumping chamber 14. As the pressure in the pumping chamber 14 drops, the flexible portion of the tissue chamber 30 relaxes, and the excess perfusate is moved through the valve 36 into the pumping chamber 14. The cycle of oxygenating perfusate and perfusing the tissue T with the oxygenated perfusate can be repeated as desired.

A variety of preservation solutions can be used with the invention. This includes approved preservation solutions, such as Histidine-Tryptophan-Ketoglutarate (HTK) (e.g., HTK Custodial™) and Celsior™ solutions for the preservation of hearts and cardiac tissues, and University of Wisconsin Solution (Viaspan™) and MPS-1 for the preservation of kidney and kidney tissues. Other preservation solutions, including non-approved solutions, and off-label applications of approved solutions can be used with the devices of the invention. A detailed listing of the properties of various preservation solutions, including Collins, Euro-Collins, phosphate buffered sucrose (PBS), University of Wisconsin (UW) (e.g., Belzer Machine Preservation Solution (MPS)), histidine-tryptophan-ketoglutarate (HTK), hypertonic citrate, hydroxyethyl starch, and Celsior™, can be found at FIGS. 41 and 42. Additional details of these solutions can be found at t'Hart et al. "New Solutions in Organ Preservation," *Transplantation Reviews* 2006, vol. 16, pp. 131-141 (2006), which is incorporated by reference in its entirety.

A self-purging preservation apparatus 100 according to an embodiment is illustrated in FIGS. 2-7. The self-purging preservation apparatus 100 is configured to oxygenate a perfusate and to perfuse a tissue for extracorporeal preservation of the tissue. The self-purging preservation apparatus 100 includes a lid assembly 110, a canister 190, and a coupling mechanism 250.

Figure 2:
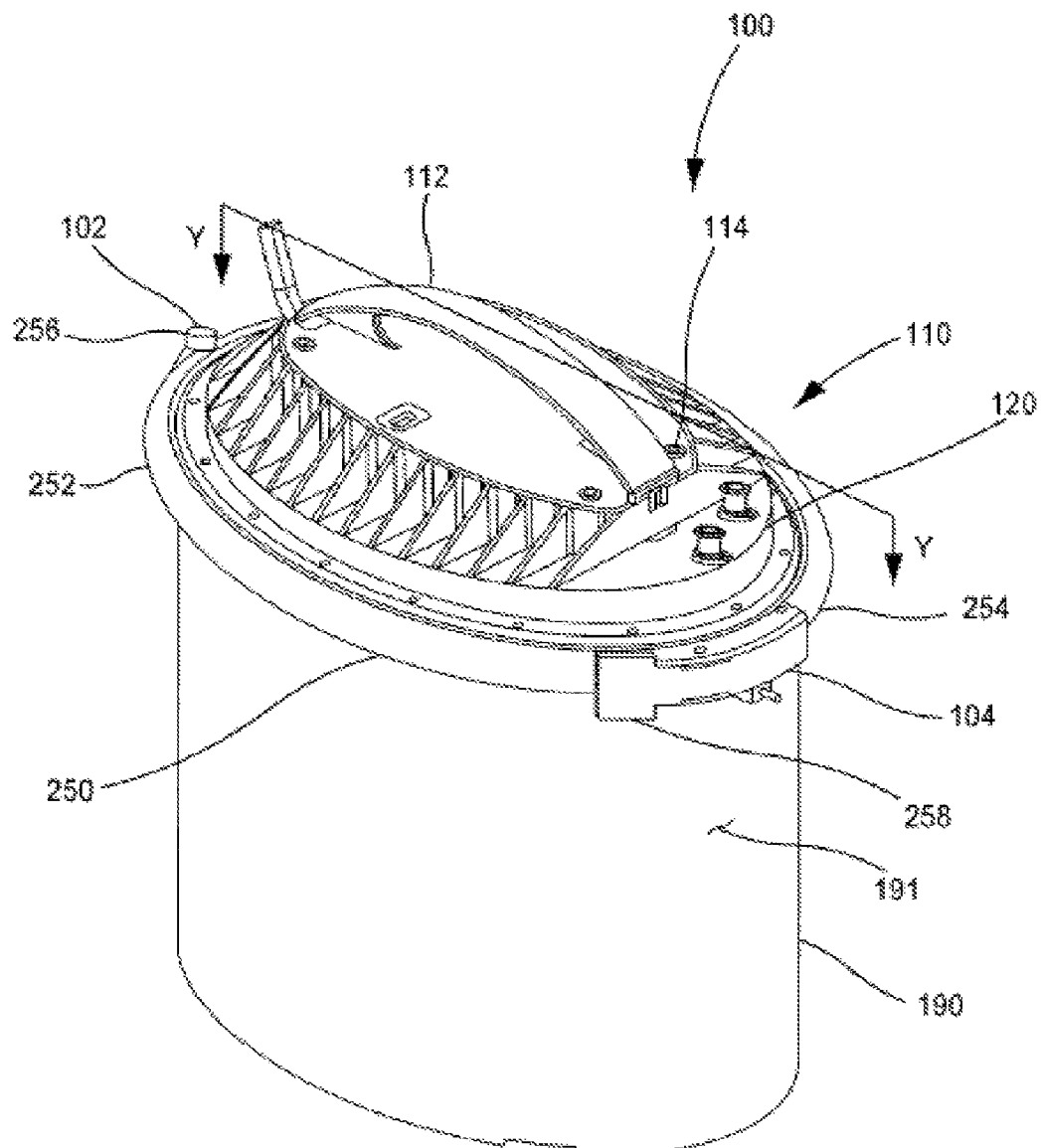
FIG. 2 is a perspective view of a self-purging preservation apparatus according to an embodiment.
Figure 3:
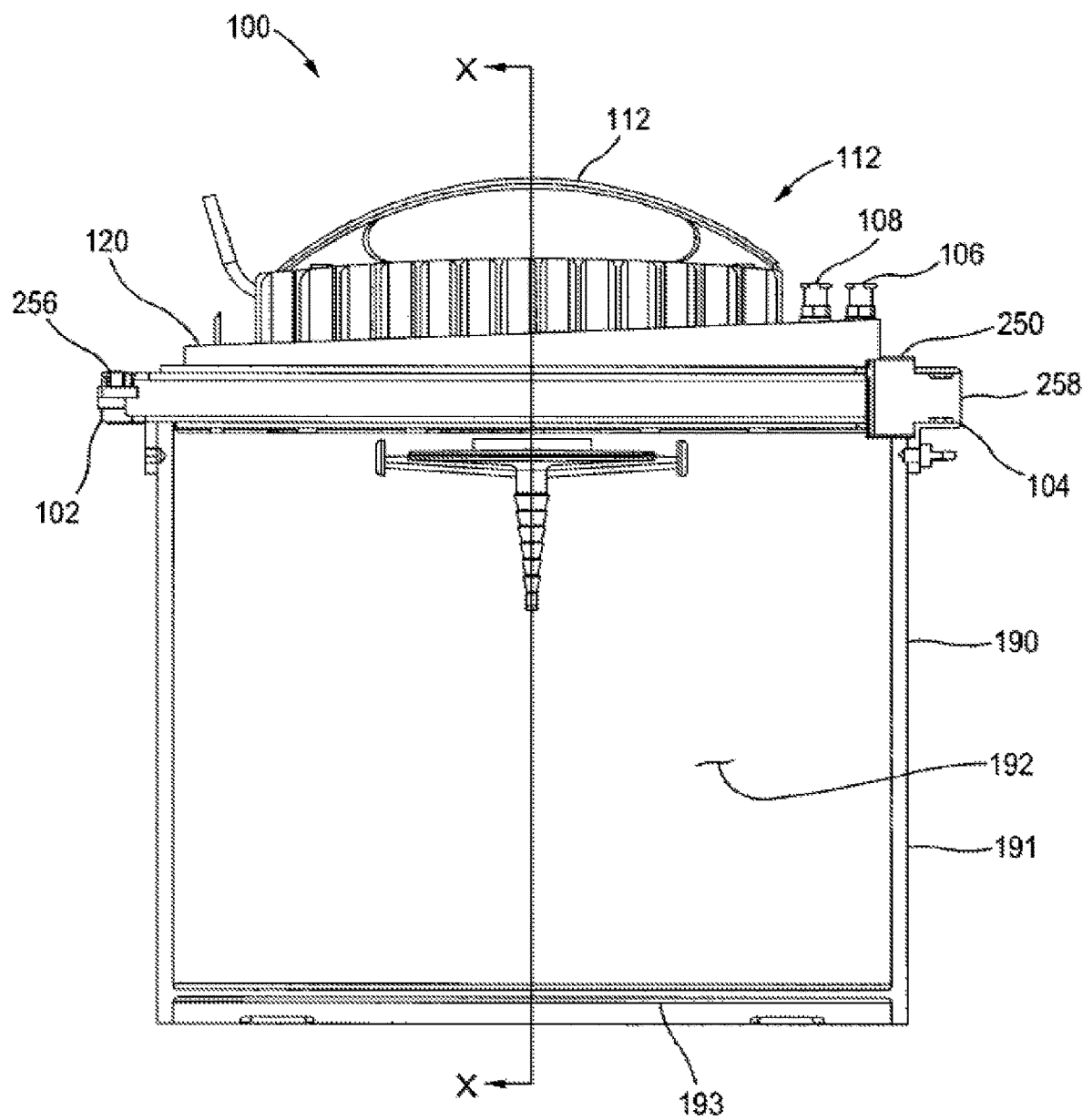
FIG. 3 is a side view of the self-purging preservation apparatus of FIG. 2.

The lid assembly 110 is configured to facilitate transportability of the self-purging preservation apparatus. The lid assembly 110 includes a handle 112 and a lid 120. The handle 112 is configured to be grasped, e.g., by a hand of a person transporting the self-purging preservation apparatus 100. The handle 112 is coupled to the lid 120. The handle 112 can be coupled to the lid 120 using any suitable mechanism for coupling. For example, the handle 112 can be coupled to the lid 120 with at least one screw (e.g., screw 114 as shown in FIG. 2), an adhesive, a hook and loop fastener, mating recesses, or the like, or any combination of the foregoing. An upper portion 122 of the lid 120 defines a chamber 124 configured to receive components of a pneumatic system 200 and a control system 500, each of which is described in more detail below. A bottom portion 116 of the handle 112 is configured to substantially enclose a top of the chamber 124 defined by the lid 120.

The lid assembly 110 defines a pumping chamber 125 configured to receive a gas, such as oxygen, from the pneumatic system 200, to facilitate diffusion of the oxygen into a perfusate (not shown) and to facilitate movement of the oxygenated perfusate into a tissue (not shown). Although the self-purging preservation apparatus 100 is described herein as being configured for use with oxygen, any suitable gas may be used with self-purging preservation apparatus 100 instead of or in addition to oxygen. A top of the pumping chamber 125 is formed by a lower portion 128 of the lid 120. A bottom of the pumping chamber 125 is formed by an upper surface 134 of a base 132 of the lid assembly 110.

Figure 6:
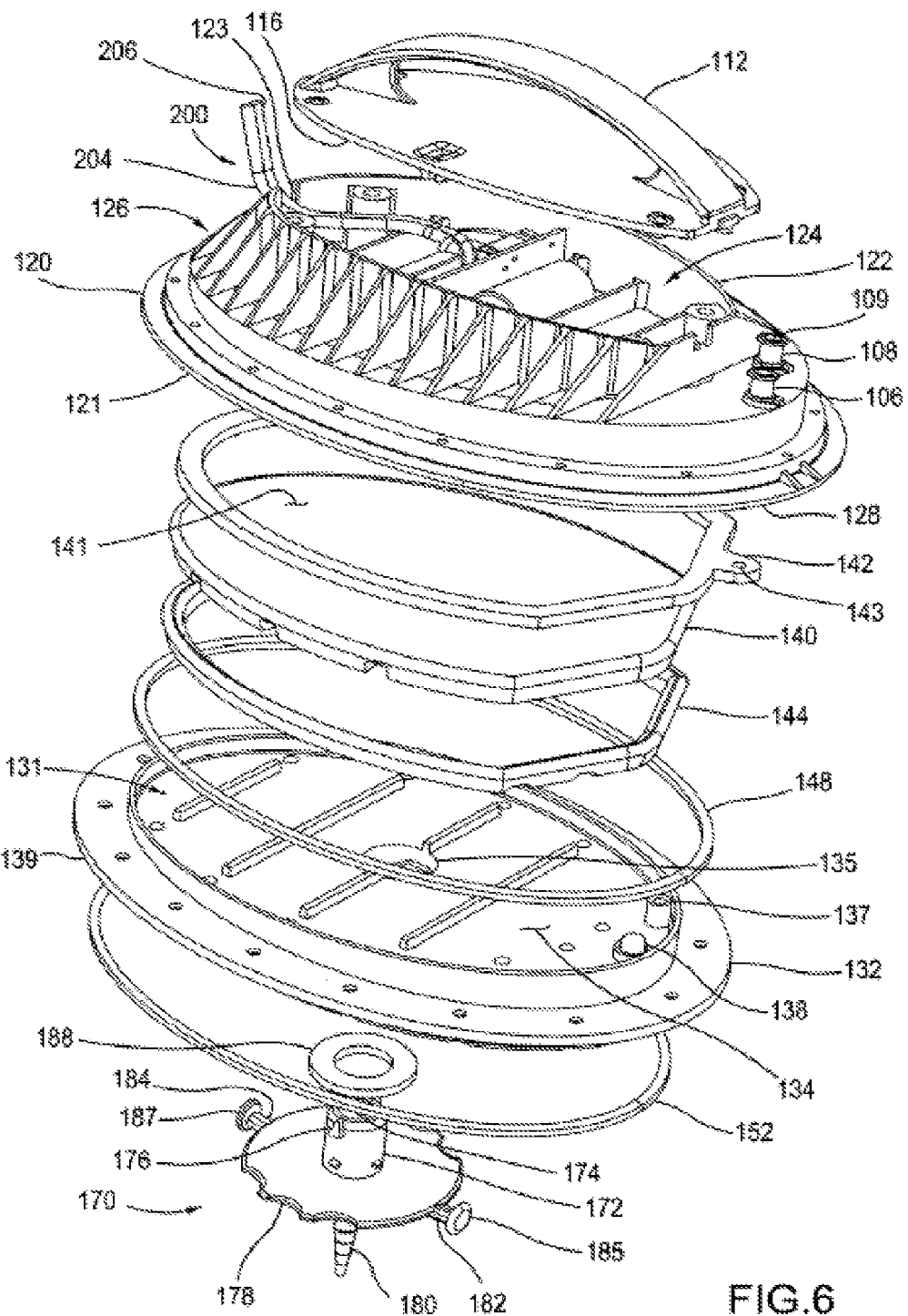
FIG. 6 is an exploded perspective view of a lid assembly of the self-purging preservation apparatus of FIG. 2.

As illustrated in an exploded perspective view in FIG. 6, the lid assembly 110 includes a first gasket 142, a membrane 140, and a membrane frame 144. The membrane 144 is disposed within the pumping chamber 125. The first gasket 142 is disposed between the membrane 140 and the lid 120 such that the first gasket is engaged with an upper surface 141 of the membrane 140 and the lower portion 128 of the lid. The first gasket 142 is configured to seal a perimeter of a first portion 127 of the pumping chamber 125 formed between the lower portion 128 of the lid 120 and the upper surface 141 of the membrane 140. In other words, the first gasket 142 is configured to substantially prevent lateral escape of the oxygen from the first portion 127 of the pumping chamber 125 to a different portion of the pumping chamber. In the embodiment illustrated in FIG. 6, the first gasket 142 has a perimeter substantially similar in shape to a perimeter defined by the membrane 140 (e.g., when the membrane is disposed on the membrane frame 148). In other embodiments, however, a first gasket can have another suitable shape for sealing a first portion of a pumping chamber configured to receive oxygen from a pneumatic system.

The first gasket 142 can be constructed of any suitable material. In some embodiments, for example, the first gasket 142 is constructed of silicone, an elastomer, or the like. The first gasket 142 can have any suitable thickness. For example, in some embodiments, the first gasket 142 has a thickness within a range of about 0.1 inches to about 0.15 inches. More specifically, in some embodiments, the first gasket 142 has a thickness of about 0.125 inches. The first gasket 142 can have any suitable level of compression configured to maintain the seal about the first portion 142 of the pumping chamber 125 when the components of the lid assembly 110 are assembled. For example, in some embodiments, the first gasket 142 is configured to be compressed by about 20 percent. In some embodiments, the first gasket 142 can provide a leak-proof seal under operating pressures up to 5 pounds per square inch (psi).

Figure 5:
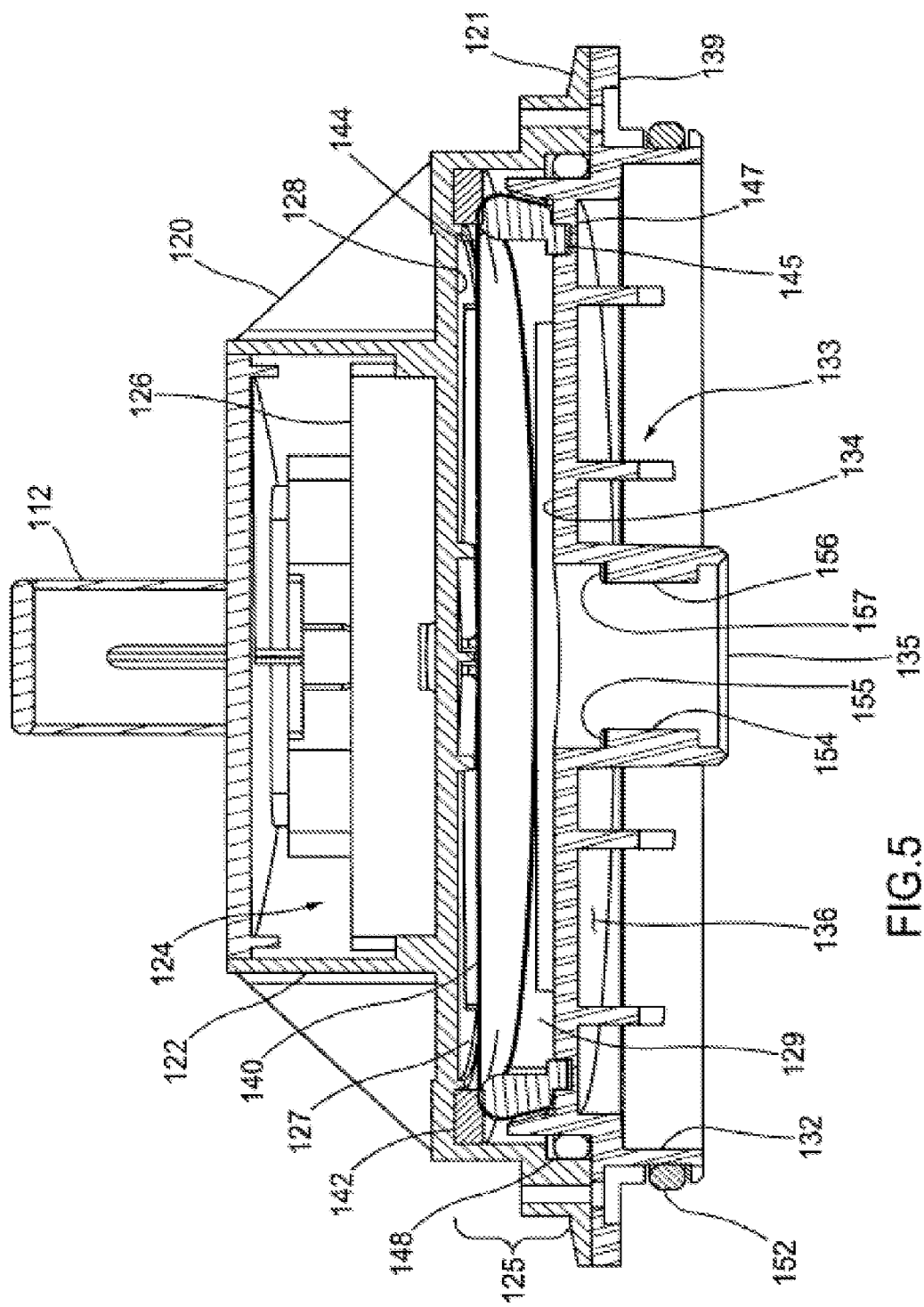
FIG. 5 is a cross-sectional view of a lid assembly of the self-purging preservation apparatus of FIG. 2 taken along line X-X (shown in FIG. 3).

The membrane 140 is configured to permit diffusion of the gas from the first portion 127 of the pumping chamber 125 through the membrane to a second portion 129 of the pumping chamber, and vice versa. The membrane 140 is configured to substantially prevent a liquid (e.g., the perfusate) from passing through the membrane. In this manner, the membrane 140 can be characterized as being semi-permeable. A membrane frame 144 is configured to support the membrane 140 (e.g., during the oxygenation and perfusing of the tissue). The membrane frame 144 can be a substantially ring-like structure with an opening at its center. As shown in FIG. 5, at least a portion of the membrane 140 is disposed (e.g., wrapped) about at least a portion of the membrane frame 144. In some embodiments, the membrane 140 is stretched when it is disposed on the membrane frame 144. The membrane 140 is disposed about a lower edge of the membrane frame 144 such that the membrane 140 is engaged with a series of protrusions (e.g., protrusion 145 shown in FIG. 5) configured to help retain the membrane with respect to the membrane frame 144. At least a portion of the series of protrusions on the lower edge of the membrane frame 144 are configured to be received in a recess 147 defined by the upper surface 134 of the base 132. As such, the membrane 140 is engaged between the membrane frame 144 and the base 132, which facilitates retention of the membrane with respect to the membrane frame. In some embodiments, the first gasket 142 also helps to maintain the membrane 140 with respect to the membrane frame 144 because the first gasket is compressed against the membrane.

Figure 4:
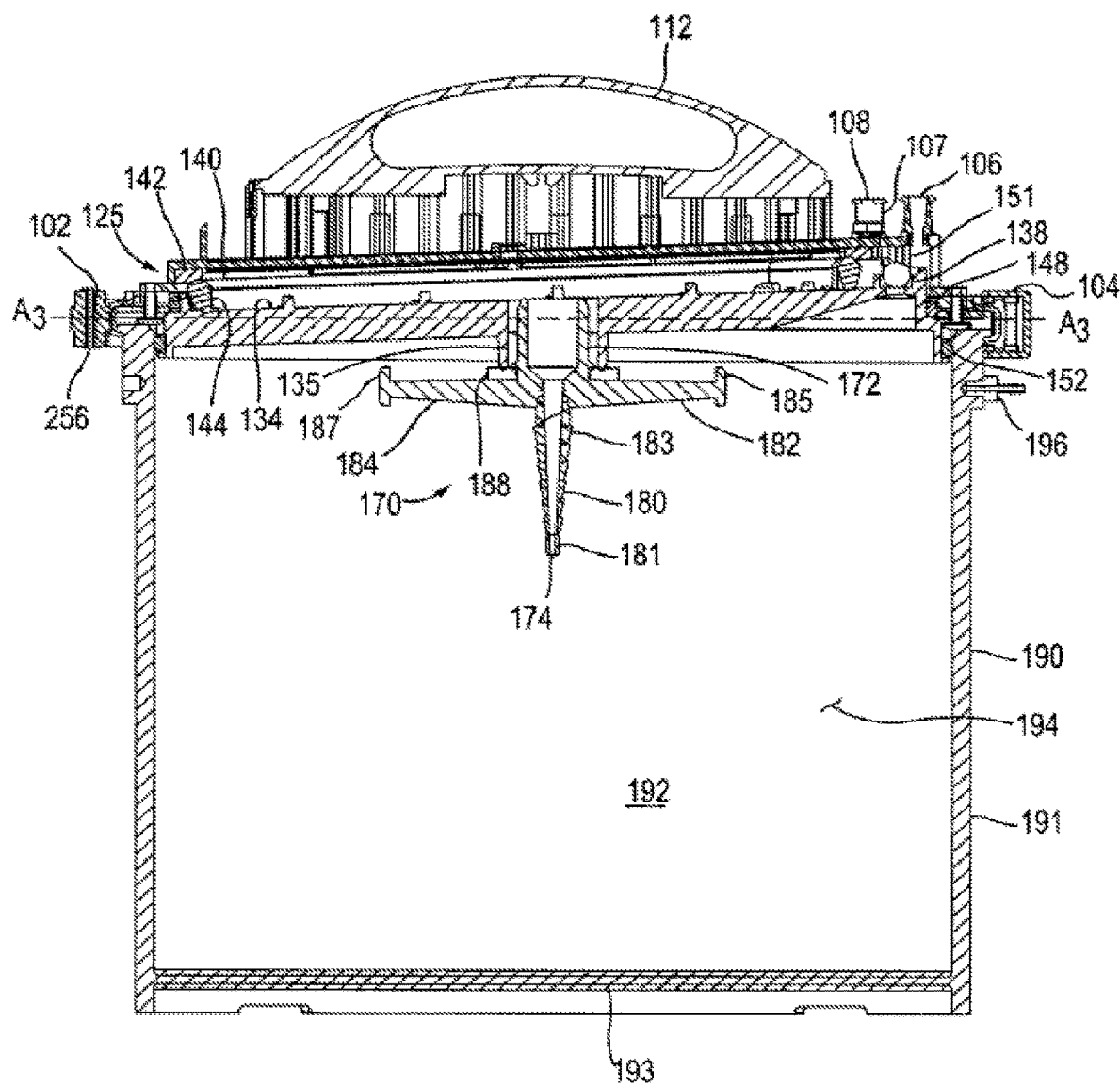
FIG. 4 is a cross-sectional view of the self-purging preservation apparatus of FIG. 2 taken along line Y-Y, with a portion of a pneumatic system removed.

As best illustrated in FIG. 4, the membrane 140 is disposed within the pumping chamber 125 at an angle with respect to a horizontal axis A3. In this manner, the membrane 140 is configured to facilitate the movement of fluid towards a highest portion of the pumping chamber 125, as described in more detail herein.

The membrane 140 can be of any suitable size. For example, in some embodiments, the upper surface 141 of the membrane 140 can be about 15 to about 20 square inches. More specifically, in some embodiments, the upper surface 141 of the membrane 140 can be about 19 square inches. In another example, the membrane 140 can have any suitable thickness. In some embodiments, for example, the membrane 140 is about 0.005 inches to about 0.010 inches thick. More specifically, in some embodiments, the membrane is about 0.0075 inches thick. The membrane 140 can be constructed of any suitable material. For example, in some embodiments, the membrane is constructed of silicone, plastic, or another suitable material. In some embodiments, the membrane is flexible. As illustrated in FIG. 6, the membrane 140 can be substantially seamless. In this manner, the membrane 140 is configured to be more resistant to being torn or otherwise damaged in the presence of a flexural stress caused by a change pressure in the pumping chamber due to the inflow and/or release of oxygen.

The lid 120 includes a purge port 106 disposed at the highest portion of the second portion 129 of the pumping chamber 125, as shown in FIG. 4. In some embodiments, the port 106 is disposed at the highest portion of the pumping chamber 125 as a whole. In other words, the highest portion of the second portion 129 of the pumping chamber 125 can be the highest portion of the pumping chamber 125. The purge port 106 is configured to permit movement of a fluid from the pumping chamber 125 to an area external to the self-purging preservation apparatus 100. The purge port 106 can be similar in many respects to a port described herein (e.g., port 38, described above, and/or purge ports 306, 706, described below). The purge port 106 can be any suitable mechanism for permitting movement of the fluid from the pumping chamber 125 into the atmosphere external to the self-purging preservation apparatus 100, including, but not limited to, a luer lock fitting. The purge port 106 can include a cap (not shown) coupled to the port via a retaining strap.

In some embodiments, the lid 120 is transparent, either in its entirety or in part (e.g. in the vicinity of the purge port 106). This permits a user to readily view a fluid therein (e.g., any gas bubbles) and to confirm completion of purging of excess fluid (e.g., the gas bubbles).

Referring to FIG. 4, and as noted above, the upper surface 134 of the base 132 forms the bottom portion of the pumping chamber 125. The upper surface 134 of the base 132 is inclined from a first end 102 of the self-purging preservation apparatus 100 to a second end 104 of the self-purging preservation apparatus. Said another way, the upper surface 134 lies along a plane having an axis different than the horizontal axis A3. Because each of the first gasket 142, the membrane 140, and the membrane frame 144 are disposed on the upper surface 134 of the base 132, each of the first gasket, the membrane, and the membrane frame are similarly inclined from the first end 102 of the self-purging preservation apparatus 100 towards the second end 104 of the self-purging preservation apparatus. In this manner, the base 132 is configured to facilitate movement of a fluid towards the highest portion of the pumping chamber 125.

The angle of incline of these components may be of any suitable value to allow fluid (e.g., gas bubbles, excess liquid) to flow towards the purge port 106 and exit the pumping chamber 125. In some embodiments, the angle of incline is approximately in the range of 1°-10°, in the range of 2°-6°, in the range of 2.5°-5°, in the range of 4°-5°, or any angle of incline in the range of 1 (e.g., approximately 1°, 2°, 3°, 4°, 5°, 6°, 7°, 8°, 9°, 10°).

As illustrated in FIG. 4, a valve 138 is disposed at approximately the highest portion of the lower surface 136 of the base 132. The valve 138 is moveable between an open configuration and a closed configuration. In its open configuration, the valve 138 is configured to permit movement of a fluid from a tissue chamber 192, which is defined by the canister 190 and a lower surface 136 of the lid assembly 110, to the pumping chamber 125 via the valve. Specifically, the valve 138 is configured to permit fluid to move from the tissue chamber 192 into the second portion 129 of the pumping chamber 114. In this manner, an excess amount of fluid within the tissue chamber 192 can overflow through the valve 138 and into the pumping chamber 125. In its closed configuration, the valve 138 is configured to substantially prevent movement of a fluid from the pumping chamber 125 to the tissue chamber 192 via the valve. The valve 138 is moved from its closed configuration to its open configuration when a pressure in the tissue chamber 192 is greater than a pressure in the pumping chamber 125. In some embodiments, the valve 138 is moved from its open position to its closed position when a pressure in the pumping chamber 125 is greater than a pressure in the tissue chamber 192. The valve 138 can be biased towards its closed configuration. In some embodiments, one or more additional valves (not shown) are disposed at other locations of the base 132. In some embodiments, an additional valve (not shown) is located at approximately the lowest portion of the lower surface 136 of the base 132.

As illustrated in FIGS. 4 and 6, in some embodiments, the valve 138 is a ball check valve. In its closed configuration, a spherical ball of the valve 138 is disposed on a seat of the valve. In its open configuration, the ball is lifted off of the seat of the valve 138. The ball of the valve 138 has a near neutral buoyancy. As such, the ball of the valve 138 will neither sink nor rise merely because it is in the presence of a fluid (e.g., the perfusate, oxygen, or another fluid). The ball of the valve 138 is configured to rise off of the seat of the valve when the pressure in the tissue chamber 192 is greater than the pressure in the pumping chamber 125. In some embodiments, a protrusion 151 of the lid 120 is extended downwardly over the valve 138 to prevent the ball from rising too high above the seat such that the ball could be laterally displaced with respect to the seat. In some embodiments, the ball of the valve 138 is configured to return to the seat of the valve when the pressure in the pumping chamber is greater than the pressure in the tissue chamber. In some embodiments, the ball of the valve 138 is biased towards the seat of the valve by a spring (not shown) extended from the lid 120. The seat of the valve 138 can be conically tapered to guide the ball into the seat and to facilitate formation of a positive seal when stopping flow of fluid from the pumping chamber 125 to the tissue chamber 192.

The base 132 is coupled to the lid 120. In some embodiments, a rim 139 of the base 132 and a rim 121 of the lid 120 are coupled together, e.g., about a perimeter of the pumping chamber 125. The base 132 and the lid 120 can be coupled using any suitable mechanism for coupling including, but not limited to, a plurality of screws, an adhesive, a glue, a weld, another suitable coupling mechanism, or any combination of the foregoing. A gasket 148 is disposed between the base 132 and the lid 120. The gasket 148 is configured to seal an engagement of the base 132 and the lid 120 to substantially prevent fluid in the pumping chamber 125 from leaking therebetween. In some embodiments, the gasket 148 is an O-ring.

The base 132 defines a lumen 135 configured to be in fluid communication with a lumen 174 of an tissue adapter 170, described in more detail below. The base 132 is configured to permit oxygenated perfusate to move from the pumping chamber 125 through its lumen 135 into the lumen 174 of the tissue adapter 170 towards the tissue chamber 192. In this manner, the lumen 135 of the base 132 is configured to help fluidically couple the pumping chamber 125 and the tissue chamber 192.

The tissue adapter 170 is configured to substantially retain the tissue with respect to the self-purging preservation apparatus 100. The tissue adapter 170 can be similar in many respects to an adapter described herein (e.g., adapter 26, described above, and/or adapter 770, described below). The tissue adapter 170 includes a handle portion 178, an upper portion 172, and a protrusion 180, and defines the lumen 174 extended therethrough. The upper portion 172 of the tissue adapter 170 is extended from a first side of the handle portion 178. The protrusion 180 of the tissue adapter 170 is extended from a second side of the handle portion 178 different than the first side of the handle portion. At least a portion of the protrusion 180 is configured to be inserted into the tissue. More specifically, at least a portion of the protrusion 180 is configured to be inserted into a vessel (e.g., an artery, a vein, or the like) of the tissue. In some embodiments, the protrusion 180 is configured to be coupled to the tissue via an intervening structure, such as silastic or other tubing.

As illustrated in FIG. 4, at least a portion of the protrusion 180 includes a series of tapered steps such that a distal end 181 of the protrusion is narrower than a proximal end 183 of the protrusion. In this manner, the protrusion 180 is configured to be inserted into a range of vessel sizes. For example, the protrusion 180 can be configured to be received in a bodily vessel having a diameter within the range of about 3 millimeters to about 8 millimeters. In this manner, the protrusion 180 is configured to deliver the fluid (e.g., the oxygenated perfusate) from the pumping chamber 125 to the vessel of the tissue via the lumen 174 defined by the tissue adapter 170. The vessel of the tissue can be sutured to the protrusion 180 of the adapter 170.

The tissue adapter 170 includes a first arm 182 having a first end portion 185 and a second arm 184 having a second end portion 187. The first and second arms 182, 184 are configured to facilitate retention of the tissue with respect to the tissue adapter 170. A retention mechanism (not shown) is configured to be attached, coupled, or otherwise disposed about each of the first and second arms 182, 184. The retention mechanism can be any suitable retention mechanism described above with respect to the self-purging preservation apparatus 10, including, for example, a net, a cage, a sling, or the like. A middle portion of the retention mechanism is configured to be disposed about at least a portion of the tissue coupled to the protrusion 180 of the adapter 170. End portions of the retention mechanism are configured to be disposed about each of the first and second arms 182, 184 of the tissue adapter 170. The first end portion 185 of the first arm 182 and the second end portion 187 of the second arm 184 are each configured to facilitate retention of the end portions of the retention mechanism with respect to the first and second arms, respectively. For example, as shown in FIG. 4, each of the first and second end portions 185, 187 of the first and second arms 182, 184, respectively, defines a shoulder portion configured to help prevent the end portions of the retention mechanism from being inadvertently removed from the first or second atm, respectively.

The upper portion 172 of the tissue adapter 170 is configured to couple the tissue adapter to the base 132. The upper portion 172 of the tissue adapter is configured to be received by the lumen 135 defined by the base. The upper portion 172 includes a first projection 176 and a second projection (not shown) spaced apart from the first projection. The projections 176 of the tissue adapter 170 are configured to be received by the lumen 135 of the base 132 in opposing spaces between a first protrusion 154 and a second protrusion 156 (shown in FIG. 5) disposed within the lumen of the base. Once the upper portion 172 is received in the lumen 135 of the base 132, the tissue adapter 170 can be rotated approximately ninety degrees such that its first projection 176 and its second projection sit on a shoulder 155, 157 defined by the protrusions 154, 156 of the base, respectively. The tissue adapter 170 can be rotated in either a clockwise or a counterclockwise direction to align its projections with the shoulders of the protrusions of the base 132. Similarly, the tissue adapter 170 can be rotated in either the clockwise or the counterclockwise direction to unalign its projections with the shoulders of the protrusions of the base 132, such as for decoupling of the adapter from the base. Said another way, the tissue adapter 170 can be configured to be coupled to the base 132 with a bayonet joint. The handle portion 178 is configured to facilitate coupling and decoupling of the tissue adapter 170 and the base 132. For example, the handle portion 178 is configured to be grasped by a hand of an operator of the self-purging preservation apparatus 100. As shown in FIG. 6, the handle portion 178 is substantially disc-shaped, and includes a series of recesses configured to facilitate grasping the handle portion with the operator's hand.

A gasket 188 is disposed about the upper portion 172 of the tissue adapter 170 between the handle portion 178 of the adapter and the base 132. The gasket 188 is configured to substantially prevent a fluid from flowing between the pumping chamber 125 and the tissue chamber 192 within a channel formed between an outer surface of the upper portion 172 of the tissue adapter 170 and an inner surface of the lumen 135 of the base 132. In some embodiments, the gasket 188 is compressed between the tissue adapter 170 and the base 132 when the tissue adapter is coupled to the base.

In some embodiments, at least a portion of the lid assembly 110 is configured to minimize flexure of the portion of the lid assembly, such as may occur in the presence of a positive pressure (or pulse wave) caused by introduction of oxygen into the pumping chamber 125 and/or of oxygenated perfusate into the tissue chamber 192. For example, as illustrated in FIG. 6, the upper portion 122 of the lid 120 includes a plurality of ribs 126 configured to minimize flexure of the lid 120 when oxygen is pumped through the pumping chamber 125. In other words, the plurality of ribs 126 structurally reinforces the lid 120 to help prevent the lid 120 from flexing. The plurality of ribs 126 are extended from a top surface of the lid 120 in a substantially parallel configuration. In another example, the lower portion 128 of the lid 120 can include a plurality of ribs (not shown) configured to reinforce the top of the pumping chamber 125 to help prevent flexure of the top of the pumping chamber 125 during pumping of oxygen through the lid assembly 110. In yet another example, the base 132 is configured to substantially minimize flexure of the base, such as may occur in the presence of a positive pressure caused by the introduction of oxygen into the pumping chamber 125 and/or of oxygenated perfusate into the tissue chamber 192. As illustrated in FIG. 6, the base 132 includes a plurality of ribs 131 extended from its upper surface 134. As illustrated in FIG. 5, the base 132 includes a plurality of ribs 133 extended from its lower surface 136. Each of the plurality of ribs 131, 133 is configured to reinforce the base 132, which helps to minimize flexure of the base.

The lid assembly 110 includes a fill port 108 configured to permit introduction of a fluid (e.g., the perfusate) into the tissue chamber 192 (e.g., when the lid assembly is coupled to the canister 190). The fill port 108 can be similar in many respects another port described herein (e.g., port 34, described above, and/or port 708, described below). In the embodiment illustrated in FIG. 4 and FIG. 6, the fill port 108 is formed by a fitting 107 coupled to the lid 120 and that defines a lumen 109 in fluidic communication with a lumen 143 in the first gasket 142, which lumen 143 is in fluidic communication with a lumen 137 defined by the base 132, which lumen 137 is in fluidic communication with the tissue chamber 192. The fitting 107 can be any suitable fitting, including, but not limited to, a luer lock fitting. The fill port 108 can include a cap (not shown) removably coupled to the port via a retaining strap. The cap can help prevent inadvertent movement of fluid, contaminants, or the like through the fill port 108.

The lid assembly 110 is configured to be coupled to the canister 190. The canister 190 can be similar in many respects to a canister described herein (e.g., canister 32, described above, and/or canister 390, 790, 990, described below). The canister includes a wall 191, a floor 193, and a compartment 194 defined on its sides by the wall and on its bottom by the floor. The compartment 194 can form a substantial portion of the tissue chamber 192. As shown in FIG. 4, at least a portion of the lid assembly 110 (e.g., the base 132) is configured to be received in the compartment 194 of the canister 190. A gasket 152 is disposed between the base 132 and an inner surface of the wall 191 of the canister 190. The gasket 152 is configured to seal the opening between the base 132 and the wall 191 of the canister 190 to substantially prevent flow of fluid (e.g., the perfusate) therethrough. The gasket 152 can be any suitable gasket, including, for example, an O-ring. In some embodiments, the canister 190 includes a port 196 disposed on the wall 191 of the canister.

The floor 193 of the canister 190 is configured to flex when a first pressure within the tissue chamber 192 changes to a second pressure within the tissue chamber, the second pressure different than the first pressure. More specifically, in some embodiments, the floor 193 of the canister 190 is configured to flex when a first pressure within the tissue chamber 192 is increased to a second pressure greater than the first pressure. For example, the floor 193 of the canister 190 can be configured to flex in the presence of a positive pressure (or a pulse wave) generated by the pumping of the oxygenated perfusate from the pumping chamber 125 into the tissue chamber 192, as described in more detail below. In some embodiments, the floor 193 of the canister 190 is constructed of a flexible membrane. The floor 193 of the canister 190 can have any suitable thickness. For example, in some embodiments, the floor 193 of the canister 190 has a thickness of about 0.075 to about 0.085 inches. In some embodiments, the floor 193 of the canister 190 is about 0.080 inches thick.

The canister 190 can be configured to enable an operator of the self-purging preservation apparatus 100 to view the tissue when the tissue is sealed within the tissue chamber 192. In some embodiments, for example, at least a portion of the canister 190 (e.g., the wall 191) is constructed of a transparent material. In another example, in some embodiments, at least a portion of the canister 190 (e.g., the wall 191) is constructed of a translucent material. In some embodiments, the canister 190 includes a window (not shown) through which at least a portion of the tissue chamber 192 can be viewed.

As noted above, the coupling mechanism 250 is configured to couple the canister 190 to the lid assembly 110. In the embodiment illustrated in FIGS. 2-4, the coupling mechanism 250 is a substantially C-shaped clamp. The clamp 250 includes a first arm 252 and a second arm 254. The arms 252, 254 are configured to be disposed on opposite sides of the self-purging preservation apparatus 100 about a lower rim of the lid 120 and an upper rim of the canister 190. The arms 252, 254 of the clamp 250 are coupled at the first side 102 of the self-purging preservation apparatus 100 by a hinge 256. The clamp 250 is in an open configuration when the first arm 252 is movable with respect to the second arm 254 (or vice versa). The arms 252, 254 are configured to be coupled at a second side 104 of the self-purging preservation apparatus 100 by a locking lever 258. The clamp 250 is in a closed configuration when its arms 252, 254 are coupled at the second side 104 of the self-purging preservation apparatus 100 by the locking lever 258. In some embodiments, the clamp 250 is configured for a single use. More specifically, the clamp 250 can be configured such that when it is moved from its closed configuration to its open configuration, the clamp is prevented from being returned to its closed configuration. In other words, once an original seal formed by the clamp in its closed configuration is broken by opening the clamp, the clamp can no longer be resealed. In use, the clamp 250 being configured for a single use can help an operator of the self-purging preservation apparatus 100 ensure that tissue being preserved within the self-purging preservation apparatus is free of tampering. In some embodiments, the clamp 250 remains coupled to one of the canister 190 or the lid 120 when the clamp is moved to its open configuration from its closed configuration.

Although the coupling mechanism 250 has been illustrated and described as being a clamp (and a band clamp specifically), in other embodiments, another suitable mechanism for coupling the canister 190 to the lid assembly 110 can be used. For example, the coupling mechanism 250 can be designed as a toggle clamp that is attached to the lid assembly 110. The toggle clamp can be a toggle action clamp that is manually movable between unclamped, center, and over-center (clamped) positions. Any suitable number of toggle clamps may be employed, such as one, two, three, four or more toggle clamps.

As noted above, the self-purging preservation apparatus 100 is configured for controlled delivery of fluid (e.g., oxygen) from an external source (not shown) into the pumping chamber 125 of the lid assembly 110. The external source can be, for example, an oxygen cylinder. In some embodiments, the pneumatic system 200 is configured for controlled venting of fluid (e.g., carbon dioxide) from the pumping chamber 125 to an area external to the self-purging preservation apparatus 100 (e.g., to the atmosphere). The pneumatic system 200 is moveable between a first configuration in which the pneumatic system is delivering fluid to the pumping chamber 125 and a second configuration in which the pneumatic system is venting fluid from the pumping chamber 125. The pneumatic system 200 includes a supply line 204, a vent line 206, a control line 208, a valve 210, a printed circuit board assembly ("PCBA") 214, and a power source 218.

Figure 7:
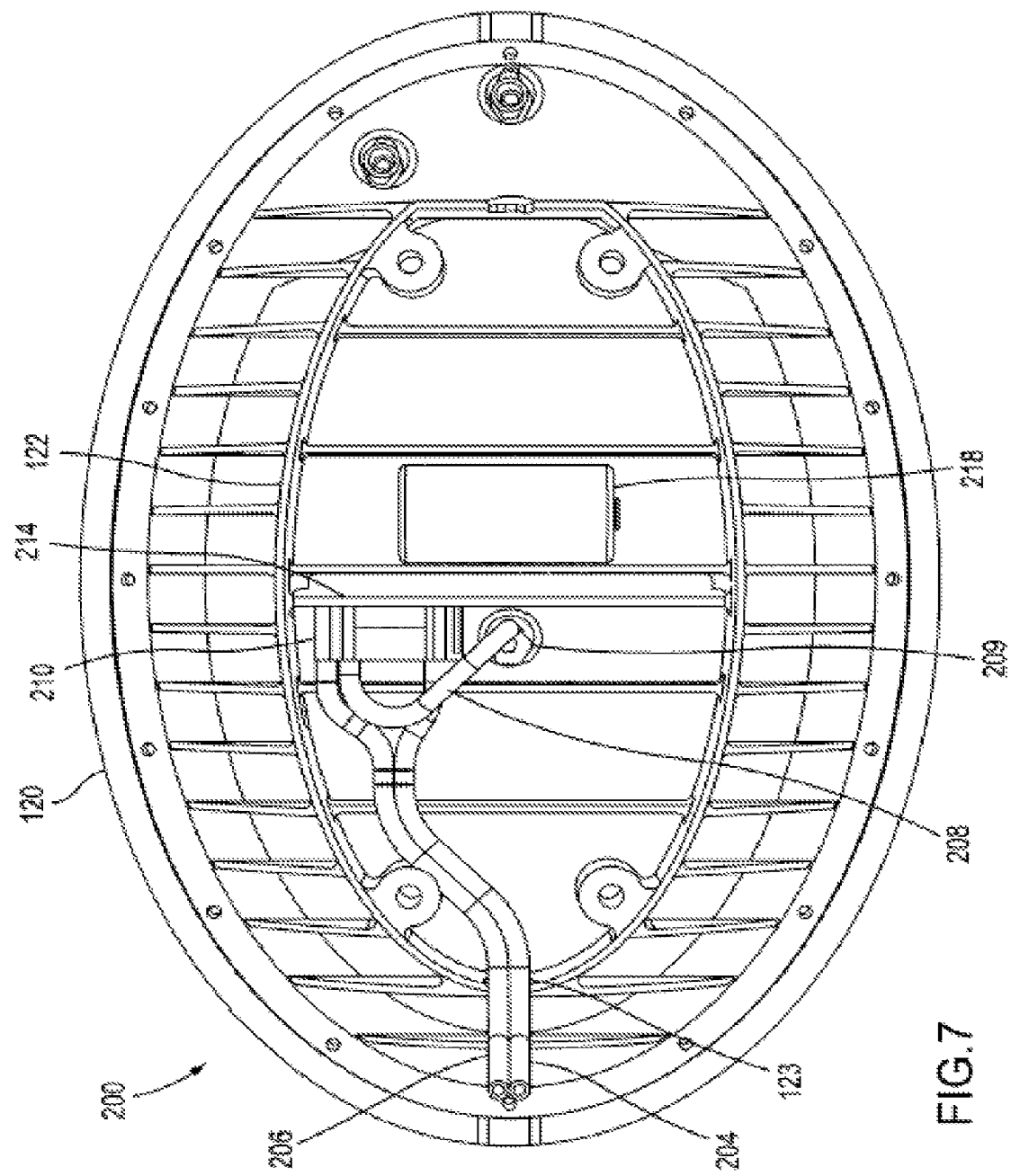
FIG. 7 is a top view of a portion of a lid assembly and a pneumatic system of the self-purging preservation apparatus of FIG. 2.

The supply line 204 is configured to transmit fluid from the external source to the valve 210. A first end of the supply line 204 external to the lid 120 is configured to be coupled to the external source. A second end of the supply line 204 is configured to be coupled to the valve 210. Referring to FIGS. 6 and 7, a portion of the supply line 204 between its first end and its second end is configured to be extended from an area external to the lid 120 through an opening 123 defined by the lid into the chamber 124 defined by the lid. In some embodiments, the supply line 204 is configured to transmit fluid to the valve 210 at a pressure of about 2 pounds per square inch ("p.s.i."), plus or minus ten percent.

The vent line 206 is configured to transmit fluid (e.g., oxygen, carbon dioxide) from the valve 210 to an area external to the chamber 124 of the lid 120. A first end of the vent line 206 is configured to be coupled to the valve 210. In some embodiments, the second end of the vent line 206 is a free end such that the fluid is released into the atmosphere. A portion of the vent line 206 between its first end and its second end is configured to be extended from the valve 210 through the chamber 124 and the opening 123 defined by the lid 120 to the area external to the lid.

The control line 208 is configured to transmit fluid between the valve 210 and the pumping chamber 125 of the lid assembly 110. A first end of the control line 208 is coupled to the valve 210. A second end of the control line 208 is coupled to the pumping chamber 125. In some embodiments, as shown in FIG. 7, the control line 208 is mechanically and fluidically coupled to the pumping chamber 125 by an adapter 209. The adapter 209 can be any suitable mechanism for coupling the control line 208 to the pumping chamber 125. In some embodiments, for example, the adapter 209 includes a male fitting on a first end of the adapter that is configured to be disposed in the second end of the control line 208 and threaded portion on a second end of the adapter configured to be received in a correspondingly threaded opening in the lower portion 128 of the lid 120. When the pneumatic system 200 is in its first configuration, the control line 208 is configured to transmit fluid from the supply line 204 via the valve 210 to the pumping chamber 125. When the pneumatic system 200 is in its second configuration, the control line 208 is configured to transmit fluid from the pumping chamber 125 to the vent line 206 via the valve 210. Each of the foregoing lines (i.e., supply line 204, vent line 206, control line 208) can be constructed of any suitable material including, for example, polyurethane tubing.

The valve 210 is configured to control the flow of oxygen into and out of the pumping chamber 125. In the embodiment illustrated in FIG. 7, the valve 210 is in fluidic communication with each of the supply line 204, the vent line 206, and the control line 208 via a first port, a second port, and a third port (none of which are shown in FIG. 7), respectively. In this manner, the valve 210 is configured to receive the fluid from the supply line 204 via the first port. In some embodiments, the first port defines an orifice that is about 0.10 to about 0.60 mm in size. In other embodiments, the first port defines an orifice that is about 0.15 to about 0.50 mm in size, about 0.20 to about 0.40 mm in size, about 0.20 to about 0.30 mm in size, or about 0.25 to about 0.30 mm in size. Specifically, in some embodiments, the first port defines an orifice that is about 0.25 mm in size. The valve 210 is configured to deliver the fluid to the vent line 206 via the second port. Additionally, the valve 210 is configured to receive the fluid from and deliver the fluid to the control line 208 via the third port. Specifically, the valve 210 is movable between a first configuration and a second configuration. In its first configuration, the valve 210 is configured to permit the flow of fluid from the supply line 204 through the valve 210 to the control line 208. As such, when the valve 210 is in its first configuration, the pneumatic system 200 is in its first configuration. In its second configuration, the valve 210 is configured to permit the flow of fluid from the control line 208 through the valve to the vent line 206. As such, when the valve 210 is in its second configuration, the pneumatic system 200 is in its second configuration.

The valve 210 is in electrical communication with the power source 218. In some embodiments, for example, the valve 210 is in electrical communication with the power source 218 via the PCBA 214. In the embodiment illustrated in FIGS. 6 and 7, the PCBA 214 is disposed in the chamber 124 between the valve 210 and the power source 218. In some embodiments, the PCBA 214 includes an electrical circuit (not shown) configured to electrically couple the power source 218 to the valve 210. The power source 218 is configured to provide power to the valve 210 to enable the valve 210 to control the flow of oxygen. In some embodiments, the power source 218 is configured to provide power to the valve 210 to enable the valve to move between its first configuration and its second configuration. The power source can be any suitable source of power including, for example, a battery. More specifically, in some embodiments, the power source is a lithium battery (e.g., a Li/MnO$_2$ 2/3 A battery). In another example, the power source can be an AA, C or D cell battery.

The valve 210 can be any suitable mechanism for controlling movement of the fluid between the first port, the second port, and the third port (and thus the supply line 204, vent line 206, and the control line 208, respectively). For example, in the embodiment illustrated in FIG. 7, the valve 210 is a solenoid valve. As such, in operation, the valve 210 is configured to convert an electrical energy received from the power source 218 to a mechanical energy for controlling the flow of oxygen therein. In some embodiments, for example, the valve 210 is configured to move to its first configuration when power is received by the valve from the power source 218. In some embodiments, the valve 210 is configured to move to its second configuration when the valve is electrically isolated (i.e., no longer receiving power) from the power source 218. In other words, the valve 210 is configured to deliver fluid (e.g., oxygen) to the pumping chamber 125 when the solenoid of the valve is energized by the power source 218, and the valve is configured to vent fluid (e.g., oxygen, carbon dioxide) from the pumping chamber when the solenoid of the valve is not energized by the power source. In some embodiments, the valve 210 is biased towards its second (or venting) configuration (in which power is not being provided from the power source 218 to the valve). Because the power source 218 is configured to not be in use when the pneumatic system 200 is not delivering oxygen to the pumping chamber 125, the usable life of the power source is extended, which enables the tissue to be extracorporeally preserved within the self-purging preservation apparatus 100 for a longer period of time. For example, in some embodiments, the solenoid of the valve 210 is configured to receive power from the power source 218 for about 20 percent of the total time the self-purging preservation apparatus 100, or at least the pneumatic system 200 of the self-purging preservation apparatus, is in use.

In some embodiments, the flow of fluid from the supply line 204 to the valve 210 is substantially prevented when the valve is in its second configuration. In this manner, the flow of oxygen into the valve 210 from the supply line 204 is stopped while the valve is venting fluid from the pumping chamber 125. As such, the overall oxygen use of the self-purging preservation apparatus 100 is reduced. In other embodiments, when the valve 210 is in its second configuration, the fluid being transmitted into the valve from the supply line 204 is transmitted through the valve to the vent line 206 without entering the pumping chamber 125. In this manner, the inflow of fluid from the supply line 204 to the valve 210 is substantially continuous. Accordingly, the flow of fluid from the valve 210 to the vent line 206 is also substantially continuous because the valve 210 is substantially continuously venting fluid from at least one of the supply line 204 and/or the control line 208.

Figure 8:
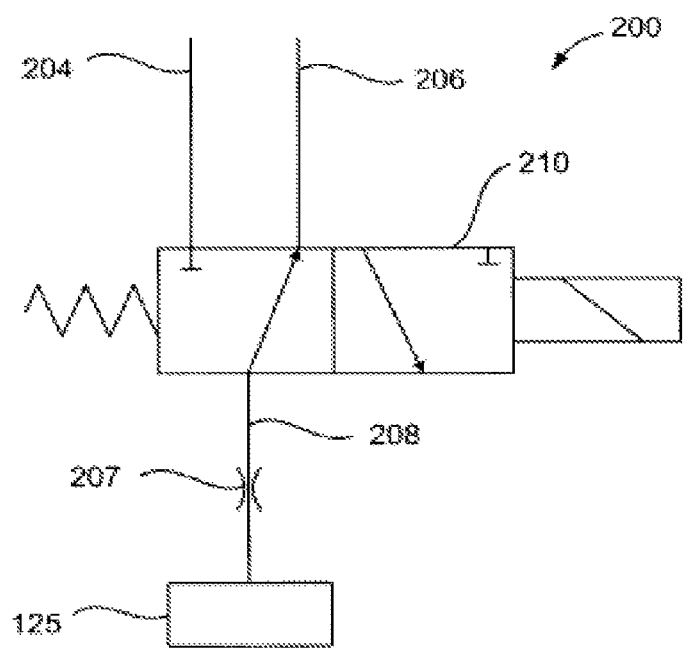
FIG. 8 is a schematic illustration of a pneumatic system and a pumping chamber of the self-purging preservation apparatus of FIG. 2.

Referring to a schematic illustration of the pneumatic system and pumping chamber in FIG. 8, the pneumatic system 200 is configured to control a change in pressure within the pumping chamber 125 of the lid assembly 110. In some embodiments, the pneumatic system 200 is configured to control the pressure within the pumping chamber 125 via the control line 208. More specifically, the rate of flow of fluid between the valve 210 and the pumping chamber 125 via the control line 208 is determined by a control orifice 207 disposed within the control line. The control orifice 207 can be, for example, a needle valve disposed within the control line 208. In some embodiments, the control orifice is about 0.10 to about 0.60 mm in size. In other embodiments, the first port defines an orifice that is about 0.15 to about 0.50 mm in size, about 0.20 to about 0.40 mm in size, about 0.20 to about 0.30 mm in size, or about 0.25 to about 0.30 mm in size. For example, in some embodiments, the control orifice 207 is about 0.25 mm in size. Because the rate of a change (e.g., rise, fall) in pressure within the pumping chamber 125 is based on the rate of flow of the fluid between the valve 210 and the pumping chamber 125 via the control line 208, the pressure within the pumping chamber 125 is also determined by the size of the control orifice 207 in the control line 208.

The pneumatic system 200 can be configured to move between its first configuration and its second configuration based on a predetermined control scheme. In some embodiments, the pneumatic system 200 is configured to move between its first configuration and its second configuration on a time-based control scheme. In some embodiments, the pneumatic system 200 is configured to move from its first configuration to its second configuration after a first period of time has elapsed. For example, the pneumatic system 200 can be configured to move from its first configuration to its second configuration after about 170 milliseconds. As such, the pneumatic system 200 is configured to deliver fluid (e.g., oxygen) to the pumping chamber 125 for the first time period (e.g., about 170 milliseconds). The pneumatic system 200 is configured to move from its second configuration to its first configuration after a second period of time has elapsed. For example, the pneumatic system 200 can be configured to move from its second configuration to its first configuration after being in its second configuration for about 700 milliseconds. As such, the pneumatic system 200 is configured to vent fluid (e.g. carbon dioxide) from the pumping chamber 125 for the second time period (e.g., about 700 milliseconds). The pneumatic system 200 is configured to alternate between its first configuration and its second configuration, and thus between delivering fluid into the pumping chamber 125 and venting fluid from the pumping chamber.

Although the pneumatic system 200 has been illustrated and described above as having a time-based control scheme, in some embodiments, the pneumatic system 200 is configured to move between its first configuration and its second configuration on a pressure-based control scheme. In some embodiments, the pneumatic system 200 is configured to move from its first configuration to its second configuration when a pressure within the pumping chamber 125 reaches a first threshold pressure. For example, the pneumatic system 200 can be configured to move from its first configuration to its second configuration when the pressure within the pumping chamber 125 is about 20 mmHg (millimeters of mercury), about 25 mmHg, about 30 mmHg, about 35 mmHg, about 40 mmHg, about 45 mmHg or about 50 mmHg. The pneumatic system 200 can be configured to move from its second configuration to its first configuration when a pressure within the pumping chamber 125 reaches a second threshold pressure. For example, the pneumatic system 200 can be configured to move from its second configuration to its first configuration when the pressure within the pumping chamber 125 is about 0 mmHg, about 5 mmHg, about 10 mmHg or about 15 mmHg. Said another way, when the pressure within the pumping chamber 125 is increased from the second threshold pressure to the first threshold pressure, the valve 210 is switched from delivering fluid to the pumping chamber to venting fluid from the pumping chamber. Similarly, when the pressure within the pumping chamber 125 is decreased from the first threshold pressure to the second threshold pressure, the valve 210 is switched from venting fluid from the pumping chamber to delivering fluid to the pumping chamber.

Because the pneumatic system 200 is configured to alternate between its first configuration and its second configuration, the pneumatic system 200 can be characterized as being configured to deliver oxygen to the pumping chamber 125 via a series of intermittent pulses. In some embodiments, however, the pneumatic system 200 is configured to deliver oxygen to the pumping chamber 125 in a substantially constant flow. In still another example, the pneumatic system 200 can be configured to selectively deliver oxygen in each of a substantially constant flow and a series of intermittent pulses. In some embodiments, the pneumatic system 200 is configured to control the flow of fluid within the pumping chamber 125, including the delivery of oxygen to the pumping chamber, in any combination of the foregoing control schemes, as desired by an operator of the self-purging preservation apparatus 100.

Figure 9:
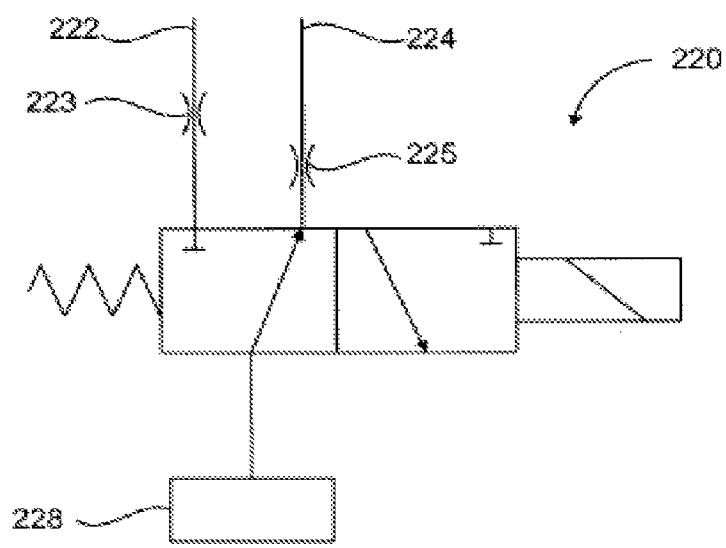
FIG. 9 is a schematic illustration of a pneumatic system and a pumping chamber of a self-purging preservation apparatus according to an embodiment.

Although the pneumatic system 200 has been illustrated and described herein as controlling the change in pressure within the pumping chamber 125 via a control orifice disposed in the control line 208, in other embodiments, a pneumatic system is configured to control the pressure within the pumping chamber via at least one control orifice disposed within at least one of the supply line and the vent line. Referring to FIG. 9, in some embodiments of a pneumatic system 220, a larger control orifice 223 is disposed within the supply line 222. In this manner, the pneumatic system 220 can permit a larger and/or quicker inflow of fluid from the supply line 222 to the pumping chamber, and thus can cause a quick pressure rise within the pumping chamber 228. In another example, in some embodiments, a smaller control orifice 225 is disposed within the vent line 224. In this manner, the pneumatic system 220 can restrict the flow of fluid venting through the vent line 224 from the pumping chamber 228, and thus can cause a slower or more gradual decline in pressure within the pumping chamber. As compared to pneumatic system 200, pneumatic system 220 can permit a shorter time period when the valve 210 is energized, thereby allowing power source 218 to operate the self-purging preservation apparatus for a longer period.

In use, the tissue is coupled to the tissue adapter 170. The lid assembly 110 is disposed on the canister 190 such that the tissue is received in the tissue chamber 192. The lid assembly 110 is coupled to the canister 190. Optionally, the lid assembly 110 and the canister 190 are coupled via the clamp 250. A desired amount of perfusate is delivered to the tissue chamber 192 via the fill port 108. Optionally, a desired amount of perfusate can be disposed within the compartment 194 of the canister 190 prior to disposing the lid assembly 110 on the canister. In some embodiments, a volume of perfusate greater than a volume of the tissue chamber 192 is delivered to the tissue chamber such that the perfusate will move through the ball check valve 138 into the second portion 129 of the pumping chamber 125.

A desired control scheme of the pneumatic system 200 is selected. Oxygen is introduced into the first portion 127 of the pumping chamber 125 via the pneumatic system 200 based on the selected control scheme. The pneumatic system 200 is configured to generate a positive pressure by the introduction of oxygen into the first portion 127 of the pumping chamber 125. The positive pressure helps to facilitate diffusion of the oxygen through the membrane 140. The oxygen is diffused through the membrane 140 into the perfusate disposed in the second portion 129 of the pumping chamber 125, thereby oxygenating the perfusate. Because the oxygen will expand to fill the first portion 127 of the pumping chamber 125, substantially all of an upper surface 141 of the membrane 140 which faces the first portion of the pumping chamber can be used to diffuse the oxygen from the first portion into the second portion 129 of the pumping chamber.

As the tissue uses the oxygen, the tissue will release carbon dioxide into the perfusate. In some embodiments, the carbon dioxide is displaced from the perfusate, such as when the pneumatic system 200 the oxygen is diffused into the perfusate because of the positive pressure generated by the pneumatic system. Such carbon dioxide can be diffused from the second portion 129 of the pumping chamber 125 into the first portion 127 of the pumping chamber 125. Carbon dioxide within the first portion 127 of the pumping chamber is vented via the control line 208 to the valve 210, and from the valve through the vent line 206 to the atmosphere external to the self-purging preservation apparatus 100.

The positive pressure also causes the membrane 140 to flex, which transfers the positive pressure in the form of a pulse wave into the oxygenated perfusate. The pulse wave generated by the pumping chamber is configured to facilitate movement of the oxygenated perfusate from the second portion 129 of the pumping chamber 125 into the tissue via the tissue adapter 170, thus perfusing the tissue. In some embodiments, the pumping chamber 125 is configured to generate a pulse wave that is an about 60 Hz pulse. In some embodiments, the pumping chamber 125 is configured to generate a pulse wave through the perfusate that is configured to cause a differential pressure within the tissue chamber 192 to be within the range of about 0 mmHg to about 50.0 mmHg. More specifically, in some embodiments, the pumping chamber 125 is configured to generate a pulse wave through the perfusate that is configured to cause a differential pressure within the tissue chamber 192 to be within the range of about 5 mmHg to about 30.0 mmHg.

At least a portion of the perfusate perfused through the tissue is received in the tissue chamber 192. In some embodiments, the pulse wave is configured to flow through the perfusate disposed in the tissue chamber 192 towards the floor 193 of the canister 190. The floor 193 of the canister 190 is configured to flex when engaged by the pulse wave. The floor 193 of the canister 190 is configured to return the pulse wave through the perfusate towards the top of the tissue chamber 192 as the floor 193 of the canister 190 is returned towards its original non-flexed position. In some embodiments, the returned pulse wave is configured to generate a sufficient pressure to open the ball check valve 138 disposed at the highest position in the tissue chamber 192. In this manner, the returned pulse wave helps to move the valve 138 to its open configuration such that excess fluid (e.g., carbon dioxide released from the tissue and/or the perfusate) can move through the valve from the tissue chamber 192 to the pumping chamber 125.

The foregoing perfusion cycle can be repeated as desired. For example, in some embodiments, the pneumatic system 200 is configured to begin a perfusion cycle approximately every second based on a time-based control scheme. As such, the pneumatic system 200 is configured to power on to deliver oxygen to the pumping chamber 125 for several milliseconds. The pneumatic system 200 can be configured to power off for several milliseconds, for example, until time has arrived to deliver a subsequent pulse of oxygen to the pumping chamber 125. Because the pneumatic system 200, and the solenoid valve 210 specifically, is only powered on when needed to transmit a pulse of oxygen to the pumping chamber, the usable life of the power source 218 can be extended for a longer period of time.

A self-purging preservation apparatus 300 according to an embodiment is illustrated in FIGS. 10-16. The self-purging preservation apparatus 300 is configured to oxygenate a perfusate and to perfuse a tissue for extracorporeal preservation of the tissue. The self-purging preservation apparatus 300 includes a lid assembly 310, a canister 390, and a coupling mechanism 450. Unless stated otherwise, self-purging preservation apparatus 300 can be similar in many respects (e.g., form and/or function) to the self-purging preservation apparatus described herein (e.g., self-purging preservation apparatus 10, 100, 700 (described below)), and can include components similar in many respects (e.g., form and/or function) to components of such self-purging preservation apparatus. For example, the canister 390 can be similar to the canister 190.

Figure 10:
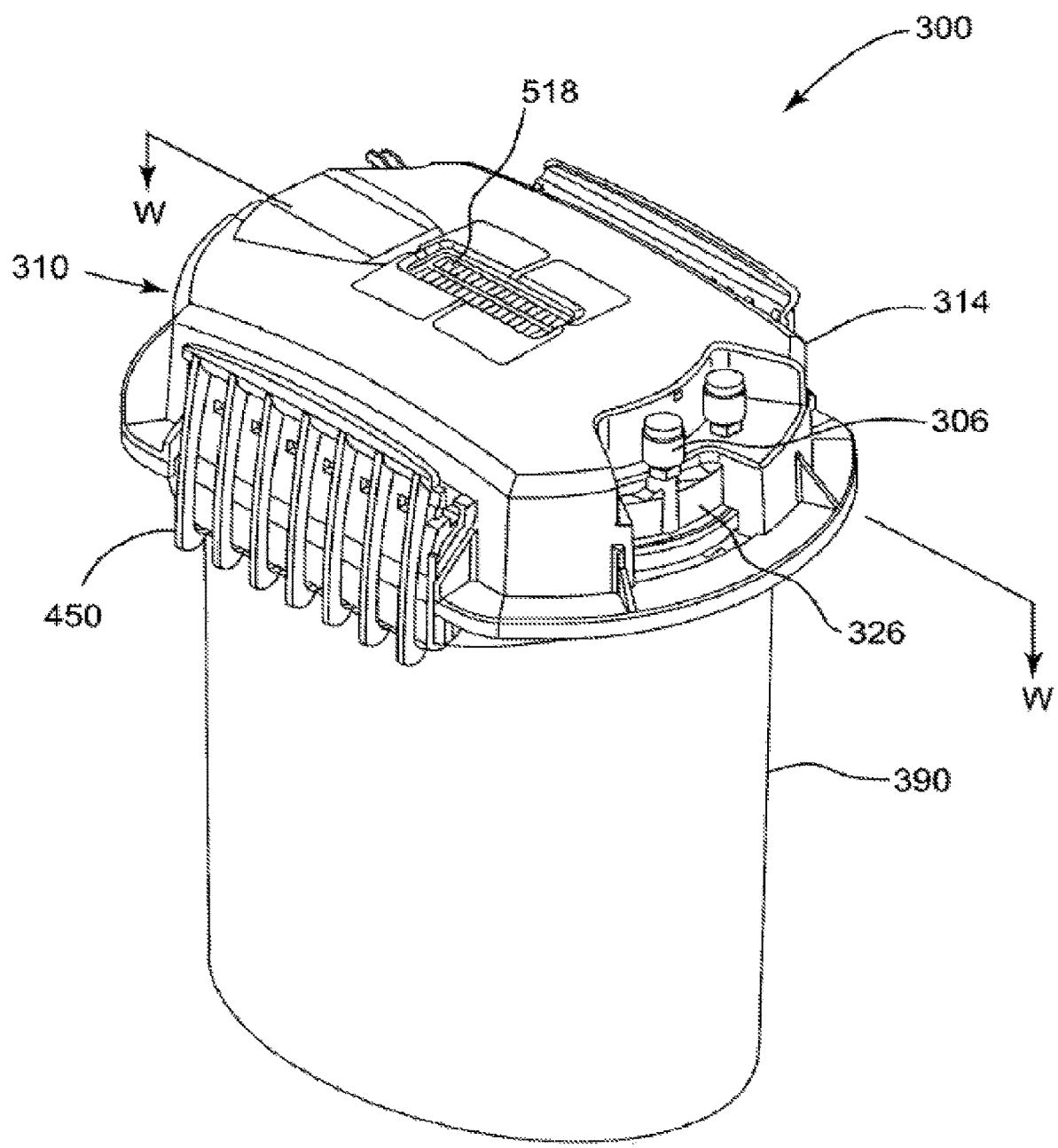
FIG. 10 is a front perspective view of a self-purging preservation apparatus according to an embodiment.
Figure 11:
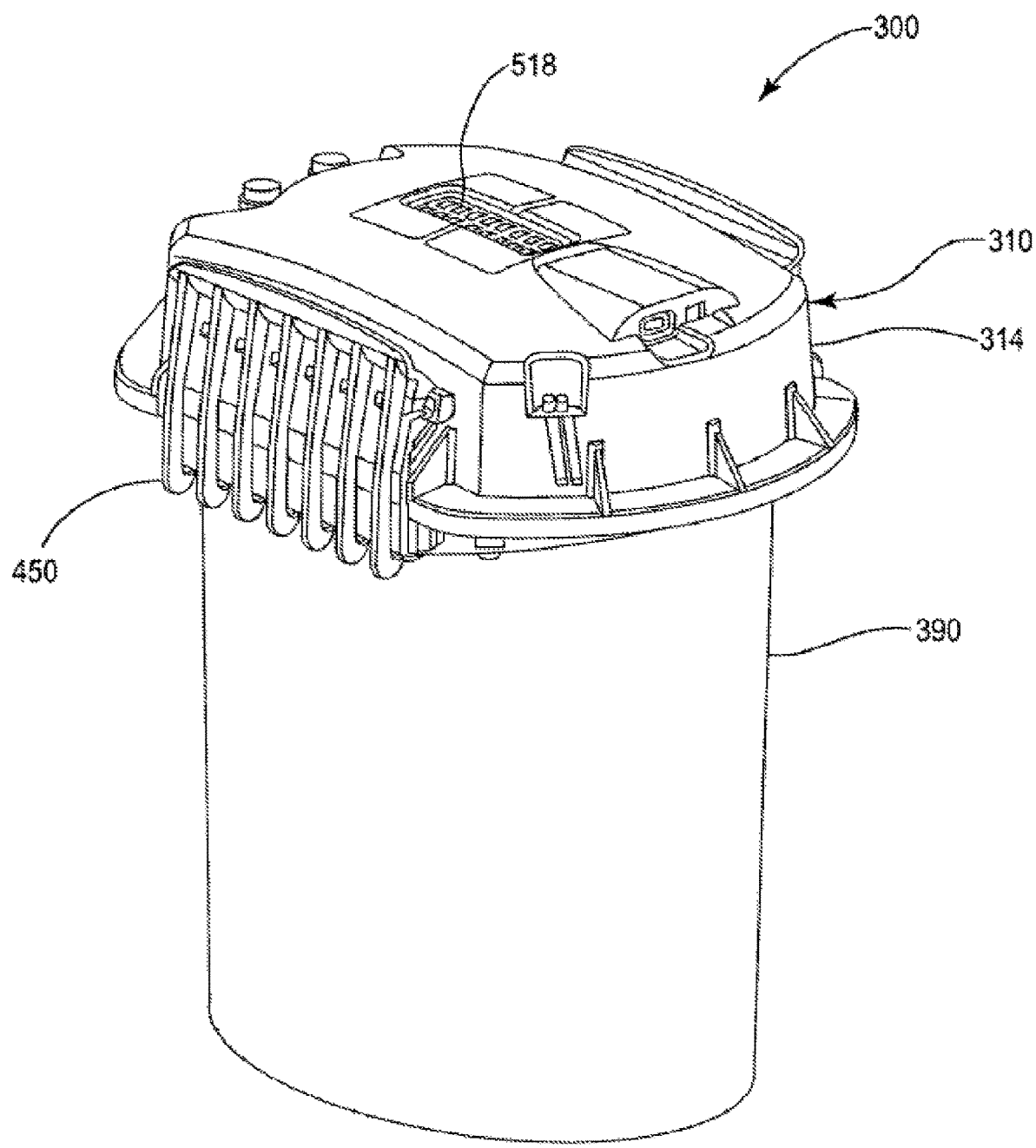
FIG. 11 is a rear perspective view of the self-purging preservation apparatus of FIG. 10.
Figure 12:
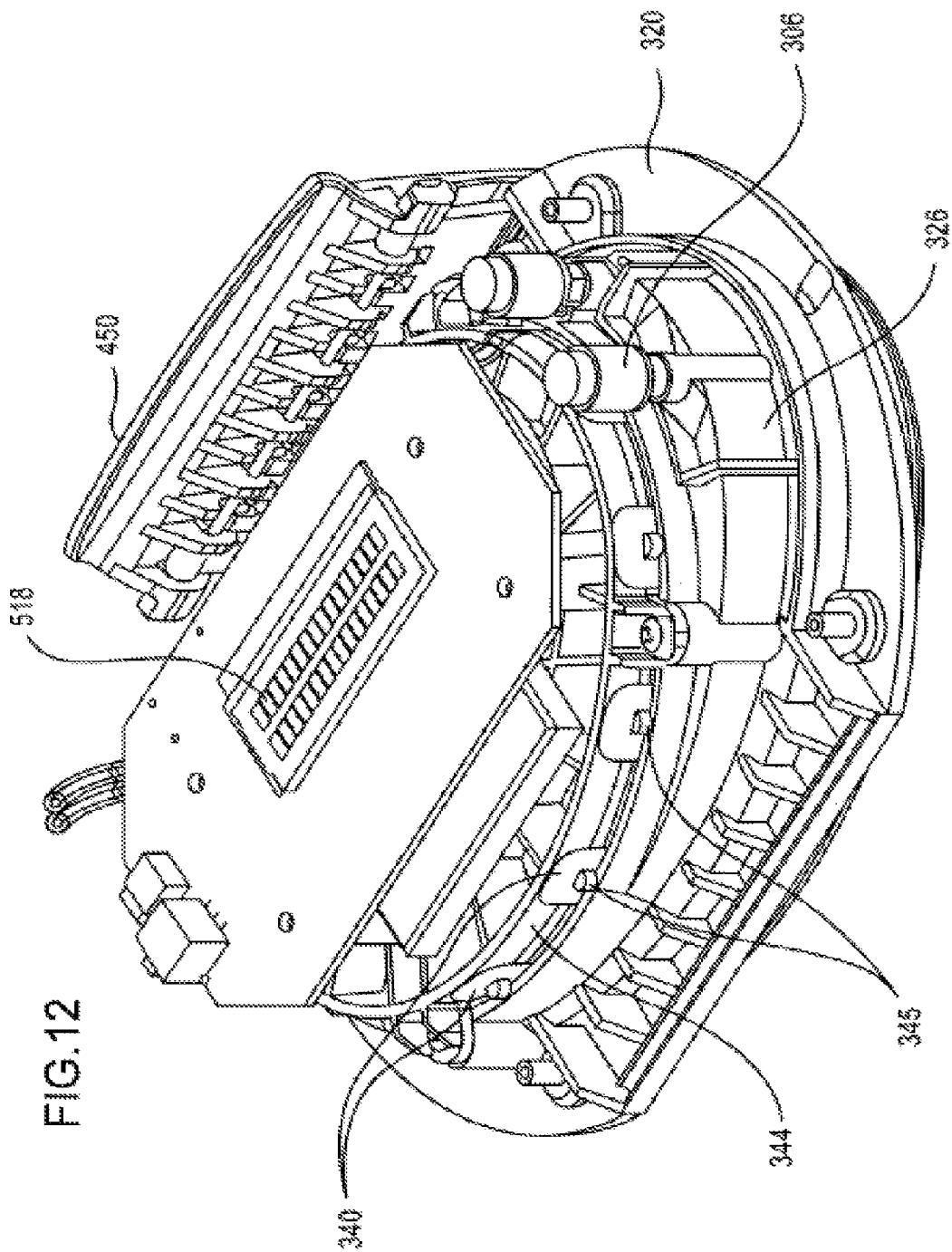
FIG. 12 is a front perspective view of the self-purging preservation apparatus of FIG. 10 with the lid cover, one of the clamps, and the tissue chamber removed.
Figure 13:
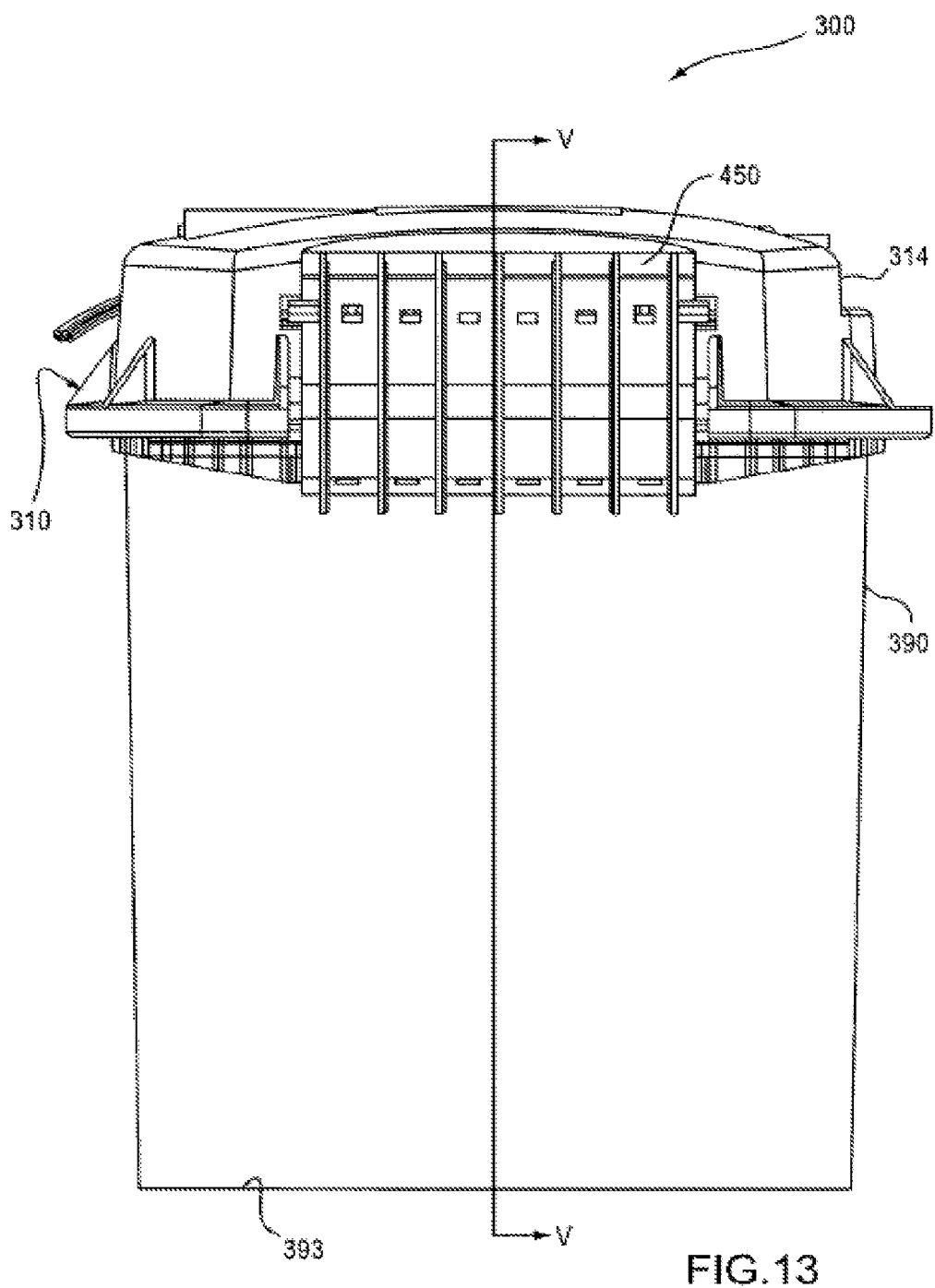
FIG. 13 is a side view of the self-purging preservation apparatus of FIG. 10.

The lid assembly 310 includes a lid cover 314 (e.g., as shown in FIG. 10) and a lid 320 (e.g., as shown in FIG. 12). The lid cover 314 is coupled to the lid 320. The lid cover 314 can be coupled to the lid 320 using any suitable mechanism for coupling. For example, the lid cover 314 can be coupled to the lid 320 with at least one of a screw, an adhesive, a hook and loop fastener, mating recesses, or the like, or any combination of the foregoing. A chamber 324 is formed between an upper portion 322 of the lid 320 and a bottom portion 316 of the lid cover 314. The chamber 324 is configured to receive components of a pneumatic system (e.g., the pneumatic system 200 described above) and the control system 500 (described in detail below with respect to FIG. 17).

The lid assembly 310 includes a first gasket 342, a membrane 340, and a membrane frame 344 disposed on the upper portion 322 of the lid 320. The lid assembly 310 defines a pumping chamber 325 configured to receive oxygen from the pneumatic system 200, to facilitate diffusion of the oxygen into a perfusate (not shown) and to facilitate movement of the oxygenated perfusate into a tissue (not shown). A top of the pumping chamber 325 is formed by the membrane frame 344. A bottom of the pumping chamber 325 is formed by an upper surface 334 of a base 332 of the lid assembly 310.

One or more components of the lid assembly 310 (e.g., the lid 320 and/or the lid cover 314) can be transparent, either in its entirety or in part. Retelling to FIGS. 10 and 12, the lid cover 314 includes a window (not shown), and the lid 320 includes a transparent portion 326 adjacent to, or at least in proximity to, a purge port 306. The transparent portion 326 permits a user to view any excess fluid (e.g., in the form of gas bubbles) in the pumping chamber 325 and to confirm when the excess fluid has been purged from the pumping chamber 325.

The first gasket 342 is disposed between the membrane 340 and the membrane frame 344 such that the first gasket is engaged with an upper surface 341 of the membrane 340. The first gasket 342 is configured to seal a perimeter of a first portion 327 of the pumping chamber 325 formed between the membrane frame 344 and the upper surface 341 of the membrane 340. In other words, the first gasket 342 is configured to substantially prevent lateral escape of oxygen from the first portion 327 of the pumping chamber 325 to a different portion of the pumping chamber. The first gasket 342 has a perimeter substantially similar in shape to a perimeter defined by the membrane 340 (e.g., when the membrane is disposed on the membrane frame 344). In other embodiments, however, a gasket can have another suitable shape for sealing the first portion 327 of the pumping chamber 325.

The membrane 340 is configured to permit diffusion of gas (e.g., oxygen, carbon dioxide, etc.) from the first portion 327 of the pumping chamber 325 through the membrane to a second portion 329 of the pumping chamber, and vice versa. The membrane 340 is configured to substantially prevent a liquid (e.g., the perfusate) from passing through the membrane. In this manner, the membrane 340 can be characterized as being semi-permeable. The membrane frame 344 is configured to support the membrane 340 (e.g., during the oxygenation and perfusion of the tissue). At least a portion of the membrane 340 is disposed (e.g., wrapped) about at least a portion of the membrane frame 344. In some embodiments, the membrane 340 is stretched when it is disposed on the membrane frame 344. The membrane 340 is disposed about a bottom rim of the membrane frame 344 such that the membrane 340 is engaged with a series of protrusions (e.g., the protrusions 345 shown in FIG. 12) configured to help retain the membrane 340 with respect to the membrane frame 344. The lid 320 and the membrane frame 344 are designed for oblique compression of the first gasket 342 therebetween. The lid 320 is designed such that the membrane 340, when stretched and disposed on the membrane frame 344, is virtually coplanar with a bottom portion 328 of the lid 320, which is inclined from a first side of the self-purging preservation apparatus 300 towards a second side of the self-purging preservation apparatus 300 (i.e., towards the purge port 306). As such, excess fluid (e.g., gas bubbles, perfusate, etc.) is more effectively purged from the pumping chamber 325, e.g., to prevent gas bubbles or the like from being trapped therein.

The pumping chamber 325 includes an obstruction free second portion 329. The second portion 329 of the pumping chamber 325 is configured to receive fluid (e.g., the perfusate) from the canister 390, as described in more detail below. The second portion 329 of the pumping chamber 325 is configured to contain the fluid for oxygenation of the fluid as oxygen is pumped into the first portion 327 of the pumping chamber 325 and permeated through the membrane 340 into the second portion 329 of the pumping chamber, thereby facilitating oxygenation of the fluid contained therein. In some embodiments, the lid 320 includes one or more purging structures, such as a lumen (not shown), configured to help avoid trapping of gas bubbles and/or other fluid at the membrane-lid interface.

Figure 14:
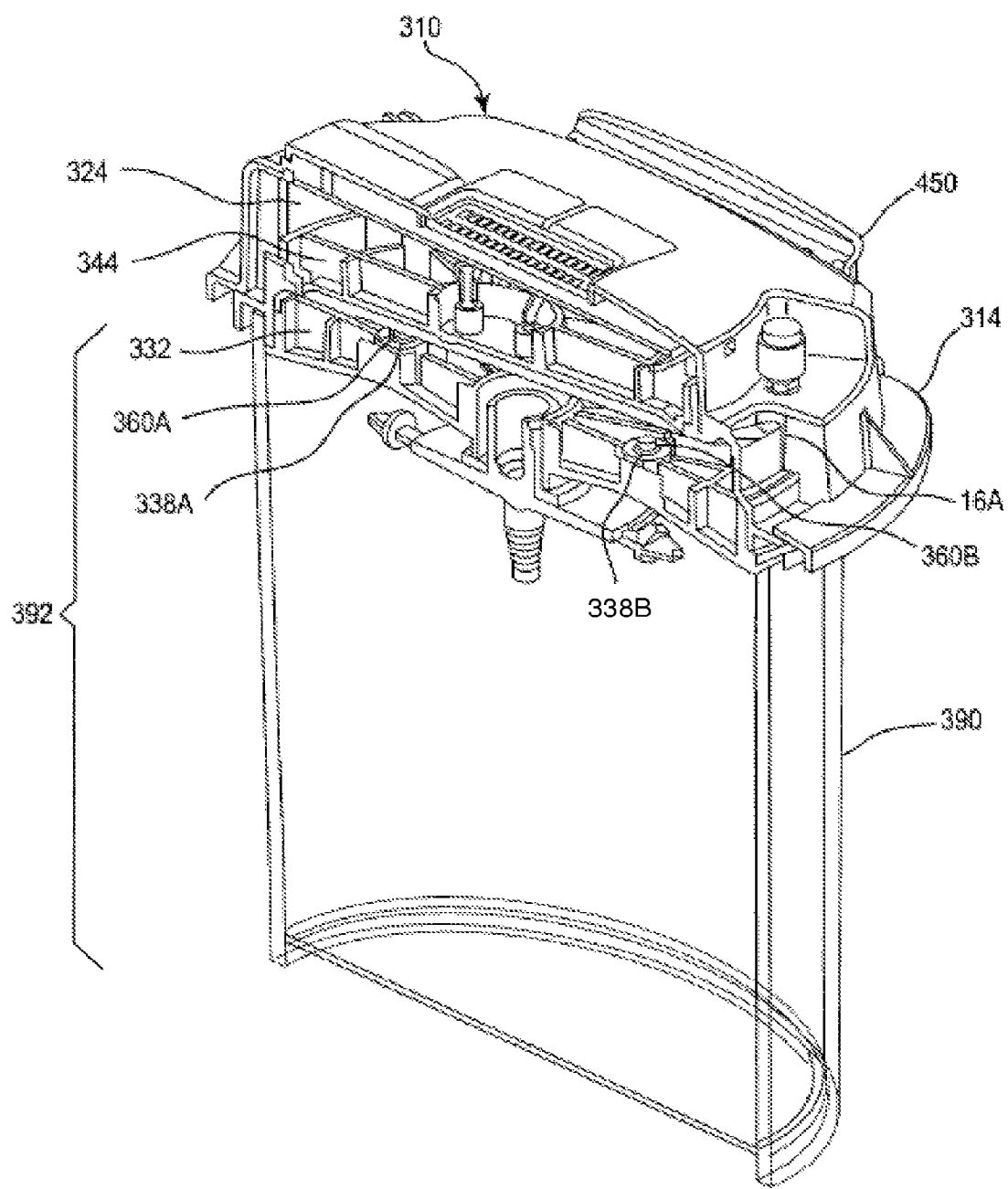
FIG. 14 is a cross-sectional view of the self-purging preservation apparatus of FIG. 10 taken along line W-W (shown in FIG. 10).
Figure 15:
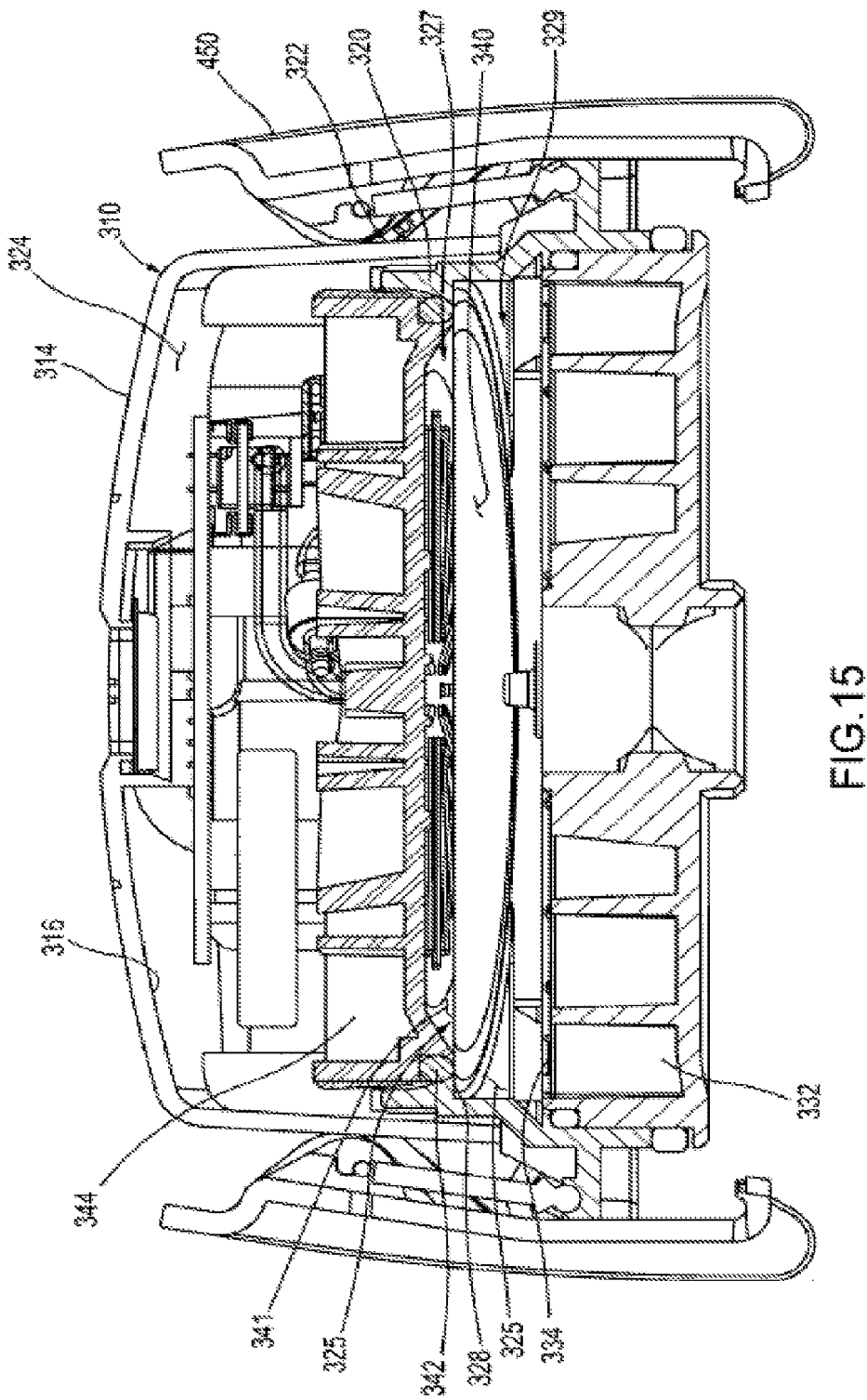
FIG. 15 is a cross-sectional view of the self-purging preservation apparatus of FIG. 10 taken along line V-V (shown in FIG. 13).
Figure 16B:
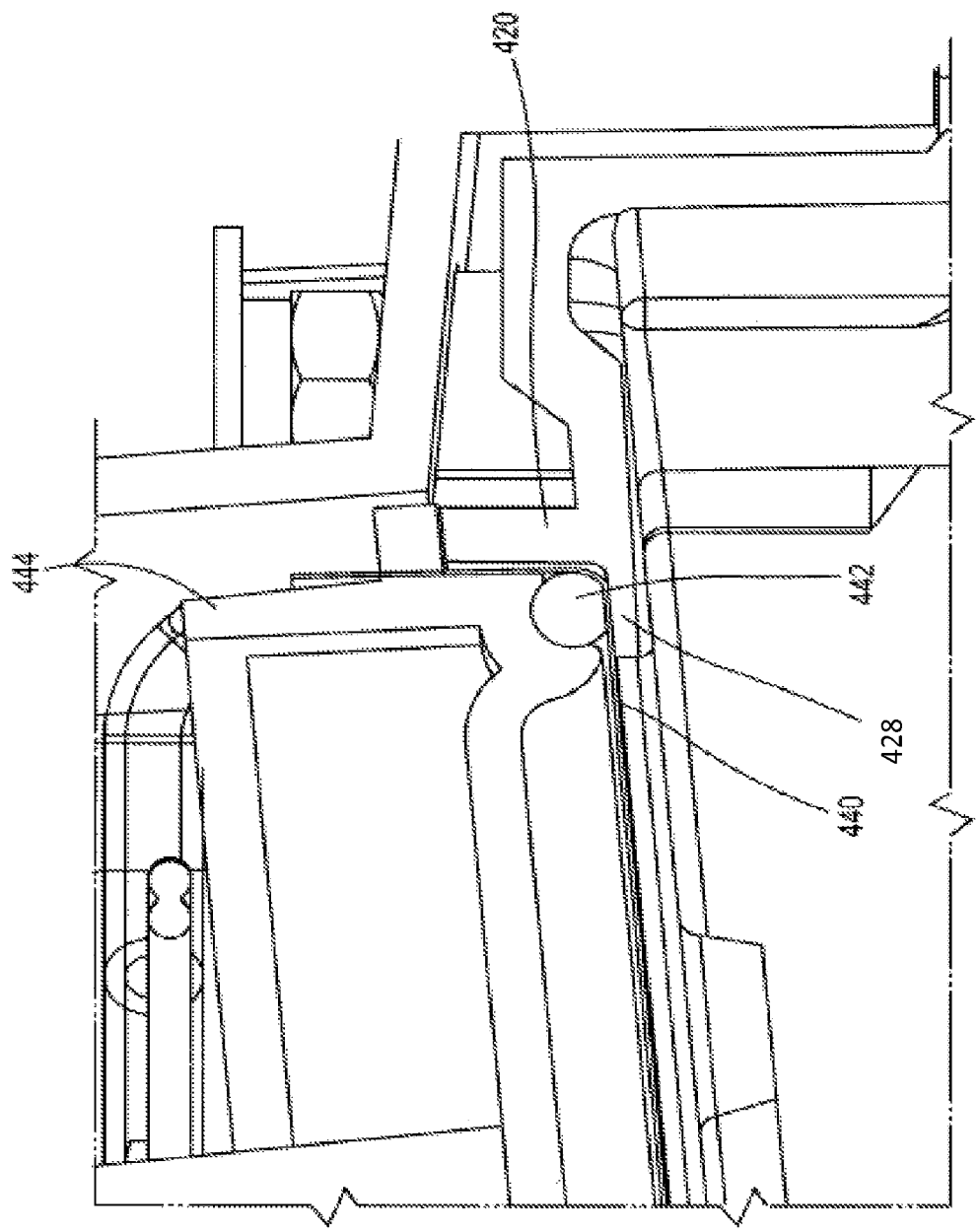
FIG. 16B is an enlarged cross-sectional view of a portion of a self-purging preservation apparatus according to an embodiment.

Referring to FIG. 14, the base 332 includes return flow valves 338A, 338B. Each return flow valve 338A, 338B is configured to permit fluid to flow from the canister 390 into the pumping chamber 325. The valves 338A, 338B each can be any suitable type of valve, including, for example, a ball check valve. Each valve 338A, 338B can include a return jet 360A, 360B, respectively, configured to focus fluid flowing from the canister 390 into the pumping chamber 325 onto the membrane 340. Because the membrane 340 is inclined towards the purge port 306, the focused flow of fluid from the return jets 360A, 360B onto the membrane 340 can help facilitate movement of the fluid towards the purge port 306, thereby facilitating purging of excess fluid from the self-purging preservation apparatus 300. Although illustrated as being nozzle-shaped, other designs of the jets 360A, 360B are suitable. The jets 360A, 360B are also configured to enhance mixing of fluid (e.g., perfusate) within the pumping chamber 325, which facilitates oxygenation of the fluid returning into the pumping chamber 325 from the canister 390.

Although lid 320 and the membrane frame 344 are illustrated (e.g., in FIG. 16A) and described as being configured to obliquely compress the first gasket 342 therebetween, in some embodiments, a self-purging preservation apparatus can include a lid and membrane frame configured to differently compress a gasket therebetween. For example, retelling to FIG. 16B, a lid 420 and a membrane frame 444 are configured to axially compress a first gasket 442. In some embodiments, one or more additional purging structures can be twined on a bottom portion 428 of the lid 420, such as a lumen (not shown), to prevent the trapping of gas bubbles and/or other fluid at the membrane-lid interface.

The coupling mechanism 450 is configured to couple the lid assembly 310 to the canister 390. The coupling mechanism 450 can include a first clamp 312 and a second clamp 313 different than the first clamp. The first clamp 312 and the second clamp 313 can be disposed on opposing sides of the lid assembly 310. Each of the clamps 312, 313 are configured to be disposed about a portion of a lower rim of the lid 320 and an upper rim of the canister 390. The clamps 312, 313 are configured to be moved between a first, or open configuration in which the lid assembly 310 and the canister 390 are freely removable from each other, and a second, or closed, configuration in which the lid assembly 310 and the canister 390 are not freely removably from each other. In other words, in its second configuration, the handles 312, 313 of the coupling mechanism 450 are configured to lock the lid assembly 310 to the canister 390. The clamps 312, 313 can be any suitable clamp, including, for example, a toggle clamp.

Figure 17:
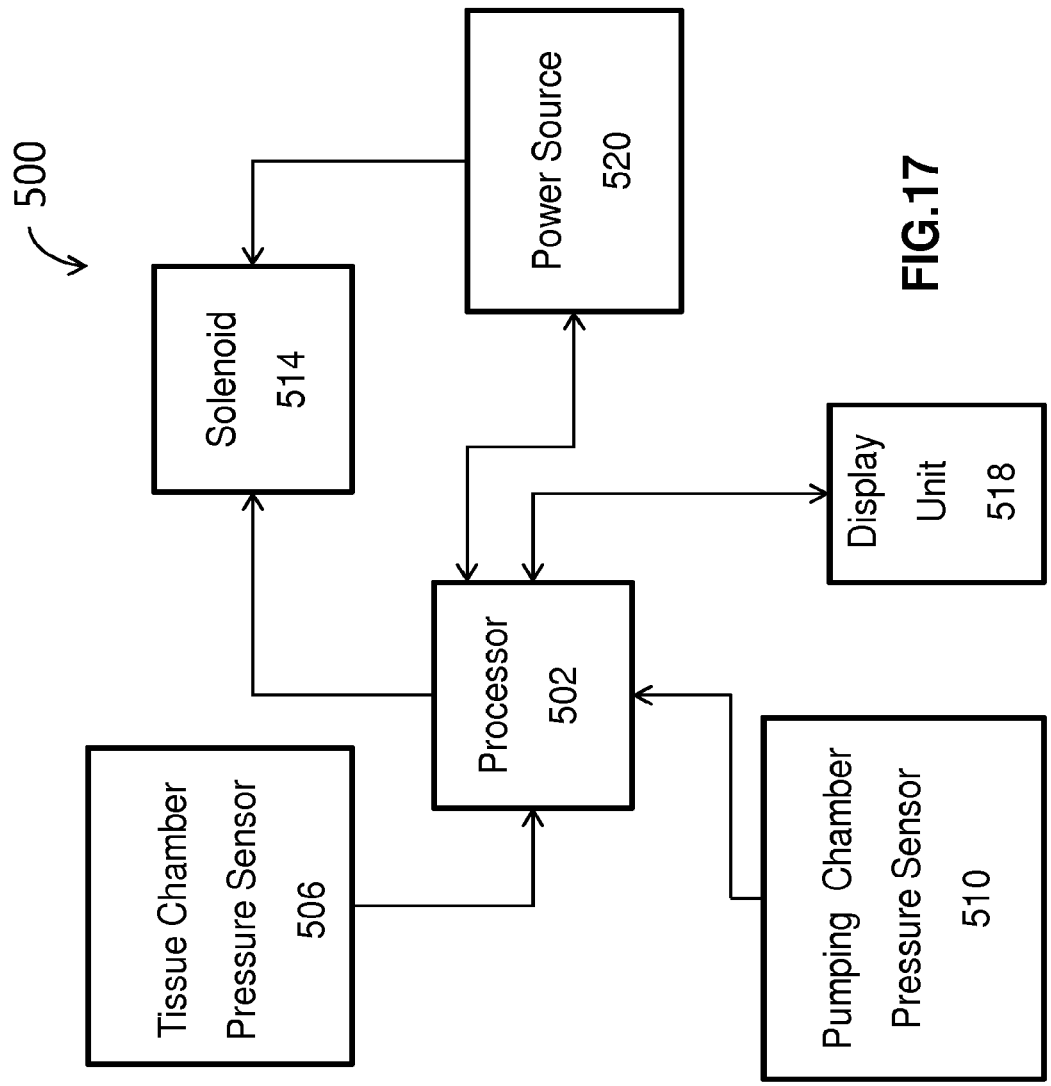
FIG. 17 is a component diagram of a control system according to an embodiment.

Referring to FIG. 17, the control system 500 includes a processor 502, a tissue chamber pressure sensor 506, a pumping chamber pressure sensor 510, a solenoid 514, a display unit 518, and a power source 520. In some embodiments, the control system 500 includes additional components, such as, for example, components configured for wired or wireless network connectivity (not shown) for the processor 502.

The control system 500 is described herein with reference to the self-purging preservation apparatus 300, however, the control system is suitable for use with other embodiments described herein (e.g., self-purging preservation apparatus 10, 100, and/or 700). The pumping chamber pressure sensor 510 is configured to detect the oxygen pressure in the pumping chamber 325. Because the pumping chamber 325 is split into the first and second portions 327, 329, respectively, by the semi-permeable membrane 340, which is configured to undergo relatively small deflections, the oxygen pressure in the first portion 327 of the pumping chamber 325 is approximately equal to the fluid (e.g., perfusate) pressure in the second portion 329 of the pumping chamber 325. Therefore, measuring the fluid pressure in either the first portion 327 or the second portion 329 of the pumping chamber 325 approximates the fluid pressure in the other of the first portion or the second portion of the pumping chamber 325.

The tissue chamber pressure sensor 506 is configured to detect the fluid pressure in the canister 390. Each pressure sensor 506, 510 can be configured to detect the fluid pressure in real-time and permit instantaneous determination of small pressure changes. Examples of pressure sensors that can be used include, but are not limited to, analog pressure sensors available from Freescale (e.g., MPXV5010GP-NDD) and from Honeywell (e.g., HSCMRNNOO1PGAA5). At least one of the pressure sensors 506, 510 can be configured to measure pressures between 0-1.0 psig with a 5 volt power supply. In some embodiments, at least one of the pressure sensors 506, 510 can be configured to detect pressure variations as small as 0.06 mmHg The sensors 506, 510 can be placed in the chamber 324 at the same height to avoid pressure head measurement errors.

The solenoid 514 is disposed in the chamber 324. The solenoid 514 is configured to control the opening and/or closing of one or more valves (not shown in FIG. 17) for gas flow to and from the pumping chamber 325. The solenoid 514 is operably connected to the power source 520 for optimal power management.

The display unit 518 is configured to display one or more parameters. Display parameters of the display unit 518 can include, for example, elapsed time of operation, operating temperature, flow rate, and/or resistance, which are key metrics for determining the overall health of the tissue being transported by the self-purging preservation apparatus 300. Calculation of the flow rate and resistance parameters is described in more detail below. The processor 502 is configured to receive information associated with the pressure in the pumping chamber 325 and in the canister 390 via the sensors 510, 506, respectively. The processor 502 is configured to control operation of the solenoid 514, to control the supply of power from the power source 520 to the solenoid 514, and to display operating parameters on the display unit 518.

Figure 18:
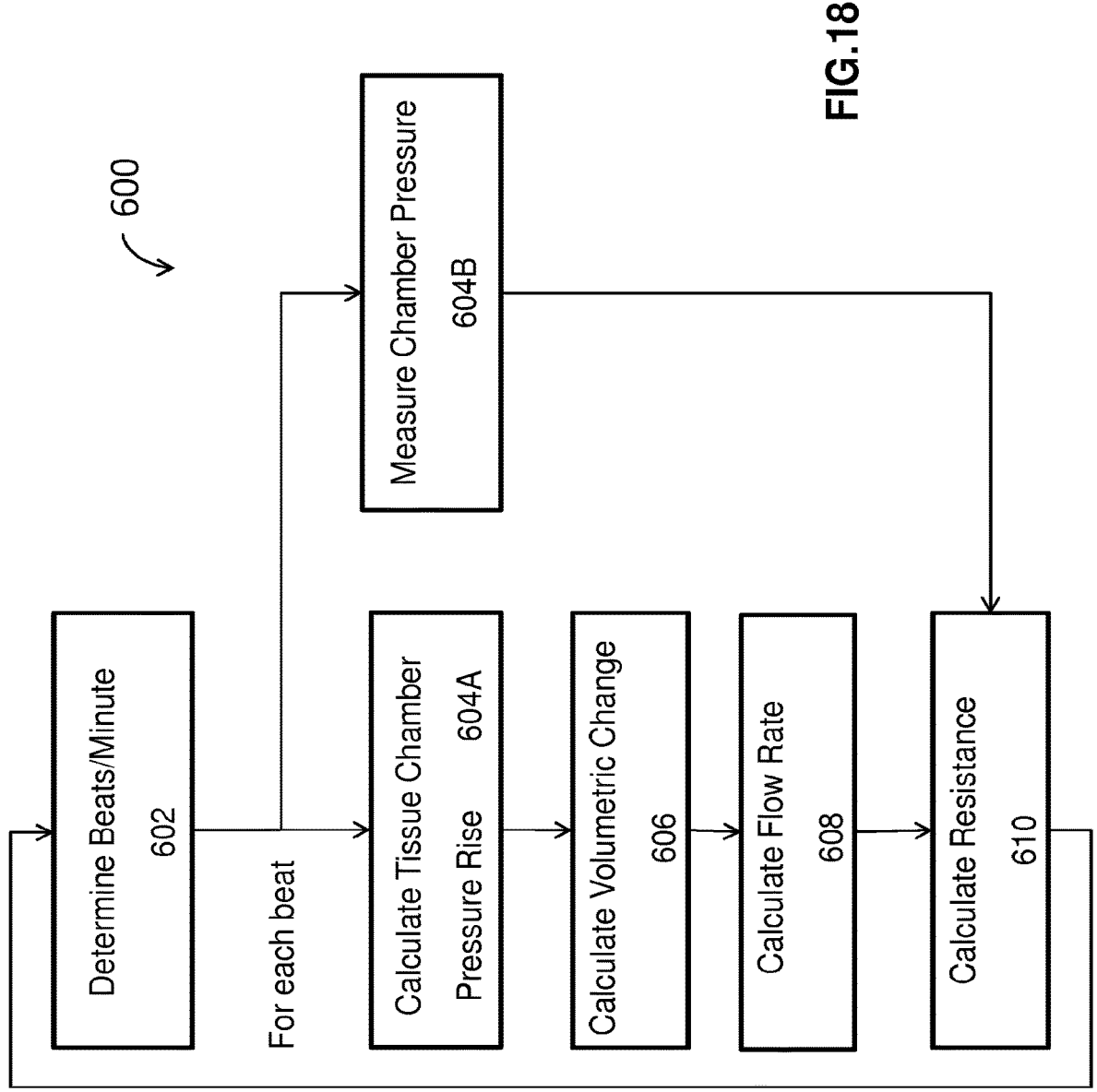
FIG. 18 is a flow diagram of a method for calculating flow rate and resistance according to an embodiment.
Figure 19:
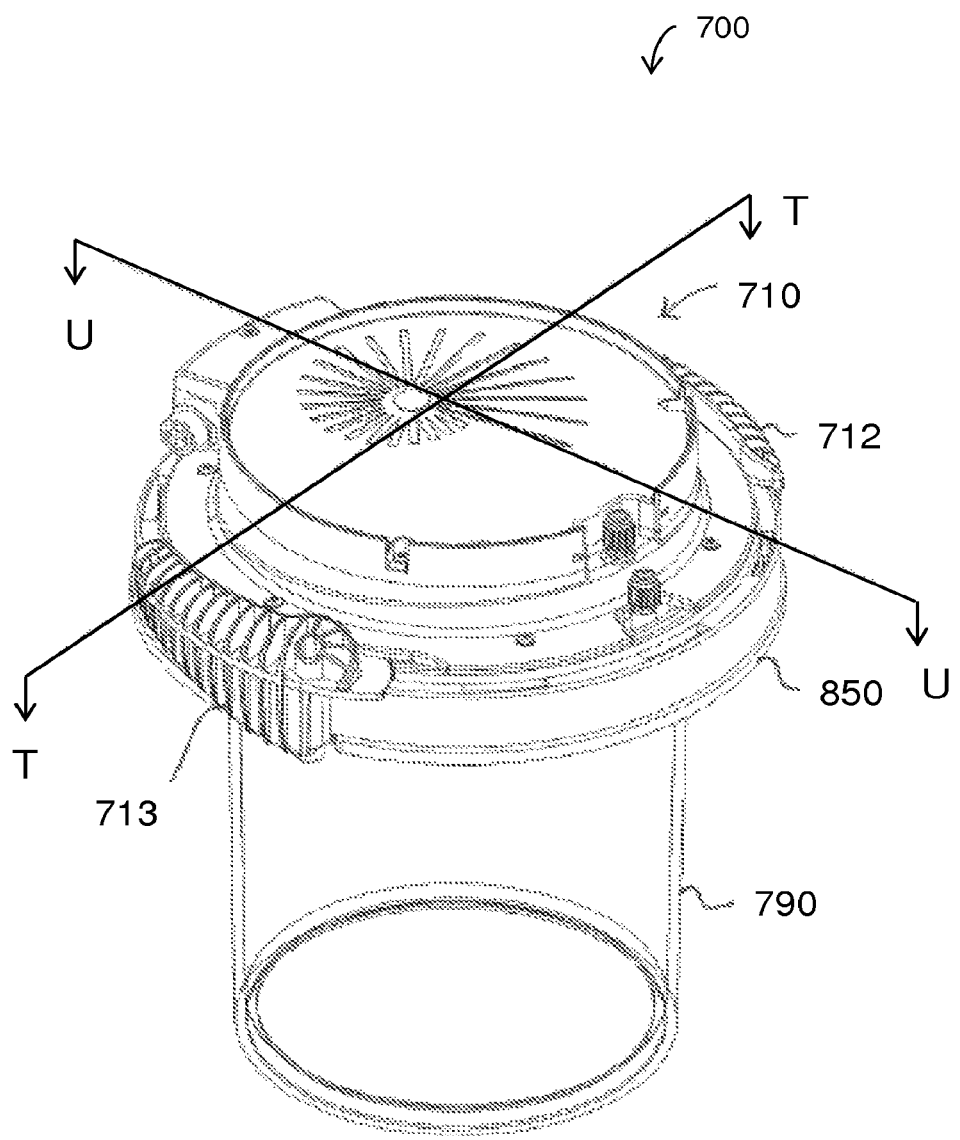
FIG. 19 is a perspective view of a self-purging preservation apparatus according to an embodiment.

The processor 502 is configured to calculate the flow rate and resistance, as illustrated in FIG. 18. Flow rate is a measure of the tissue's compliance to fluid flow around the tissue (e.g. blood flow), and can be a significant indicator of tissue viability. In some embodiments, the processor 502 is configured to evaluate such parameters (i.e., flow rate and resistance) continually and in real time. In some embodiments, the processor 502 is configured to periodically evaluate such parameters at predetermined time intervals.

Referring to FIG. 18, a flow chart of a method 600 for evaluating a parameter, such as flow rate resistance, according to an embodiment is illustrated. The method 600 is described herein with respect to self-purging preservation apparatus 300 and control unit 500, however, can be performed by another self-purging preservation apparatus described herein. At 602, the number of beats/minute (bpm)

is determined As used herein, "beat" refers to a pressure increase caused by a first volume of fluid (e.g., oxygen from pneumatic system 200) being introduced (e.g., intermittently) into the pumping chamber 325, which in turn causes a pressure wave that in turn causes a second volume of fluid (e.g., oxygenated perfusate) to be pumped or otherwise transferred from the pumping chamber 325 towards the canister 390 and/or a tissue contained in the canister 390. Determination of the bpm can be based on the frequency with which the solenoid 514 (under the control of processor 502) permits gas exchange via the control orifice.

Because the canister 390 is compliant (i.e., it has a flexible floor 393), the canister flexes with each "beat" and then returns to its starting position. As the canister 390 floor flexes, the canister accepts the second volume of fluid from the pumping chamber 325. When the floor 393 of the canister 390 relaxes, the second volume of fluid returns to the pumping chamber 325 through the valves 338A, 338B. The canister 390 floor 393 flexing and relaxing process can be repeated for each beat.

As the second volume of fluid enters the canister 390, pressure in the canister 390 (or more specifically, a tissue chamber 392, illustrated in FIG. 14, defined by the canister 390 and the lid assembly 310) rises and causes the canister 390 floor 393 to flex. This rise is pressure is measured by the tissue chamber pressure sensor 506. At 604A, the rise in tissue chamber pressure is calculated as a difference between the highest tissue chamber pressure and lowest tissue chamber pressure for each beat. In some embodiments, the tissue chamber pressure is sampled at a rate significantly higher than the number of beats/minute (e.g. at 1 kHz for 60 bpm), such that multiple tissue chamber pressure measurements are taken prior to performing the calculation of tissue chamber pressure rise at 604A. For example, in some embodiments, the tissue chamber pressure is sampled at 610 Hz (i.e., 610 samples per second).

As described above, the floor 393 of the canister 390 is a thin plate configured to undergo small deformations, such that its deflection due to pressure/volume changes is linear and is a measure of the volumetric compliance (defined as volume displaced per unit pressure change) of the canister. In one embodiment, volumetric compliance of the canister 390 is known and preprogrammed into the processor 502. In another embodiment, the processor 502 is configured to calculate volumetric compliance in real-time. At 606, the volumetric change is calculated by multiplying the calculated rise in canister pressure with the known/estimated volumetric compliance of the canister 390.

At 608, the flow rate is calculated by dividing the calculated change in volume by the beat period (i.e., a time interval between consecutive beats, measured in units of time). An average of several consecutive values of flow rate or other calculated values can be displayed to minimize beat variations. For example, a moving average value can be displayed.

At 610, the resistance is calculated. Resistance is expressed in units of pressure over flow rate, for example, mmHg/(mL/min). Flow rate is calculated as described above. The resistance is calculated by the processor 502 based upon the calculated canister pressure rise, calculated at 604A, and a measured chamber pressure, at 604B. The calculated canister pressure rise and measured chamber pressure can be based on substantially simultaneous and relatively high rate sampling of the pressure on each side of the tissue (i.e. at both the tissue chamber sensor 506 and the pumping chamber sensor 510). In some embodiments, the sampling rate is significantly higher than the number of beats per minute. For example, the pressures at the sensors 506, 510 can be sampled 1,000 times per second (1 kHz). As the oxygen pressure in the pumping chamber 325 rises, the pressure in the canister 390 rises at a slower rate. For improved accuracy, pressure can be measured at a high rate and accumulated for each beat period. For example, the total pressure impulse for each beat can be integrated step-wise. Further averaging or other statistical analysis can be performed by the processor 502 to reduce error. Due to the low operating pressures of the self-purging preservation apparatus, a resistance to flow can be approximated by laminar flow, such that instantaneous flow rate is proportional to the instantaneous pressure drop. Calculations can be performed in real-time using direct pressure measurements.

A self-purging preservation apparatus 700 according to an embodiment is illustrated in FIGS. 19-29. The self-purging preservation apparatus 700 is configured to oxygenate a perfusate and to perfuse a tissue for extracorporeal preservation of the tissue. Unless stated otherwise, the self-purging preservation apparatus 700 can be similar in many respects (e.g., form and/or function) to the self-purging preservation apparatus described herein (e.g., self-purging preservation apparatus 10, 100, 300), and can include components similar in many respects (e.g., form and/or function) to components of the self-purging preservation apparatus described herein. The self-purging preservation apparatus 700 includes a lid assembly 710, a canister 790, and a coupling mechanism 850.

The lid assembly 710 defines a chamber 724 (see, e.g., FIG. 25) configured to receive components of a pneumatic system (not shown), such as the pneumatic system 200 described above, and/or a control system (not shown), such as the control system 500 described above. In some embodiments, the chamber 724 is formed by a lid 720 of the lid assembly 710. In some embodiments, the chamber 724 can be formed between a lower portion 723 of the lid 720 and an upper portion 722 of the lid.

Figure 20:
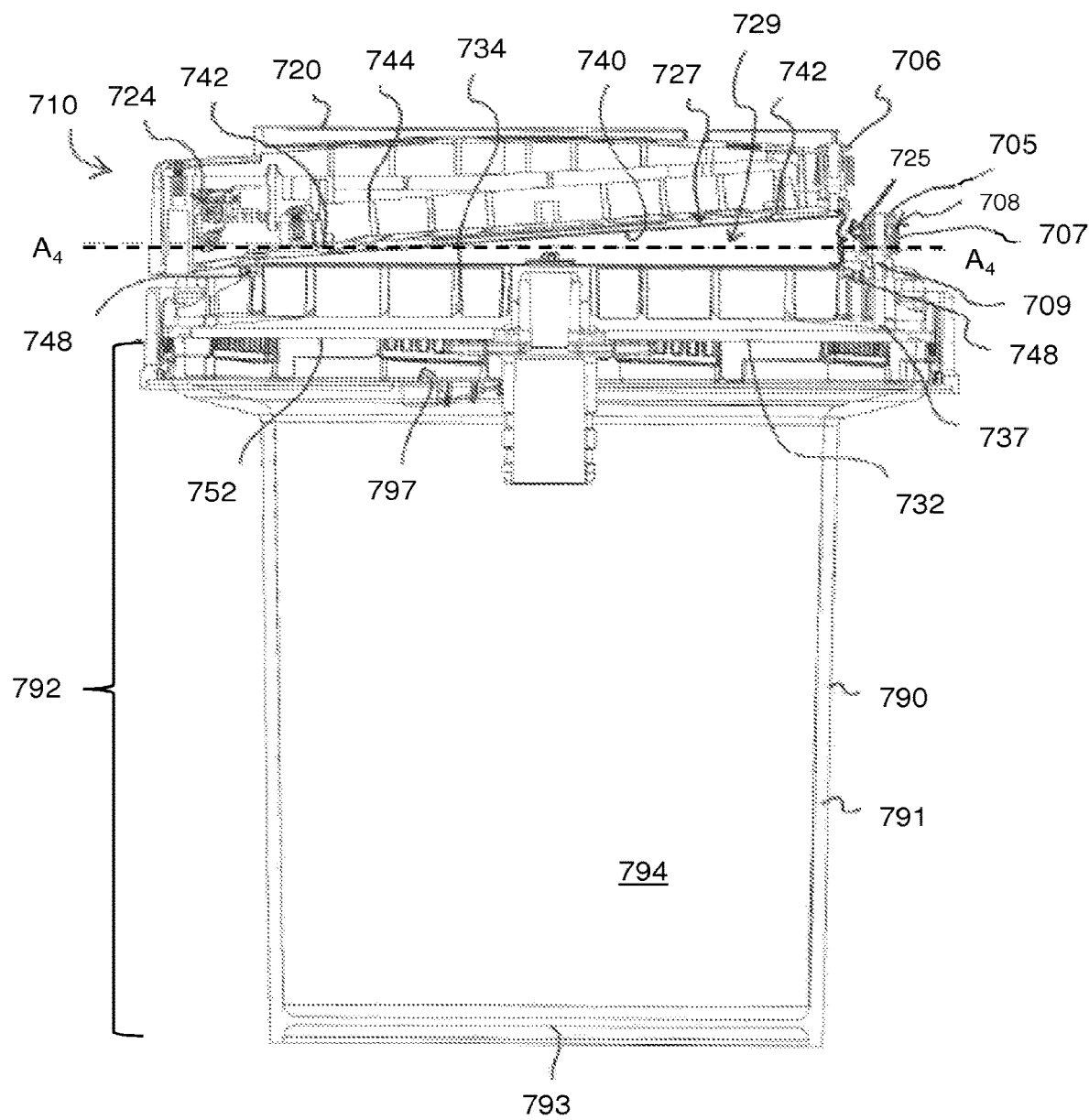
FIG. 20 is a cross-sectional view of the self-purging preservation apparatus of FIG. 19 taken along line U-U (shown in FIG. 19).
Figure 21A:
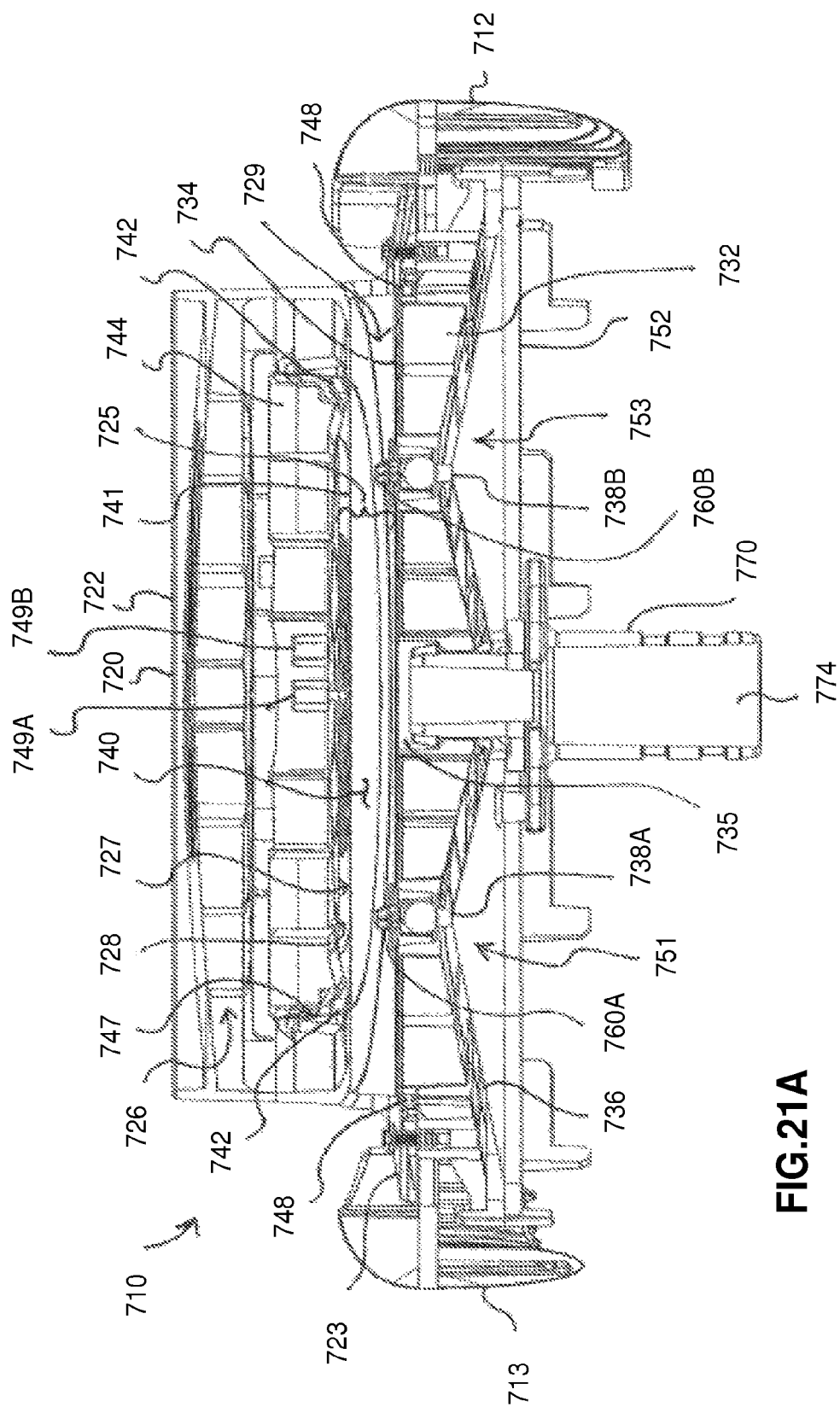
FIG. 21A is a cross-sectional view of a lid assembly of the self-purging preservation apparatus of FIG. 19 taken alone line T-T (shown in FIG. 19).

Retelling to FIGS. 20 and 21A, the lid assembly 710 defines a pumping chamber 725 configured to receive oxygen (e.g., from the pneumatic system), to facilitate diffusion of the oxygen into a perfusate (not shown) and to facilitate movement of the oxygenated perfusate into a tissue (not shown). A top of the pumping chamber 725 is formed by a lower portion 728 of a membrane frame 744 of the lid assembly 710. A bottom of the pumping chamber 725 is formed by an upper surface 734 of a base 732 of the lid assembly 710.

As illustrated in FIGS. 20-24, the lid assembly 710 includes a first gasket 742, a membrane 740, and the membrane frame 744. The membrane 740 is disposed within the pumping chamber 725 and divides the pumping chamber 725 into a first portion 727 and a second portion 729 different than the first portion. The first gasket 742 is disposed between the membrane 740 and the membrane frame 744 such that the first gasket is engaged with an upper surface 741 of the membrane 740 and a lower, perimeter portion of the membrane frame 744 (see, e.g., FIG. 24). The first gasket 742 is configured to seal a perimeter of the first portion 727 of the pumping chamber 725 twined between the lower portion 728 of the membrane frame 744 and the upper surface 741 of the membrane 740. In other words, the first gasket 742 is configured to substantially prevent lateral escape of oxygen from the first portion 727 of the pumping chamber 725 to a different portion of the pumping chamber. In the embodiment illustrated in FIG. 24, the first gasket 742 has a perimeter substantially similar in shape to a perimeter defined by the membrane 740 (e.g., when the membrane is disposed on the membrane frame 744). In other embodiments, however, a first gasket can have another suitable shape for sealing a first portion of a pumping chamber configured to receive oxygen from a pneumatic system.

The first gasket 742 can be constructed of any suitable material. In some embodiments, for example, the first gasket 742 is constructed of silicone, an elastomer, or the like. The first gasket 742 can have any suitable thickness. For example, in some embodiments, the first gasket 742 has a thickness within a range of about 0.1 inches to about 0.15 inches. More specifically, in some embodiments, the first gasket 742 has a thickness of about 0.139 inches. The first gasket 742 can have any suitable level of compression configured to maintain the seal about the first portion 727 of the pumping chamber 725 when the components of the lid assembly 710 are assembled. For example, in some embodiments, the first gasket 742 is configured to be compressed by about 20 percent.

The membrane 740 is configured to permit diffusion of gas (e.g., oxygen) from the first portion 727 of the pumping chamber 725 through the membrane to the second portion 729 of the pumping chamber, and vice versa. The membrane 740 is configured to substantially prevent a liquid (e.g., the perfusate) from passing through the membrane. In this manner, the membrane 740 can be characterized as being semi-permeable. The membrane frame 744 is configured to support the membrane 740 (e.g., during the oxygenation of the perfusate and perfusion of the tissue). The membrane frame 744 can have a substantially round or circular shaped perimeter. The membrane frame 744 includes a first port 749A and a second port 749B. The first port 749A is configured to convey fluid between the first portion 727 of the pumping chamber and the pneumatic system (not shown). For example, the first port 749A can be configured to convey oxygen from the pneumatic system to the first portion 727 of the pumping chamber 725. The second port 749B is configured to permit a pressure sensor line (not shown) to be disposed therethrough. The pressure sensor line can be, for example, polyurethane tubing. The ports 749A, 749B can be disposed at any suitable location on the membrane frame 744, including, for example, towards a center of the membrane frame 744 as shown in FIG. 21A. Although the ports 749A, 749B are shown in close proximity in FIG. 21A, in other embodiments, the ports 749A, 749B can be differently spaced (e.g., closer together or further apart).

Figure 22:
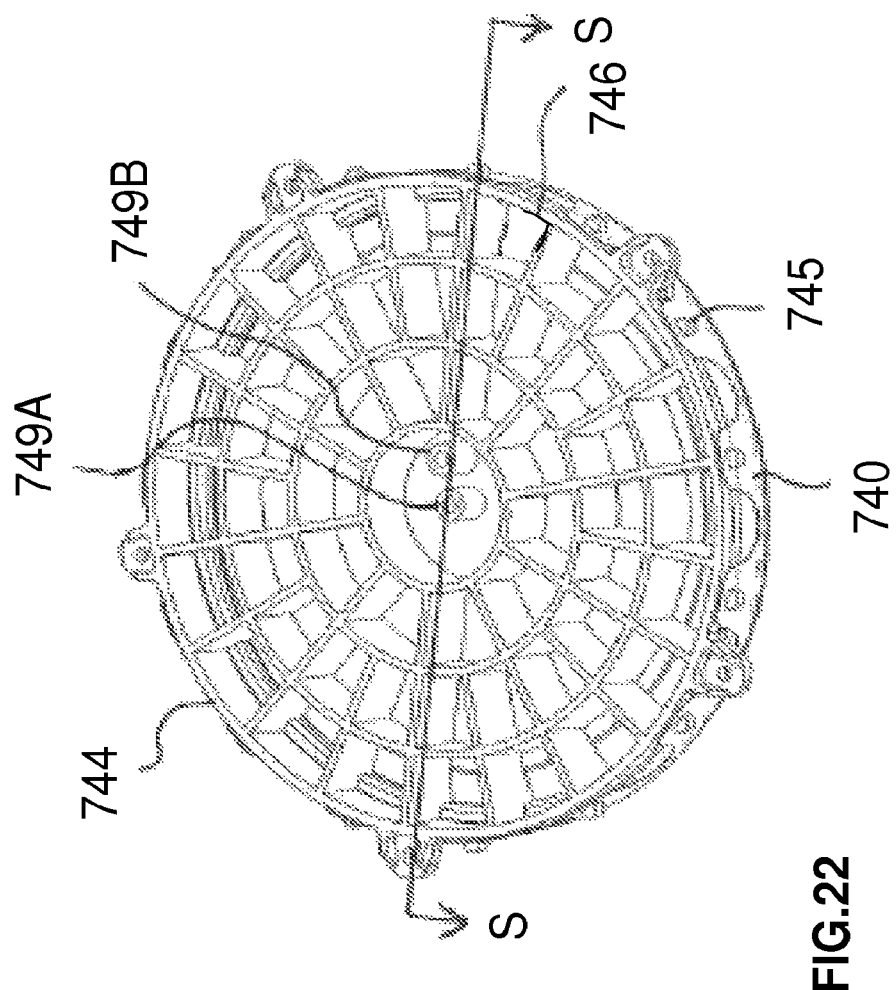
FIG. 22 is a top perspective view of a portion of the lid assembly of the self-purging preservation apparatus of FIG. 19.
Figure 23:
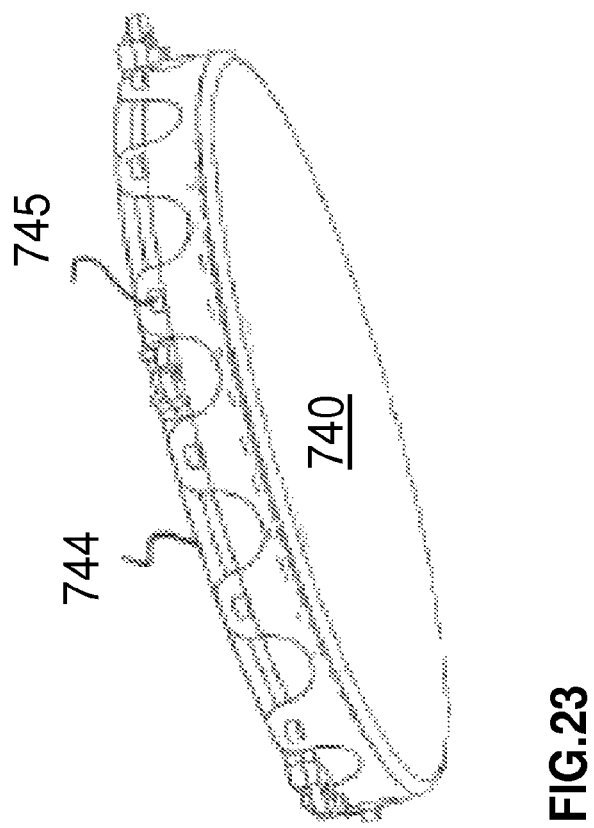
FIG. 23 is a side perspective view of the portion of the lid assembly of FIG. 22.
Figure 24:
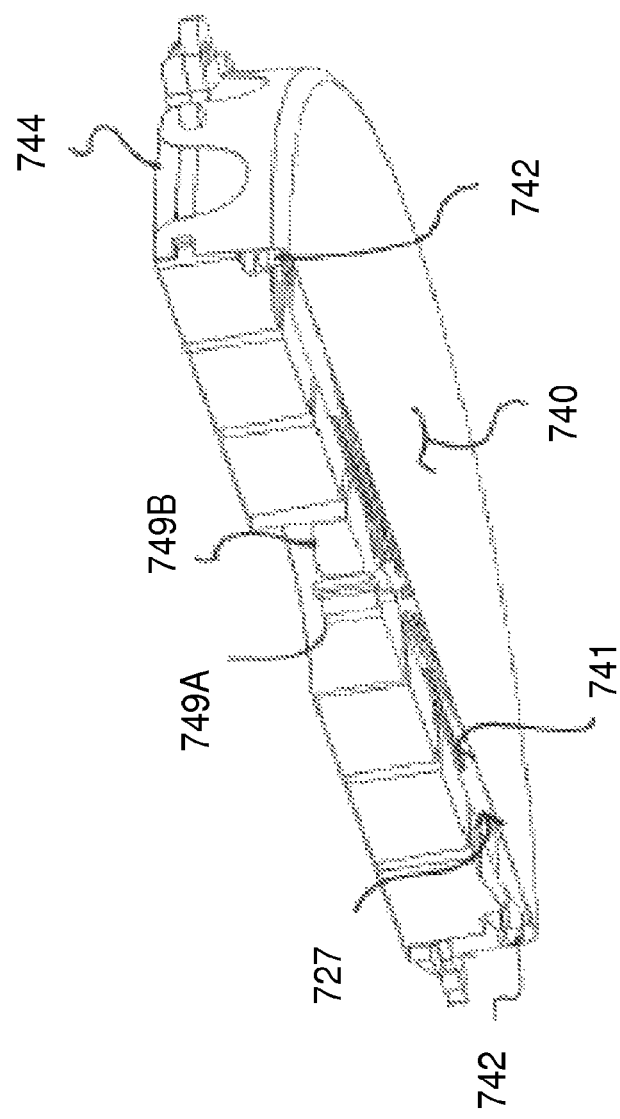
FIG. 24 is a cross-sectional view of the portion of the lid assembly of FIG. 22 taken along line S-S (shown in FIG. 22).

Referring to FIGS. 22-24, at least a portion of the membrane 740 is disposed (e.g., wrapped) about at least a portion of the membrane frame 744. In some embodiments, the membrane 740 is stretched when it is disposed on the membrane frame 744. The membrane 740 is disposed about a lower edge or rim of the membrane frame 744 and over at least a portion of an outer perimeter of the membrane frame 744 such that the membrane 740 is engaged with a series of protrusions (e.g., protrusion 745) configured to help retain the membrane with respect to the membrane frame. The membrane frame 744 is configured to be received in a recess 747 defined by the lid 720 (see, e.g., FIG. 21A). As such, the membrane 740 is engaged between the membrane frame 744 and the lid 720, which facilitates retention of the membrane with respect to the membrane frame. In some embodiments, the first gasket 742 also helps to maintain the membrane 740 with respect to the membrane frame 744 because the first gasket is compressed against the membrane between the membrane frame 744 and the lid 720.

As illustrated in FIG. 20, the membrane 740 is disposed within the pumping chamber 725 at an angle with respect to a horizontal axis A4. In this manner, the membrane 740 is configured to facilitate movement of fluid towards a purge port 706 in fluid communication with the pumping chamber 725, as described in more detail herein. The angle of incline of the membrane 740 can be of any suitable value to allow fluid (e.g., gas bubbles, excess liquid) to flow towards the purge port 706 and exit the pumping chamber 725. In some embodiments, the angle of incline is approximately in the range of 1°-10°, in the range of 2°-6°, in the range of 2.5°-5°, in the range of 4°-5° or any angle of incline in the range of 1°-10° (e.g., approximately 1°, 2°, 3°, 4°, 5° 6°, 7°, 8°, 9°, 10°). More specifically, in some embodiments, the angle of incline is approximately 5°.

The membrane 740 can be of any suitable size and/or thickness, including, for example, a size and/or thickness described with respect to another membrane herein (e.g., membrane 40, 140, 340). The membrane 740 can be constructed of any suitable material. For example, in some embodiments, the membrane is constructed of silicone, plastic, or another suitable material. In some embodiments, the membrane is flexible. As illustrated in FIG. 23, the membrane 740 can be substantially seamless. In this manner, the membrane 740 is configured to be more resistant to being torn or otherwise damaged in the presence of a flexural stress caused by a change in pressure in the pumping chamber due to the inflow and/or release of oxygen or another gas.

Referring to FIG. 20, the lid 720 includes the purge port 706 disposed at the highest portion of the pumping chamber 725 (e.g., at the highest portion or point of the second portion 729 of the pumping chamber 725). The purge port 706 is configured to permit movement of fluid from the pumping chamber 725 to an area external to the self-purging preservation apparatus 700. The purge port 706 can be similar in many respects to a purge port described herein (e.g., port 78, purge ports 106, 306).

Figure 26:
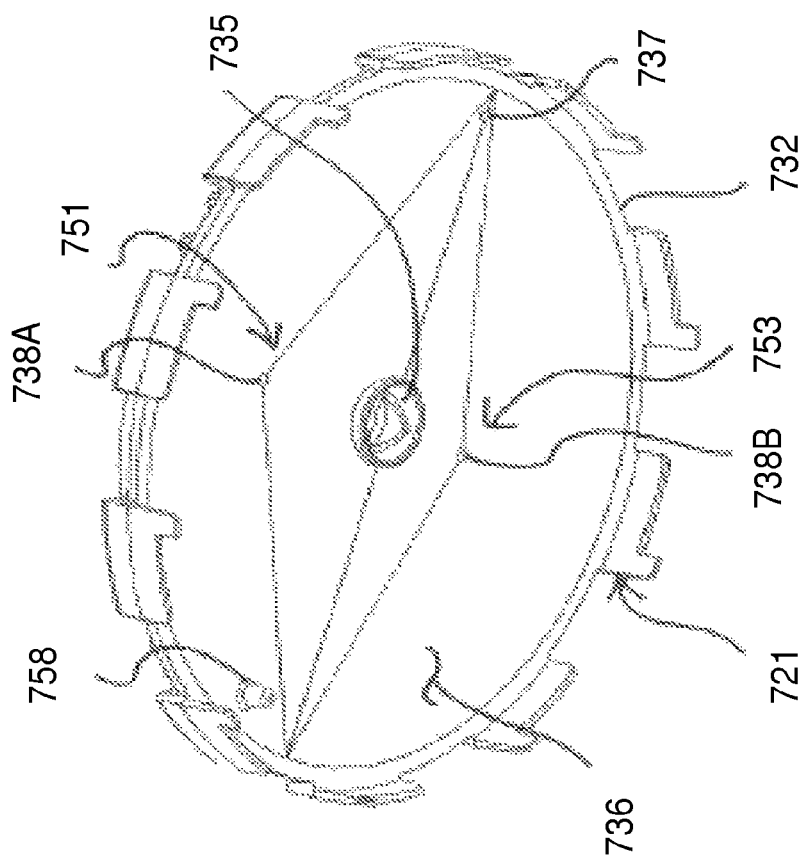
FIG. 26 is a bottom perspective view of the portion of the lid assembly of FIG. 25.

As noted above, the upper surface 734 of the base 732 forms the bottom portion of the pumping chamber 725. Referring to FIGS. 21A and 26, a lower surface 736 of the base 732 forms an upper portion of a tissue chamber 792. The tissue chamber 792 is formed by the canister 790 and the lower surface 736 of the base 732 when the lid assembly 710 is coupled to the canister 790. A well 758 is extended from the lower surface 736 of the base 732 (e.g., into the tissue chamber 792). The well 758 is configured to contain a sensor (not shown) configured to detect the temperature within the tissue chamber 792. The well 758 can be configured to substantially fluidically isolate the sensor from the tissue chamber 792, thereby preventing liquid (e.g., perfusate) from the tissue chamber from engaging the sensor directly. In some embodiments, the sensor contained in the well 758 can be in electrical communication with a control unit (such as control unit 500, described in detail above).

The lower surface 736 of the base 732 defines a first concavely inclined portion 751 and a second concavely inclined portion 753 different from the first portion 751. Said another way, the portions of the base 732 forming each of the first portion 751 and the second portion 753 of the lower surface 736 lie along a plane having an axis different than the horizontal axis A4. For example, each of the first portion 751 and the second portion 753 of the base can be in the shape of an inverted cone. The portions of the lower surface 736 of the base forming the first and second portions 751, 753 can each be inclined with respect to the horizontal axis A4 at an angle equal to or greater than about 5°. Each of the first portion 751 and the second portion 753 of the lower surface 736 of the base 732 define the highest points or portions (i.e., the peak(s)) of the tissue chamber 792 when the self-purging preservation apparatus 700 is in an upright position (as shown in FIG. 20). In this manner, the base 732 is configured to facilitate movement of fluid towards the highest portion(s) of the tissue chamber 792 as the tissue chamber 792 is filled with fluid approaching a maximum volume or maximum fluid capacity of the tissue chamber.

As illustrated in FIG. 21A, valves 738A, 738B, respectively, are disposed at approximately the peak of each of the first portion 751 and the second portion 753, respectively, of the base 732. Because valves 738A, 738B are substantially similar in form and function, only valve 738A is described in detail herein. The valve 738 is moveable between an open configuration and a closed configuration. In its open configuration, the valve 738A is configured to permit movement of fluid from the tissue chamber 792 to the pumping chamber 725 via the valve. Specifically, the valve 738A is configured to permit fluid to move from the tissue chamber 792 into the second portion 729 of the pumping chamber 725. In this manner, an excess amount of fluid within the tissue chamber 792 can overflow through the valve 738A and into the pumping chamber 725. In its closed configuration, the valve 738A is configured to substantially prevent movement of fluid from the pumping chamber 725 to the tissue chamber 792, or vice versa, via the valve. The valve 738A is moved from its closed configuration to its open configuration when a pressure in the tissue chamber 792 is greater than a pressure in the pumping chamber 725. In some embodiments, the valve 738A is moved from its open position to its closed position when a pressure in the pumping chamber 725 is greater than a pressure in the tissue chamber 792. In some embodiments, the valve 738A is biased towards its closed configuration.

The valve 738A can be a ball check valve. The valve 738A is moveable between a closed configuration in which a ball of the valve 738A is disposed on a seat of the valve and an open configuration in which the ball is lifted off of the seat of the valve. The ball of the valve 738A is configured to rise off of the seat of the valve when the pressure in the tissue chamber 792 is greater than the pressure in the pumping chamber 725. In some embodiments, the membrane 740 is positioned in proximity over the valve 738A to prevent the ball from rising too high above the seat such that the ball could be laterally displaced with respect to the seat. The valves 738A, 738B can be similar in many respects to a valve described herein (e.g., valve 138, 338A, 338B). For example, the valves 738A, 738B can include a jet 760A, 760B, respectively, similar in form and/or function as the jets 360A, 360B described in detail above with respect to self-purging preservation apparatus 300. As such, the valves 738A, 738B are not described in more detail herein.

The base 732 is coupled to the lid 720. In some embodiments, the base 732 and the lower portion 723 of the lid 720 are coupled together, e.g., about a perimeter of the pumping chamber 725 (see, e.g., FIGS. 21A and 25). The base 732 and the lid 720 can be coupled using any suitable mechanism for coupling including, but not limited to, a plurality of screws, an adhesive, a glue, a weld, another suitable coupling mechanism, or any combination of the foregoing. A gasket 748 is disposed between the base 732 and the lid 720 (see e.g., FIGS. 20 and 21A). The gasket 748 is configured to seal an engagement of the base 732 and the lid 720 to substantially prevent fluid in the pumping chamber 725 from leaking therebetween. In some embodiments, the gasket 748 is an 0-ring. The gasket 748 can be similar in many respects to a gasket described herein (e.g., gasket 148, 742).

The base 732 defines a lumen 735 configured to be in fluid communication with a lumen 774 of a tissue adapter 770, described in more detail below. The base 732 is configured to permit oxygenated perfusate to move from the pumping chamber 725 through its lumen 735 into the lumen 774 of the tissue adapter 770 towards the tissue chamber 792. In this manner, the lumen 735 of the base 732 is configured to help fluidically couple the pumping chamber 725 and the tissue chamber 792.

Figure 21B:
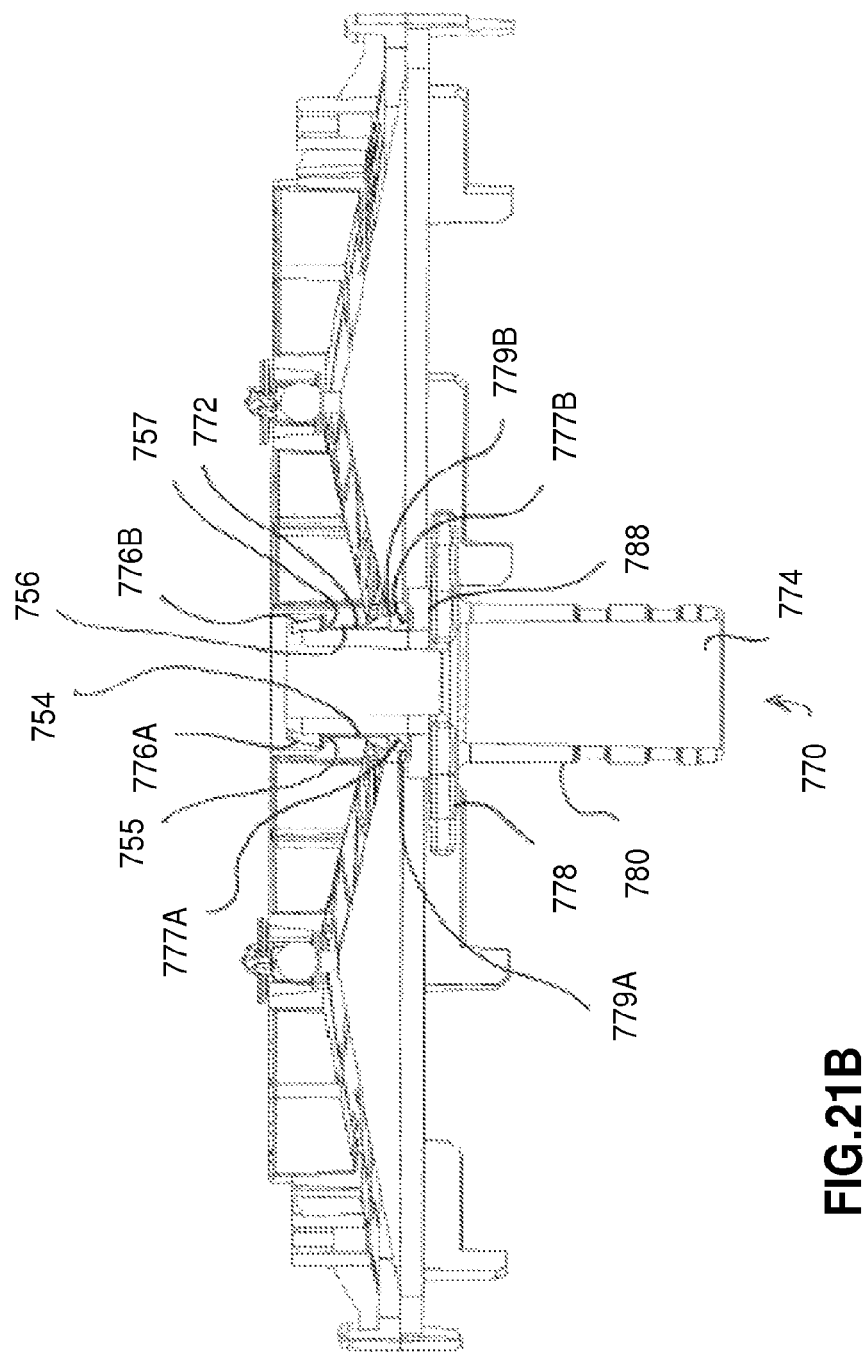
FIG. 21B is an enlarged cross-sectional view of a portion of the lid assembly of the self-purging preservation apparatus of FIG. 21A.

The tissue adapter 770 is configured to substantially retain the tissue with respect to the self-purging preservation apparatus 700. The tissue adapter 770 can be similar in many respects to an adapter described herein (e.g., adapter 26, tissue adapter 170). Referring to FIG. 21B, the tissue adapter 770 includes a handle portion 778, an upper portion 772, and a lower portion 780, and defines the lumen 774 extended therethrough. The upper portion 772 of the tissue adapter 770 is extended from a first side of the handle portion 778. The lower portion 780 of the tissue adapter 770 is extended from a second side of the handle portion 778 different than the first side of the handle portion. In some embodiments, the lower portion 780 is configured to be at least partially inserted into the tissue. More specifically, at least a portion of the lower portion 780 is configured to be inserted into a vessel (e.g., an artery, a vein, or the like) of the tissue. For example, the protrusion 780 can be configured to be at least partially received in a bodily vessel having a diameter within the range of about 3 millimeters to about 8 millimeters. In other embodiments, the lower portion 780 is configured to be coupled to the tissue via an intervening structure (not shown in FIG. 21B) to fluidically couple the lumen 774 of the tissue adapter 770 to a vessel of the tissue. The intervening structure can be, for example, silastic or other tubing. In this manner, the lower portion 780 is configured to deliver the fluid (e.g., the oxygenated perfusate) from the pumping chamber 725 to the vessel of the tissue via the lumen 774 defined by the tissue adapter 770. The vessel of the tissue can be sutured to the lower portion 780 of the adapter 770 and/or to the intervening structure (e.g., tubing).

The upper portion 772 of the tissue adapter 770 is configured to couple the tissue adapter to the base 732 of the lid assembly 710. The upper portion 772 of the tissue adapter is configured to be received by the lumen 735 defined by the base. The upper portion 772 includes a first projection 776A and a second projection 776B spaced apart from the first projection. The projections 776A, 776B of the tissue adapter 770 are configured to be received by the lumen 735 of the base 732 in opposing spaces between a first protrusion 754 and a second protrusion 756 (shown in FIG. 21B) disposed within the lumen of the base. Once the upper portion 772 is received in the lumen 735 of the base 732, the tissue adapter 770 can be rotated approximately ninety degrees such that its first projection 776A and its second projection sit on a shoulder 755, 757, respectively, defined by the protrusions 754, 756, respectively, of the base. The tissue adapter 770 can be rotated in either a clockwise or a counterclockwise direction to align its projections 776A, 776B with the shoulders 755, 757 of the protrusions 754, 756 of the base 732. Similarly, the tissue adapter 770 can be rotated in either the clockwise or the counterclockwise direction to unalign its projections 776A, 776B with the shoulders 755, 757 of the protrusions 754, 756 of the base 732, such as for decoupling of the adapter from the base. Said another way, the tissue adapter 770 can be configured to be coupled to the base 732 with a bayonet joint. The handle portion 778 is configured to facilitate coupling and decoupling of the tissue adapter 770 and the base 732. For example, the handle portion 778 is configured to be grasped by a hand of an operator of the self-purging preservation apparatus 700. The handle portion 778 can be substantially disc-shaped, and includes a series of recesses configured to facilitate grasping the handle portion with the operator's hand and/or fingers.

In some embodiments, the upper portion 772 of the tissue adapter 770 includes a set of protrusions spaced apart (e.g., vertically offset) from projections 776A, 776B. For example, as shown in FIG. 21B, protrusions 777A, 777B are disposed at opposing portions of an outer perimeter of the upper portion 772 of the tissue adapter 770. The protrusions 777A, 777B can each be configured to be received in a recess 779A, 779B, respectively, defined by the base 732. In some embodiments, the protrusions 777A, 777B are configured to retain a gasket 788 disposed about the upper portion 772 of the tissue adapter 770 between the handle portion 778 of the adapter and the base 732. The gasket 788 is configured to substantially prevent a fluid from flowing between the pumping chamber 725 and the tissue chamber 792 within a channel formed between an outer surface of the upper portion 772 of the tissue adapter 770 and an inner surface of the lumen 735 of the base 732. In some embodiments, the gasket 788 is compressed between the tissue adapter 770 and the base 732 when the tissue adapter is coupled to the base. The gasket 788 can be similar in many respects to a gasket described herein (e.g., gasket 188, 742).

Figure 25:
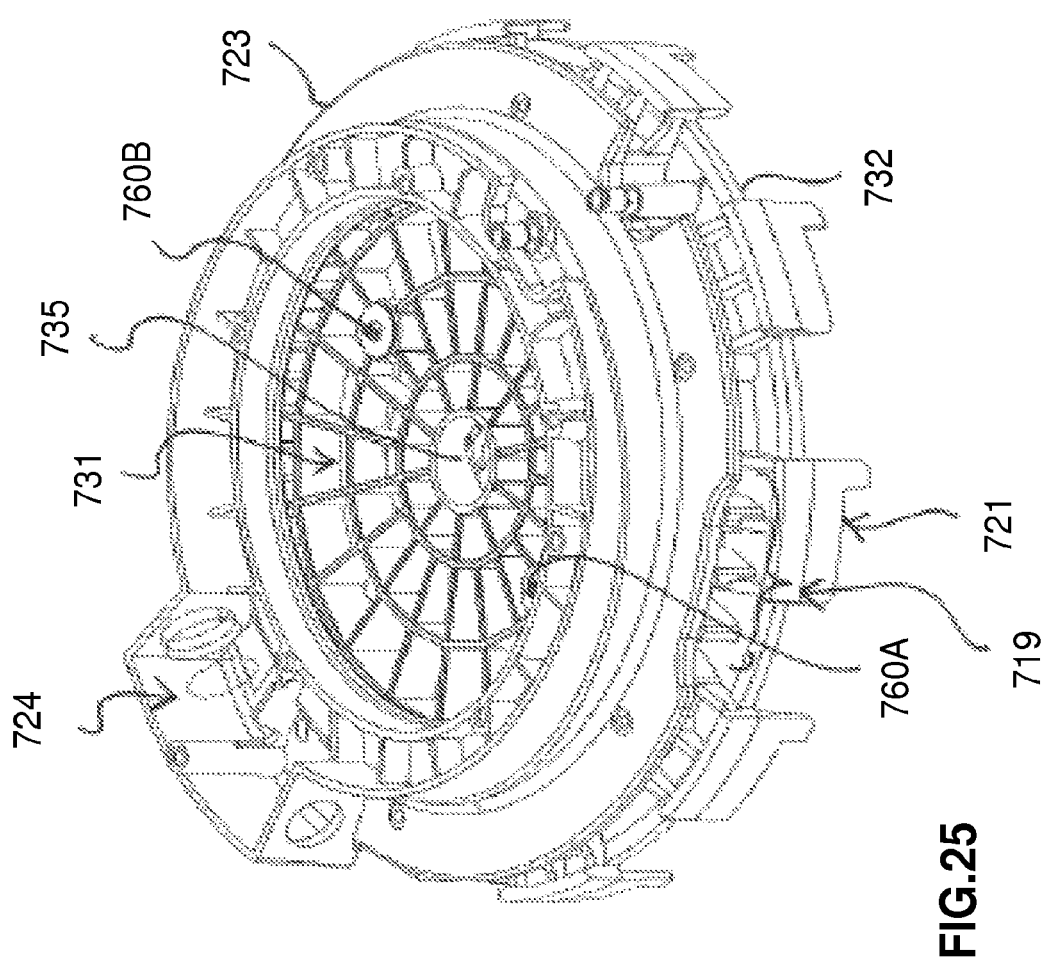
FIG. 25 is a top perspective view of a portion of the lid assembly of the self-purging preservation apparatus of FIG. 19.

In some embodiments, at least a portion of the lid assembly 710 is configured to minimize flexure of the portion of the lid assembly, such as may occur in the presence of a positive pressure (or pulse wave) caused by introduction of oxygen into the pumping chamber 725 and/or of oxygenated perfusate into the tissue chamber 792. For example, as illustrated in FIG. 21A, an upper portion 722 of the lid 720 includes a plurality of ribs 726 configured to minimize flexure of the lid 720 in response to externally applied loads, for example, if an operator presses down on the lid 720. In other words, the plurality of ribs 726 structurally reinforces the lid 720 to help prevent the lid 720 from flexing. In another example, as illustrated in FIG. 22, an upper portion of the membrane frame 744 can include ribs 746 configured to reinforce the top of the pumping chamber 725 to help prevent flexure of the top of the pumping chamber 725 during pumping of oxygen through the lid assembly 710. In yet another example, the base 732 is configured to substantially minimize flexure of the base, such as may occur in the presence of a positive pressure caused by the introduction of oxygen into the pumping chamber 725 and/or of oxygenated perfusate into the tissue chamber 792. As illustrated in FIG. 25, the base 732 includes a plurality of ribs 731 extended from its upper surface. The plurality of ribs 731 is configured to reinforce the base 732, which helps to minimize flexure of the base. The plurality of ribs (e.g., ribs 726, 746, and/or 731) can be in any suitable configuration, including, for example, a circular configuration, a hub-and-spoke combination, a parallel configuration, or the like, or any suitable combination thereof. For example, as shown in FIGS. 21A, 22 and 25, the plurality of ribs (e.g., ribs 726, 746, 731) are a combination of circular and hub-and-spoke configurations.

Referring to FIG. 20, the lid assembly 710 includes a fill port 708 configured to permit introduction of a fluid (e.g., the perfusate) into the tissue chamber 792 (e.g., when the lid assembly 710 is coupled to the canister 790). The fill port 708 can be similar in many respects to a port described herein (e.g., port 74, fill port 108). In the embodiment illustrated in FIG. 20, the fill port 708 includes a fitting 707 coupled to the lid 720 and defines a lumen 709 in fluidic communication with a lumen 737 defined by the base 732, which lumen 737 is in fluidic communication with the tissue chamber 792. The fitting 707 can be any suitable fitting, including, but not limited to, a luer lock fitting. The fill port 708 can include a cap 705 removably coupled to the port. The cap 705 can help prevent inadvertent movement of fluid, contaminants, or the like through the fill port 708.

Figure 28A:
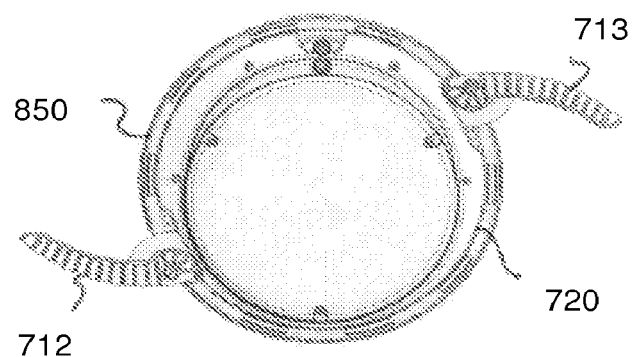
FIGS. 28A-28C are top perspective views of the lid assembly and the coupling mechanism of the self-purging preservation apparatus of FIG. 19 in a first configuration, a second configuration, and a third configuration, respectively.
Figure 28B:
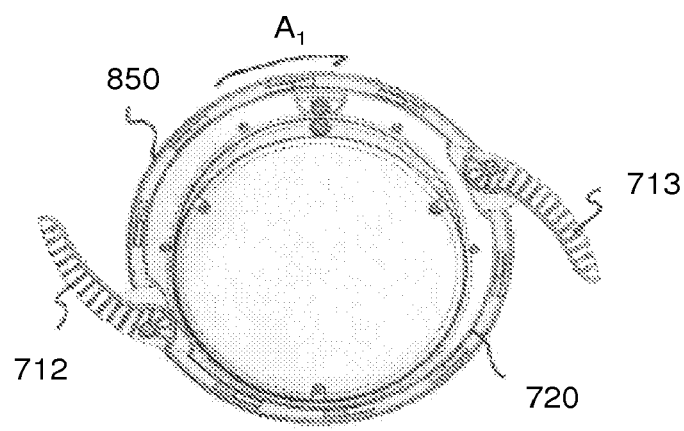
Figure 28C:
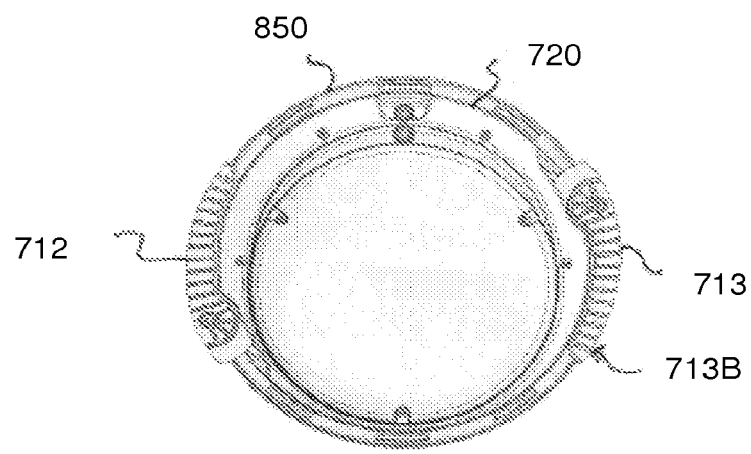

The lid assembly 710 is configured to be coupled to the canister 790. The lid assembly 710 includes handles 712, 713. The handles 712, 713 are each configured to facilitate coupling the lid assembly 710 to the canister 790, as described in more detail herein. Said another way, the handles 712, 713 are configured to move between a closed configuration in which the handles prevent the lid assembly 710 being uncoupled or otherwise removed from the canister 790, and an open configuration in which the handles do not prevent the lid assembly 710 from being uncoupled or otherwise removed from the canister. The handles 712, 713 are moveably coupled to the lid 720. Each handle 712, 713 can be pivotally coupled to opposing sides of the coupling mechanism 850 (described in more detail herein) disposed about the lid 720. For example, each handle 712, 713 can be coupled to the coupling mechanism 850 via an axle (not shown). Each handle includes a series of gear teeth (not shown) configured to engage a series of gear teeth 719 (see, e.g., FIG. 25) disposed on opposing sides of the lid 720 as the handles 712, 713 each pivot with respect to the coupling mechanism 850, thus causing rotation of the coupling mechanism 850, as described in more detail herein. In some embodiments, the handles 712, 713 include webbing between each tooth of the series of gear teeth, which is configured to provide additional strength to the respective handle. In their closed configuration, the handles 712, 713 are substantially flush to the coupling mechanism 850. In some embodiment, at least one handle 712 or 713 includes an indicia 713B indicative of proper usage or movement of the handle. For example, as shown in FIG. 28C, the handle 713 includes indicia (i.e., an arrow) indicative of a direction in which the handle portion can be moved. As also shown in FIG. 28C, in some embodiments, the handles 712, 713 include a ribbed portion configured to facilitate a grip by a hand of an operator of the self-purging preservation apparatus 700.

The canister 790 can be similar in many respects to a canister described herein (e.g., canister 32, 190, 390). As shown in FIG. 29, the canister 790 includes a wall 791, a floor (also referred to herein as "bottom") 793, and a compartment 794 defined on its sides by the wall and on its bottom by the floor. The compartment 794 can form a substantial portion of the tissue chamber 792.

Figure 27A:
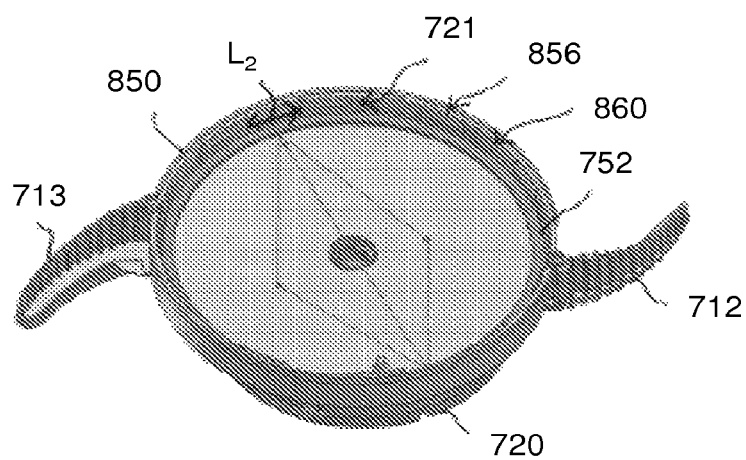
FIGS. 27A-27C are bottom perspective views of the lid assembly, a coupling mechanism, and a canister of the self-purging preservation apparatus of FIG. 19 in a first configuration, a second configuration, and a third configuration, respectively.
Figure 27B:
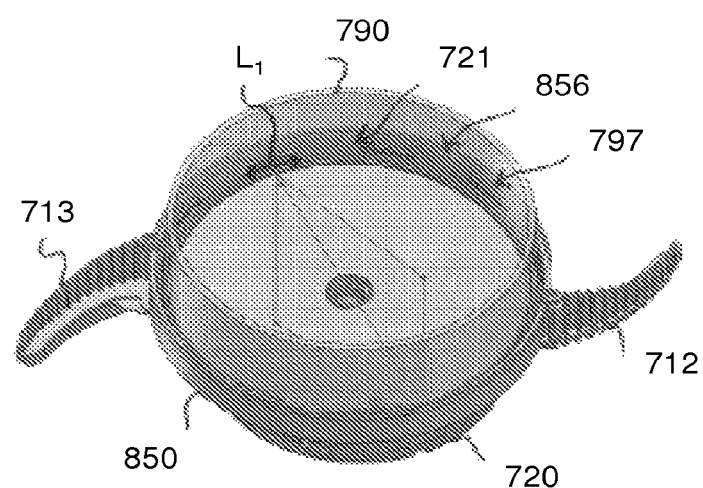
Figure 27C:
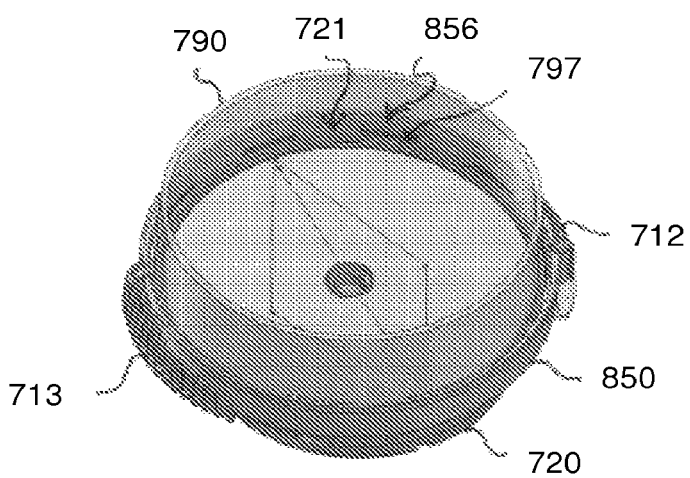

As shown in FIGS. 27A-27C, at least a portion of the canister 790 is configured to be received in the lid assembly 710 (e.g., the base 732). The canister 790 includes one or more protruding segments 797 disposed adjacent, or at least proximate, to an upper rim 795 of the canister. Each segment 797 is configured to protrude from an outer surface of the canister 790 wall 791. The segments 797 are configured to help properly align the canister 790 with the lid assembly 710, and to help couple the canister 790 to the lid assembly 710. Each segment 797 is configured to be received between a pair of corresponding segments 721 of the lid 720, as shown in FIG. 27B. A length $L_1$ of the segment 797 of the canister 790 is substantially equivalent to a length 1.2 (see, e.g., FIG. 27A) of an opening 860 between the corresponding segments 721 of the lid 720. In this manner, when the segment 797 of the canister 790 is received in the corresponding opening of the lid 720, relative rotation of the canister 790 and lid 720 with respect to each other is prevented. The canister 790 can include any suitable number of segments 797 configured to correspond to openings between protruding segments 721 of the lid 720. For example, in the embodiment illustrated in FIG. 27B (and also shown in FIG. 29), the canister 790 includes ten segments 797, each of which is substantially identical in form and function, spaced apart about the outer perimeter of the canister 790 adjacent the upper rim 795. In other embodiments, however, a canister can include less than or more than ten segments.

A gasket 752 is disposed between the base 732 and the upper rim 795 of the wall 791 of the canister 790. The gasket 752 is configured to seal the opening between the base 732 and the wall 791 of the canister 790 to substantially prevent flow of fluid (e.g., the perfusate) therethrough. The segments 797 of the canister 790 are configured to engage and compress the gasket 752 when the canister 790 is coupled to the lid 720. The gasket 752 can be any suitable gasket, including, for example, an O-ring.

The floor 793 of the canister 790 is configured to flex when a first pressure within the tissue chamber 792 changes to a second pressure within the tissue chamber, the second pressure different than the first pressure. More specifically, in some embodiments, the floor 793 of the canister 790 is configured to flex outwardly when a first pressure within the tissue chamber 792 is increased to a second pressure greater than the first pressure. For example, the floor 793 of the canister 790 can be configured to flex in the presence of a positive pressure (or a pulse wave) generated by the pumping of the oxygenated perfusate from the pumping chamber 725 into the tissue chamber 792, as described in detail above with respect to self-purging preservation apparatus 100. In some embodiments, the floor 793 of the canister 790 is constructed of a flexible membrane. The floor 793 of the canister 790 can have any suitable thickness T, including, for example, a thickness described above with respect to floor 193 of canister 190. In some embodiments, the floor 793 has a thickness T equal to or greater than 0.100 inches.

The canister 790 can be configured to enable an operator of the self-purging preservation apparatus 700 to view the tissue when the tissue is sealed within the tissue chamber 792. In some embodiments, for example, at least a portion of the canister 790 (e.g., the wall 791) is constructed of a clear or transparent material. In another example, in some embodiments, at least a portion of the canister 790 (e.g., the wall 791) is constructed of a translucent material. In yet another example, in some embodiments, a canister includes a window through which at least a portion of the tissue chamber can be viewed.

As noted above, the coupling mechanism 850 is configured to couple the canister 790 to the lid assembly 710. In the embodiment illustrated in FIGS. 19-29, the coupling mechanism 850 is a retainer ring. The retainer ring 850 is configured to be disposed about a lower rim of the lid 720 and the upper rim 795 of the canister 790. An upper portion of the retainer ring 850 can be wrapped over a portion of the lid assembly 710 (e.g., an upper perimeter edge of the base 732), as shown in FIG. 20. In this manner, compression of gasket 752 is improved when the lid assembly 710 is coupled to the canister 790 by the retainer ring 850, as described in more detail below. The retainer ring 850 can be of any suitable size for being disposed about the lid 720 and the canister 790. For example, in some embodiments, the retainer ring 850 can be 22.35 cm (or about 8.80 inches) in diameter.

A plurality of segments 856 are extended from an inner surface of the retainer ring 850 at spaced apart locations about an inner perimeter of the retainer ring. Each segment of the plurality of segments 856 is configured to be aligned with a segment 721 of the lid 720 when the retainer ring 850 is coupled to the lid 720, and the handles 712, 713 of the lid assembly 710 are in the open configuration. In some embodiments, as shown in FIG. 27A, each segment of the plurality of segments 856 of the retainer ring 850 is configured to laterally abut an inner portion of an L-shaped portion of the corresponding segment 721 of the lid 720 when the retainer ring 850 is disposed on the lid assembly 710 and the handles 712, 713 of the lid assembly 710 are in the open configuration, which facilitates accurate alignment of the lid 720 and the retainer ring 850. Accordingly, when the lid 720 and the retainer ring 850 are aligned and the handles 712, 713 of the lid assembly 710 are in the open configuration, the aligned segments 721 of the lid 720 and segments 856 of the retainer ring 850 collectively define the openings 860 configured to receive the segments 797 of the canister 790, described above.

To couple, or otherwise secure, the canister 790 to the lid assembly 710 using the retainer ring 850, the handles 712, 713 of the lid assembly are moved from their open configuration (see, e.g., FIGS. 27B and 28A) through an intermediate configuration (see, e.g., FIG. 28B) to their closed configuration (see, e.g., FIGS. 27C and 28C). As the handles 712, 713 are moved from their open configuration towards their closed configuration, the retainer ring 850 is rotated in a first direction (as shown by arrow A1 in FIG. 28B) with respect to each of the canister 790 and the lid assembly 710. Accordingly, as shown in FIG. 27C, when the handles 712, 713 are in their closed configuration, the segments 856 of the retainer ring 850 are vertically aligned with the segments 797 of the canister 790, e.g., such that each segment of the retainer ring is disposed beneath a corresponding segment 797 of the canister 790 when the self-purging preservation apparatus 700 is in the upright position. Over-rotation of the retainer ring 850 with respect to the lid assembly 710 and the canister 790 is prevented by an outer edge of the L-shaped portion of the lid 720 segments 721. To decouple the lid assembly 710 from the canister 790, the handles 712, 713 are moved from their closed configuration to their open configuration, thus causing rotation of the retainer ring 850 relative to the lid assembly and the canister in a second direction opposite the first direction. During decoupling, over rotation of the retainer ring 850 with respect to the lid assembly 710 and the canister 790 is prevented because the segments 856 of the retainer ring will each laterally abut the inner portion of the L-shaped portion of the corresponding segment 721 of the lid 720.

As noted above, the self-purging preservation apparatus 700 is configured for controlled delivery of fluid (e.g., oxygen) from an external source (not shown) into the pumping chamber 725 of the lid assembly 710. The external source can be, for example, an oxygen cylinder. In some embodiments, the self-purging preservation apparatus 700 includes the pneumatic system, such as pneumatic system 200, configured for controlled venting of fluid (e.g., carbon dioxide) from the pumping chamber 725 to an area external to the self-purging preservation apparatus 700 (e.g., to the atmosphere). The pneumatic system 200 is moveable between a first configuration in which the pneumatic system is delivering fluid to the pumping chamber 725 and a second configuration in which the pneumatic system is venting fluid from the pumping chamber 725. The pneumatic system 200 is described in detail above with respect to self-purging preservation apparatus 100.

In use, the tissue is coupled to at least one of the tissue adapter 770 or tubing configured to be coupled to the tissue adapter. The tissue adapter 770 can be coupled to the lid assembly 710. Optionally, a desired amount of perfusate can be disposed within the compartment 794 of the canister 790 prior to disposing the lid assembly 710 on the canister. For example, in some embodiments, a perfusate line (not shown) is connected to the tissue adapter 770 and the tissue is flushed with perfusate, thereby checking for leaks and partially filling the canister 790 with perfusate. Optionally, when the canister 790 is substantially filled, the perfusate line can be disconnected. The lid assembly 710 is disposed on the canister 790 such that the tissue is received in the tissue chamber 792. The lid assembly 710 is coupled to the canister 790. Optionally, the lid assembly 710 and the canister 790 are coupled via the retainer ring 850. Optionally, a desired amount of perfusate is delivered to the tissue chamber 792 via the fill port 708. In some embodiments, a volume of perfusate greater than a volume of the tissue chamber 792 is delivered to the tissue chamber such that the perfusate will move through the valves 738A, 738B into the second portion 729 of the pumping chamber 725.

A desired control scheme of the pneumatic system 200 is selected. Oxygen is introduced into the first portion 727 of the pumping chamber 725 via the pneumatic system 200 based on the selected control scheme. The pneumatic system 200 is configured to generate a positive pressure by the introduction of oxygen into the first portion 727 of the pumping chamber 725. The positive pressure helps to facilitate diffusion of the oxygen through the membrane 740. The oxygen is diffused through the membrane 740 into the perfusate disposed in the second portion 729 of the pumping chamber 725, thereby oxygenating the perfusate. Because the oxygen will expand to fill the first portion 727 of the pumping chamber 725, substantially all of an upper surface 741 of the membrane 740 which faces the first portion of the pumping chamber can be used to diffuse the oxygen from the first portion into the second portion 729 of the pumping chamber.

As the tissue uses the oxygen, the tissue will release carbon dioxide into the perfusate. Such carbon dioxide can be diffused from the second portion 729 of the pumping chamber 725 into the first portion 727 of the pumping chamber 725. Carbon dioxide within the first portion 727 of the pumping chamber is vented via a control line (not shown) to a valve (not shown), and from the valve through a vent line (not shown) to the atmosphere external to the self-purging preservation apparatus 700.

The positive pressure also causes the membrane 740 to flex, which transfers the positive pressure in the form of a pulse wave into the oxygenated perfusate. The pulse wave generated by the pumping chamber is configured to facilitate movement of the oxygenated perfusate from the second portion 729 of the pumping chamber 725 into the tissue via the tissue adapter 770 (and any intervening structure or tubing), thus perfusing the tissue. In some embodiments, the pumping chamber 725 is configured to generate a pulse wave in a similar manner as pumping chamber 125, described in detail above with respect to self-purging preservation apparatus 100.

At least a portion of the perfusate perfused through the tissue is received in the tissue chamber 792. In some embodiments, the pulse wave is configured to flow through the perfusate disposed in the tissue chamber 792 towards the floor 793 of the canister 790. The floor 793 of the canister 790 is configured to flex when engaged by the pulse wave. The floor 793 of the canister 790 is configured to return the pulse wave through the perfusate towards the top of the tissue chamber 792 as the floor 793 of the canister 790 is returned towards its original non-flexed position. In some embodiments, the returned pulse wave is configured to generate a sufficient pressure to open the valves 738A, 738B disposed at the highest positions in the tissue chamber 792. In this manner, the returned pulse wave helps to move the valves 738A, 738B to their respective open configurations such that excess fluid (e.g., carbon dioxide released from the tissue and/or the perfusate) can move through the valves from the tissue chamber 792 to the pumping chamber 725. The foregoing perfusion cycle can be repeated as desired, including in any manner described above with respect to other self-purging preservation apparatus described herein (e.g., self-purging preservation apparatus 10, 100, 300).

Although the perfusion cycle has been described herein as including a substantially regular intermittent pulse of oxygen from the pneumatic system 200 to the pumping chamber 725, in other embodiments, the pneumatic system 200 can be configured to deliver oxygen to the pumping chamber 725 at a different interval (e.g., flow interval), such as those variations described above with respect to self-purging preservation apparatus 100 and pneumatic system 200.

Although the lid assembly 710 has been illustrated and described as being configured for use with the canister 790, in other embodiments, the lid assembly 710 can be configured for use with canisters having different configurations. For example, although the canister 790 has been illustrated and described herein as being of a certain size and/or shape, in other embodiments, a canister having any suitable dimensions can be configured for use with the lid assembly 710. In some embodiments, for example, a first canister configured for use with the lid assembly 710 is dimensionally configured to accommodate a first type of tissue, and a second canister configured for use with the lid assembly 710 is dimensionally configured to accommodate a second type of tissue different than the first type of tissue. For example, the canister 790 illustrated in FIG. 29 and described herein with respect to apparatus 700 can be dimensioned to accommodate the first tissue, such as a foot. The canister 790 can be, for example, a 2.7 liter cylindrical canister having a height greater than or substantially equal to a width of the floor 793. For example, as shown in FIG. 29, the compartment 794 of the canister 790 can have a height $H_1$ of about 15 cm (or about 5.91 inches) and a diameter $D_1$ of about 15 cm (note that diameter $D_1$ of the compartment 794 can be different from a diameter $D_3$ of the top rim 795 of the canister 790, which can be about 20 cm (or about 7.87 inches)). Accordingly, when the canister 790 is coupled to the lid assembly 710, the apparatus 700 can have an overall diameter of about 24 cm (or about 9.44 inches) and an overall height of about 22.3 cm (or about 8.77 inches).

In another embodiment, as illustrated in FIG. 30, a differently dimensioned canister 990 can be used with the lid assembly 710. The canister 990 can be dimensioned to accommodate the second tissue, such as a limb. The canister 990 can be, for example, a 3.0 liter cylindrical canister having a wall 991 height less than a width of a floor 993 of the canister. For example, as shown in FIG. 30, the compartment 994 of the canister 990 can have a height 112 less than the height $H_1$ of canister 790 and a diameter $D_2$ greater than or equal to the diameter $D_1$ i of canister 790. The height $H_2$ and diameter $D_2$ of the compartment 994 can be such that the lid assembly 710 coupled to the canister 990 via the retainer ring 850 collectively have an overall height of about 16.5 cm (or about 6.48 inches) and a diameter of about 24 cm (or about 9.44 inches). It should be noted that although specific dimensions are described herein, in other embodiments, such dimensions can be different and still be within the scope of the invention. The thickness of the floor 993 of the canister 990 can be selected based on the height and width dimensions of the canister 990 to ensure that the floor 993 is configured to properly flex in the presence of the pulse wave, as described above, and may be the same as or different than the thickness of the floor 793 of canister 790. The canister 990 includes a plurality of segments 997 protruding from an outer surface of the wall adjacent an upper rim 995 of the canister 990. The plurality of segments 997 are configured to facilitate coupling the canister 990 to the lid assembly 710 and the retainer ring 850, as described above with respect to the canister 790.

Referring to FIG. 31, in some embodiments, a self-purging preservation apparatus includes a basket 870 configured to be disposed in a compartment 994 of the canister 990. The basket 870 is configured to support the tissue (e.g., kidney, K) within the compartment 994. In some embodiments, for example, the basket 870 includes a bottom portion 872 on which the tissue can be disposed. In some embodiments, the bottom portion 872 of the basket 870 is smooth. The bottom portion 872 can be slightly curved to accommodate curvature of the tissue. In some embodiments, netting (not shown) can be used to retain the tissue with respect to the basket 870 (e.g., when the tissue is disposed on the bottom portion 872 of the basket 870). Arms 874A, 874B are disposed on a first side of the bottom portion 872 of the basket 870 opposite arms 876A, 876B disposed on a second side of the bottom portion of the basket. Each pair of arms 874A, 874B and 876A, 876B is extended vertically and terminates in a handle portion 875, 877, respectively, that couples the upper end portions of the arms.

In some embodiments, as shown in FIG. 31, a shape of the outer perimeter of the bottom portion 872 of the basket 870 can substantially correspond to a shape of a perimeter of the canister 990, such that outer edges of lower end portions of the arms 874A, 874B, 876A, 876B each abut an inner surface of the wall 991 of the canister. In this manner, lateral movement of the basket 871, and thus of the tissue supported thereon, is prevented, or at least restricted. The handle portions 875, 877 can be configured to engage the lower surface 736 of the base 732 of the lid assembly 710 when the basket 870 is received in the canister's 990 compartment 994 and the canister is coupled to the lid assembly 710. In this manner, vertical movement of the basket 870 with respect to the canister 990 is prevented.

While various embodiments have been described above, it should be understood that they have been presented by way of example only, and not limitation. Where methods described above indicate certain events occurring in certain order, the ordering of certain events may be modified. For example, selecting the control scheme of the pneumatic system 200 can occur before the coupling the tissue to the tissue adapter 170, 770. Additionally, certain of the events may be performed concurrently in a parallel process when possible, as well as performed sequentially as described above. Furthermore, although methods are described above as including certain events, any events disclosed with respect to one method may be performed in a different method according to the invention. Thus, the breadth and scope should not be limited by any of the above-described embodiments.

While the invention has been particularly shown and described with reference to specific embodiments thereof, it will be understood that various changes in form and details may be made. For example, although the valves 138, 738A, 738B disposed at the highest portion of the tissue chamber 192, 792 have been illustrated and described herein as being a ball check valve, in other embodiments, a different type of valve configured to permit unidirectional flow of a fluid from the tissue chamber into the pumping chamber can be included in the self-purging preservation apparatus. For example, in some embodiments, a self-purging preservation apparatus includes a different type of a check valve, such as a diaphragm check valve, a swing check valve, a life check valve, or the like. In another example, in some embodiments, a self-purging preservation apparatus includes a valve that is different than a check valve.

Although the valve 210 of the pneumatic system 200 has been illustrated and described herein as being a solenoid valve, in other embodiments, the pneumatic system can include a different type of valve configured to control the flow of oxygen into the pumping chamber.

Although the valve 210 of the pneumatic system 200 has been illustrated and described herein as including three ports, in other embodiments, a valve of a pneumatic system can include a different number of ports. For example, in some embodiments, the valve includes one, two, four, or more ports.

Although the pneumatic systems (e.g., pneumatic system 200, 220) have been illustrated and described as including a specific number of control orifices (e.g., one control orifice 207 and two control orifices 223, 225, respectively), in other embodiments, a pneumatic system can include any suitable number of control orifices. For example, a pneumatic system can include one, two, three, four, or more control orifices.

Although the lid assemblies described herein (e.g., lid assembly 110, 710) have been illustrated and described as being reinforced by a plurality of ribs (e.g., plurality of ribs 126, 131, 133, 726, 731) having a certain configuration (e.g., a parallel configuration or a combination circular/spoke and wheel configuration), in other embodiments, the lid assembly can include a plurality of ribs having a different orientation. For example, in another embodiment, any of the plurality of ribs can have a grid configuration, a diamond configuration, a herringbone configuration, a spoke and wheel configuration, another suitable configuration, or any combination of the foregoing configurations. Additionally, although lid assembly 110 has been illustrated and described herein as including a plurality of ribs (e.g., plurality of ribs 126, 131, 133) in a parallel configuration in a first direction, in other embodiments, the plurality of ribs can have a parallel configuration in a different direction. For example, although the plurality of ribs 131 are illustrated as having a parallel orientation in a first direction and the plurality of ribs 133 are illustrated as having a parallel orientation in a second direction substantially orthogonal to the first direction, in some embodiments, the plurality of ribs on each of an upper surface and a lower surface of a base can be oriented in a different manner. For example, in some embodiments, a plurality of ribs on an upper surface of a base have a parallel orientation in a first direction and a plurality of ribs on a lower surface of the base have a parallel orientation also in the first direction.

In another example, although the lid assemblies are illustrated and described herein (e.g., lid assembly 110, 710) have been illustrated and described as being reinforced by a plurality of ribs (e.g., plurality of ribs 126, 131, 133, 726, 731), in other embodiments, a lid assembly can include a different mechanism for reinforcement.

Figure 32:
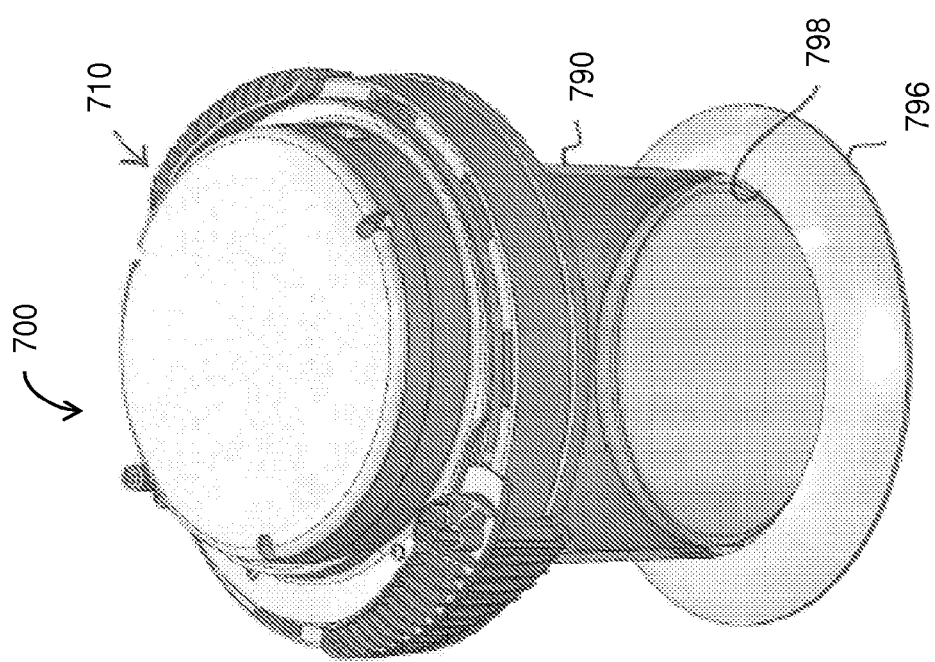
FIG. 32 is a perspective view of the self-purging preservation apparatus of FIG. 19.

In some embodiments, a self-purging preservation apparatus described herein can include components in addition to those described above. For example, referring to FIG. 32, in some embodiments, the self-purging preservation apparatus 700 includes a base 796 configured to be coupled to the canister 790. In some embodiments, the canister 790 and the base 796 are removably coupleable. The canister 790 can be coupled to the base using any suitable coupling mechanism, including, for example, a resistance fit, mating threads, an adhesive, or other suitable coupling mechanism. In the embodiment illustrated in FIG. 32, an upper surface of the base 796 defines a recess 798 configured to receive a bottom portion of the canister 790. The base 796 is configured to provide stability to the canister 790 when the canister 790 is coupled thereto and/or received in the recess 798 of the base 796. In other words, the base 796 is configured to help maintain the canister 790 in an upright position. In some embodiments, the base has a width substantially equal to an overall width of the lid assembly 710. In this manner, the stability provided by the base 796 helps to off-set any top-heaviness imparted to the self-purging preservation apparatus 700 by the lid assembly 710. The base 796 is also configured to protect the floor 793 of the canister 790 when the floor 793 is flexed due to a pressure change within the tissue chamber 792, as described above.

Figure 33:
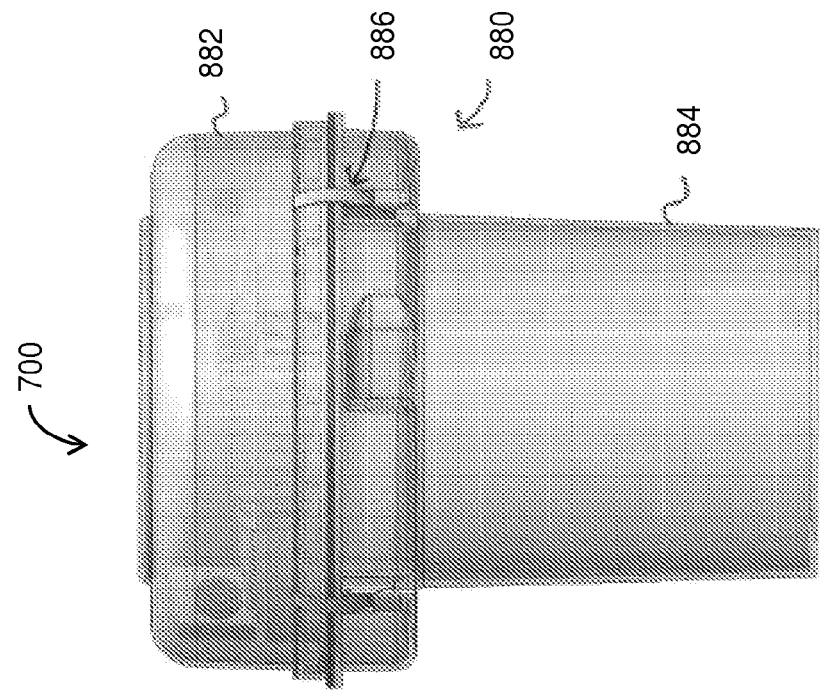
FIG. 33 is a front view of a carrier assembly for use with the self-purging preservation apparatus of FIG. 19.

In another example, the self-purging preservation apparatus 700 can include a sterile carrier assembly 880, as illustrated in FIG. 33. The carrier assembly 880 includes a top portion 882, a bottom portion 884 and a plurality of latches 886 configured to couple the top portion 882 of the carrier assembly 880 to the bottom portion 884 of the carrier assembly 880. The carrier assembly 880 is configured to receive the self-purging preservation apparatus 700 (i.e., the coupled lid assembly 710, retainer ring 850 and canister 790) in a compartment (not shown) defined by the top and bottom portions 882, 884 of the carrier assembly 880. The carrier assembly 880 is configured to protect the self-purging preservation apparatus 700 contained therein, including ensuring that the sterility of the self-purging preservation apparatus 700 contained therein is not compromised when the self-purging preservation apparatus 700 is removed from a sterile field. In this manner, the carrier assembly 880 facilitates transportability of the self-purging preservation apparatus 700.

In another example, in some embodiments, a self-purging preservation apparatus described herein (e.g., self-purging preservation apparatus 10, 100, 300, 700) includes at least one sensor (not shown) configured to detect information associated with the tissue, such as a measurement associated with the tissue. For example, the self-purging preservation apparatus may comprise oxygen sensors allowing the self-purging preservation apparatus to determine an oxygen consumption rate for the tissue. The self-purging preservation apparatus can include a display configured to display an output based on the information detected by the at least one sensor. For example, in some embodiments, the lid 112 of the lid assembly 110 includes a display configured to display a message in real-time based on a measurement associated with the tissue detected by the at least one sensor. The lid 112 of the lid assembly 110 may also include an indicator of the health of the tissue based upon the measurements from the sensors.

Figure 34:
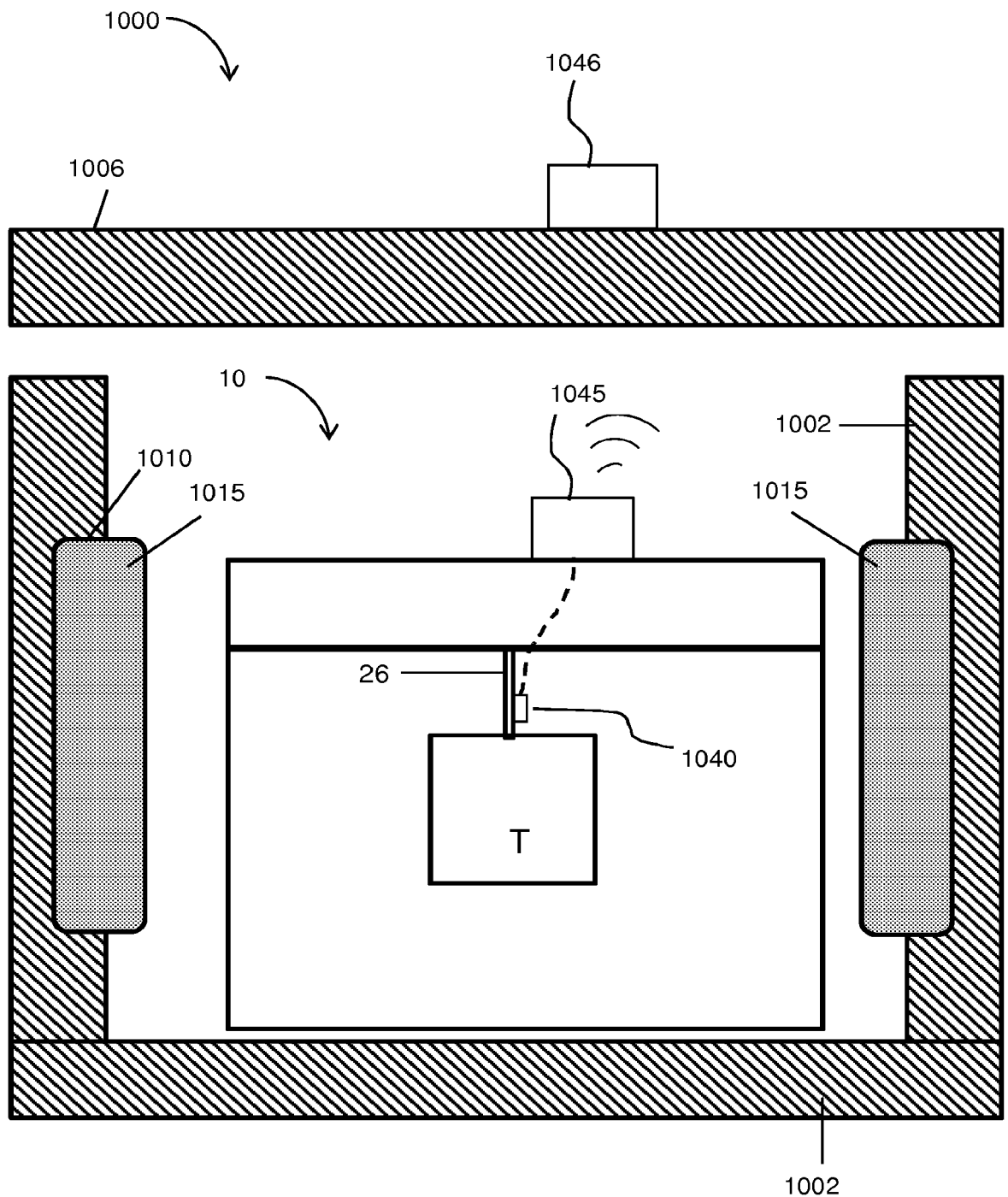
FIG. 34 shows an embodiment of a hypothermic transport system of the invention, including a self-purging preservation apparatus, an insulated transport container, and cooling media for maintaining the temperature of the tissue being transported.

As shown in FIG. 34, an embodiment including an insulated transport container, the temperature sensor 1040 may be any temperature reading device that can be sterilized and maintained in cold fluidic environment, i.e., the environment within the static self-purging preservation apparatus during transport of tissue T. The temperature sensor 1040 may be a thermocouple, thermistor, infrared thermometer, or liquid crystal thermometer. When a static self-purging preservation apparatus is sealed, temperature sensor 1040 is typically disposed in contact with the cold preservation solution and in proximity to the tissue T such that a temperature of the tissue T can be ascertained during transport. Temperature display 1045 may be coupled to the temperature sensor 1040 using any suitable method, for example a wire, cable, connector, or wirelessly using available wireless protocols. In some embodiments, the temperature sensor 1040 may be attached to the adapter 26. In some embodiment, the temperature sensor 1040 is incorporated into the adapter 26 to improve the mechanical stability of the temperature sensor 1040.

In addition to the temperature sensor, systems of the invention may include one or more temperature displays. As shown in FIG. 34, the temperature display 1045 can be any display suitable for displaying a temperature measured by the temperature sensor 1040, or otherwise providing information about the temperature within the static self-purging preservation apparatus. For example, the temperature display can be a light emitting diode (LED) display or liquid crystal display (LCD) showing digits corresponding to a measured temperature. The display may alternatively comprise one or more indicator lights, for example an LED which turns on or off or flashes to indicated whether the temperature measured by the temperature sensor 1040 is within an acceptable range, e.g., 2-8° C., e.g., 4-6° C., e.g., about 4° C. The temperature sensor 1040 may also be connected to a processor (not shown) which will compare the measured temperature to a threshold or range and create an alert signal when the temperature exceeds the threshold or range. The alert may comprise an audible tone, or may signal to a networked device, e.g., a computer, cell phone, or pager that the temperature within the container exceeds the desired threshold or range.

A complete system for hypothermic transport of tissues, comprising a self-purging preservation apparatus 10 and an insulated transport container 1000 is shown in FIG. 34. The insulated transport container 1000 comprises an insulated vessel 1002 and an insulated lid 1006. The insulated vessel has at least one recess 1010 configured to hold a cooling medium 1015. As shown in FIG. 34, a sealed static self-purging preservation apparatus 100 is placed in insulated vessel 1002 along with cooling media 1015, and the insulated lid is placed on insulated vessel 1002 forming a temperature-regulated environment for transport of tissue.

The insulated vessel 1002 and the insulated lid 1006 will both comprise an insulating material that is effective in maintaining the temperature inside the insulated transport container 1000. A suitable insulating material may be any of a number of rigid polymer foams with high R values, such as polystyrene foams (e.g. STYROFOAM™), polyurethane foams, polyvinyl chloride foams, poly(acrylonitrile)(butadiene)(styrene) foams, or polyisocyanurate foams. Other materials, such as spun fiberglass, cellulose, or vermiculite could also be used. Typically, the insulating vessel 1002 will be constructed to provide a close fit for the self-purging preservation apparatus, thereby affording additional mechanical protection to the self-purging preservation apparatus and the tissues contained therein. In some embodiments, the insulated vessel 1002 and the insulated lid 1006 will be constructed of a closed-cell foam that will prevent absorption of liquids, for example water, body fluids, preservation fluid, saline, etc. In some embodiments, the insulated transport container 1000 will include a water-resistant lining (not shown) to facilitate cleaning the insulated transport container 1000 after use. In some embodiments, the lining will be removable and disposable. While not shown in FIG. 34, the insulated vessel 1002 and the insulated lid 1006 may have a hard shell on the exterior to protect the insulating material from damage or puncture. The hard shell may be formed of metal (e.g. aluminum or steel) or of a durable rigid plastic (e.g. PVC or ABS). The hard shell may have antibacterial properties through the use of antibacterial coatings or by incorporation of metal that have innate antibacterial properties (e.g. silver or copper).

While not shown in FIG. 34, the insulated vessel 1002 and the insulated lid 1006 may be connected with a hinge, hasp, clasp, or other suitable connector. The insulated vessel 1002 and the insulated lid 1006 may also close with a press-fit. The insulated transport container 1000 may include an insulating seal to make to make an air- or water-tight coupling between the insulated vessel 1002 and the insulated lid 1006. However, the insulated lid 1006 need not be sealed to the insulated vessel 1002 for the insulated transport container 1000 to maintain a suitable temperature during transport. In some embodiments, the insulated vessel 1002 and the insulated lid 1006 will be coupled with a combination lock or a tamper-evident device. The insulated vessel 1002 and/or the insulated lid 1006 may additionally comprise a handle or a hand-hold or facilitate moving the insulated transport container 1000 when loaded with a self-purging preservation apparatus 100. While not shown in FIG. 34, in some embodiments, insulated vessel 1002 will additionally have external wheels (e.g. castor wheels or in-line skate type wheels). The insulated vessel 1002 may also have a rollaboard-type retractable handle to facilitate moving the system between modes of transport or around a hospital or other medical facility.

In some embodiments, such as shown in FIG. 34, the insulated transport container 1000 will comprise a second temperature display 46 which can display a temperature measured by the temperature sensor 1040 to a user. The second temperature display 1046 may receive measurements of temperature within the static self-purging preservation apparatus 10 via a wired or a wireless connection. In the embodiment shown in FIG. 34, an electronics package on the lid assembly is coupled to the temperature display 1045 and comprises a wireless transmitter that communicates with a receiver coupled to the second temperature display 1046. This configuration avoids a user having to make a connection between the temperature sensor 1040 and the second temperature display 1046 after the self-purging preservation apparatus 10 has been placed in the insulated vessel. The insulated transport container 1000 may additionally comprise displays for additional relevant information, such as time since harvest, pressure inside the self-purging preservation apparatus 10, partial pressure of oxygen, or oxygen consumption rate of the biological sample.

Figure 35:
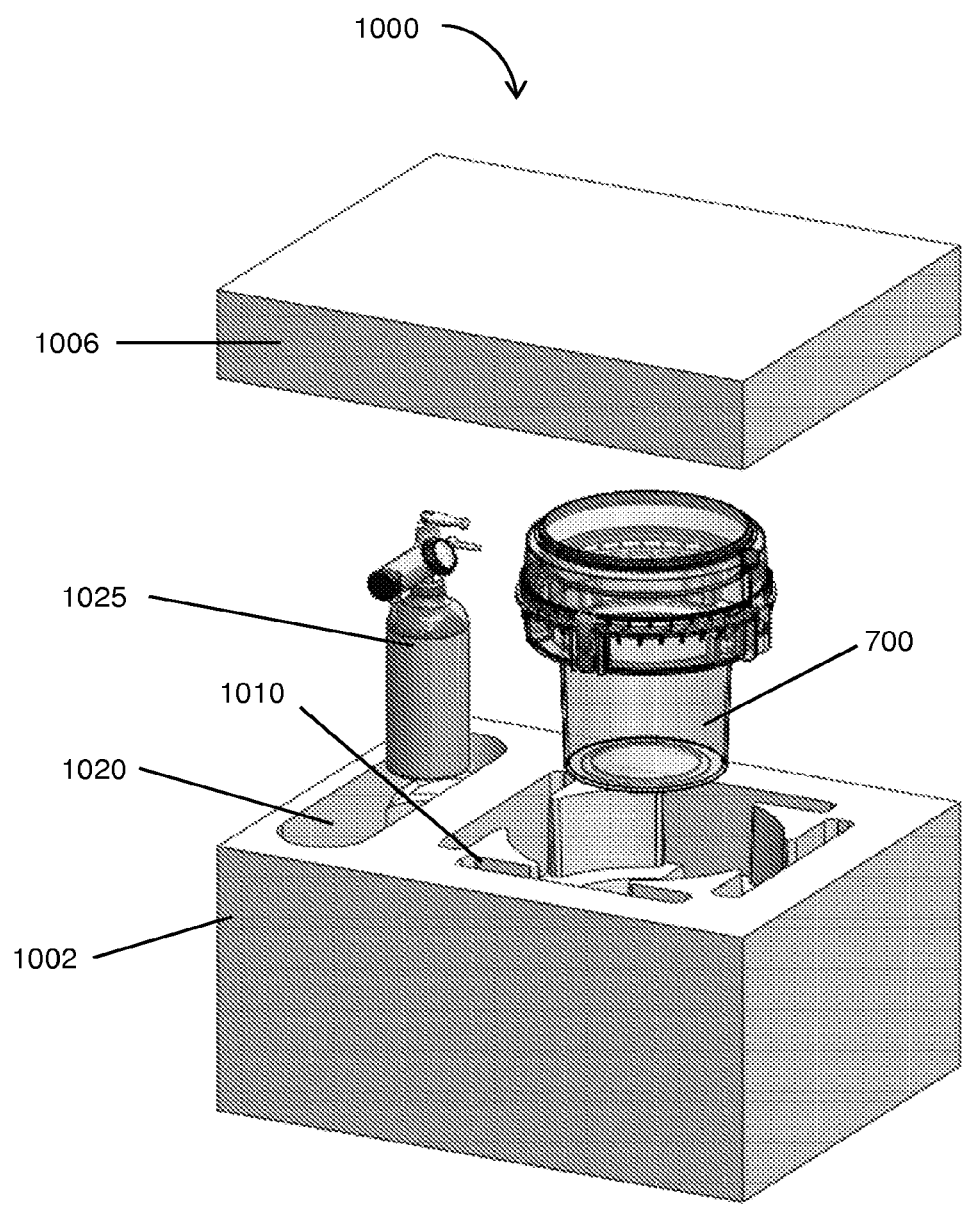
FIG. 35 shows an embodiment of a hypothermic transport system of the invention, including a self-purging preservation apparatus, an insulated transport container, and recesses for holding cooling media for maintaining the temperature of the tissue being transported. The insulated transport container is also configured to transport a source of oxygen.

The system may use any of a number of cooling media 1015 to maintain the temperature inside the insulated transport container 1000 during transport. As shown in FIG. 34, the cooling media 1015 may comprise eutectic cooling blocks, which have been engineered to have a stable temperature between 2-8° C., for example. The cooling media 1015 will be arranged in recess 1010 in the interior of the insulated vessel 1002. The recess 1010 may be a slot, such as shown in FIG. 35, or the recess may be a press-fit, or the cooling media 1015 may be coupled to the walls of the insulated vessel 1002 using a snap, screw, hook and loop, or another suitable connecter. Eutectic cooling media suitable for use with the invention is available from TCP Reliable Inc. Edison, N.J. 08837, as well as other suppliers. Other media, such as containerized water, containerized water-alcohol mixtures, or containerized water-glycol mixtures may also be used. The container need not be rigid, for example the cooling media may be contained in a bag which is placed in the recess 1010. Using the cooling media 1015, e.g. eutectic cooling blocks, the invention is capable of maintaining the temperature of the sample in the range of 2-8° C. for at least 60 minutes, e.g., for greater than 4 hours, for greater than 8 hours, for greater than 12 hours, or for greater than 16 hours.

Figure 36:
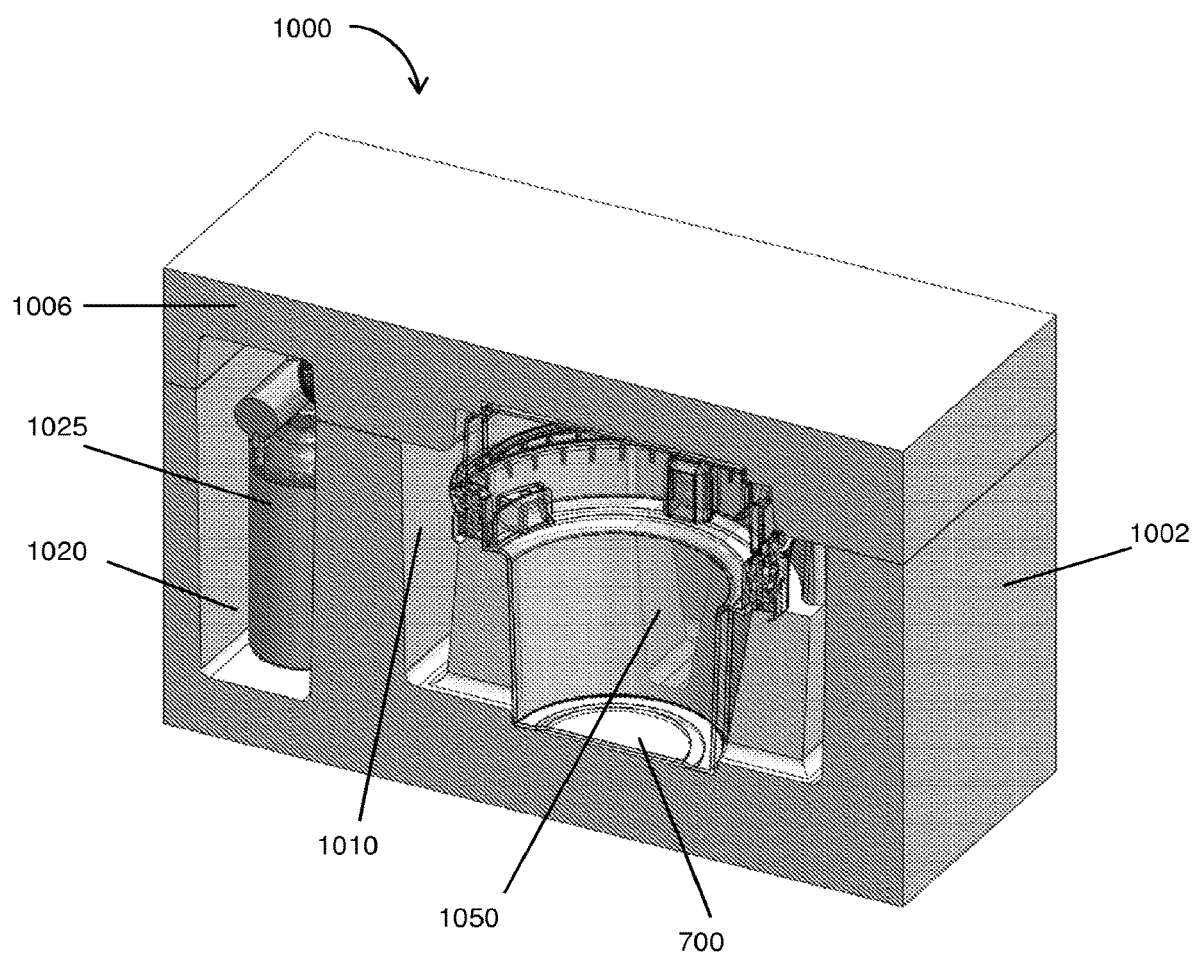
FIG. 36 shows a cut-away view of a hypothermic transport system of the invention, with detail of the interior structures that provide additional mechanical protection to the self-purging preservation apparatus and its contents.

FIG. 35 shows another embodiment of a complete system for hypothermic transport of tissues, comprising a self-purging preservation apparatus 700 and an insulated transport container 1000. As in FIG. 34, the insulated transport container comprises an insulated vessel 1002 and an insulated lid 1006. The insulated vessel has recesses 1010 for holding cooling media 1015. As shown in greater detail in FIG. 35, the insulated vessel is formed to closely fit the self-purging preservation apparatus 700 to provide mechanical protection to the container and to assure that the container remains upright during transport. The insulated vessel 1002 and the insulated lid 1006 have hard sides for durability, and may have wheels (not shown) for ease of transport. As shown in FIG. 36, the insulated vessel 1002 additionally comprises an oxygenate recess 1020 for holding a compressed oxygenate 1025, for example a cylinder of compressed oxygen. As discussed in greater detail above, the compressed oxygenate can serve a dual purpose of oxygenating the preservation solution and also providing pressure to circulate the preservation solution around or through the tissue. While not shown in FIG. 36, insulated transport container 1000 may additionally comprise a regulator and tubing to connect the compressed oxygenate to the self-purging preservation apparatus 700.

As shown in the cut-away view of the insulated transport container 1000 in FIG. 36, both the insulated vessel 1002 and the insulated lid 1006 are designed to snugly fit the self-purging preservation apparatus 700 to provide additional mechanical stability. While not visible in FIG. 36, the oxygenate recess 1020 also provides a snug fit for the compressed oxygenate, which may be, for example, a size 4 cylinder of compressed gas. Also, as shown in FIG. 36, a thermal communication passage 1050 may be provided (behind wall of self-purging preservation apparatus 700) to allow better thermal flow between the cooling media 1015 and the self-purging preservation apparatus 700. In some instances, the interstitial space between the cooling media 1015 and the self-purging preservation apparatus 700 will be filled with a thermal transport fluid, such as water or an aqueous solution. In other instances, the interstitial space will be filled with air or another gas (e.g. dry nitrogen).

The disclosed systems provide a better option for transporting biological samples than the "picnic cooler" method. In one embodiment a medical professional will provide a hypothermic transport system of the invention, for example as shown in FIGS. 34-36, suspend a biological sample in preservation fluid within a self-purging preservation apparatus, for example as shown in FIGS. 1-33, and maintain the temperature of the preservation fluid between 2 and 8° C. for at least 60 minutes. In the cases where the self-purging preservation apparatus has a temperature sensor and a temperature display, it will be possible for the medical professional to monitor the temperature of the sample after it has been sealed inside the self-purging preservation apparatus. Such temperature information will be critical in evaluating the status of the sample during transport and for identifying failures during transport. In embodiments having a second display on the insulated transport container, it will be possible to monitor the temperature of the sample without opening the insulated transport container, thereby maintaining the hypothermic environment within. Furthermore during transport, the system is capable of self-purging rising fluids, for example air, to reduce the risk that bubbles are formed in the preservation solution.

Using the systems of the invention, the preservation fluid may be maintained at a pressure greater than atmospheric pressure, and may be oxygenated, for example by an accompanying cylinder of compressed oxygen, i.e., as shown in FIG. 35. In some instances, the preservation fluid will be circulated around tissue suspended in the self-purging preservation apparatus, or the preservation fluid may be perfused through an organ suspended in the self-purging preservation apparatus. Preferably, an organ will be perfused with preservation solution by using oscillating pressures, thereby simulating the systolic and diastolic pressures experienced by circulatory system of the organ in the body. When body fluids are transported, the body fluids may be transported by suspending an additional container (e.g., a blood bag) within the self-purging preservation apparatus.

Figure 37:
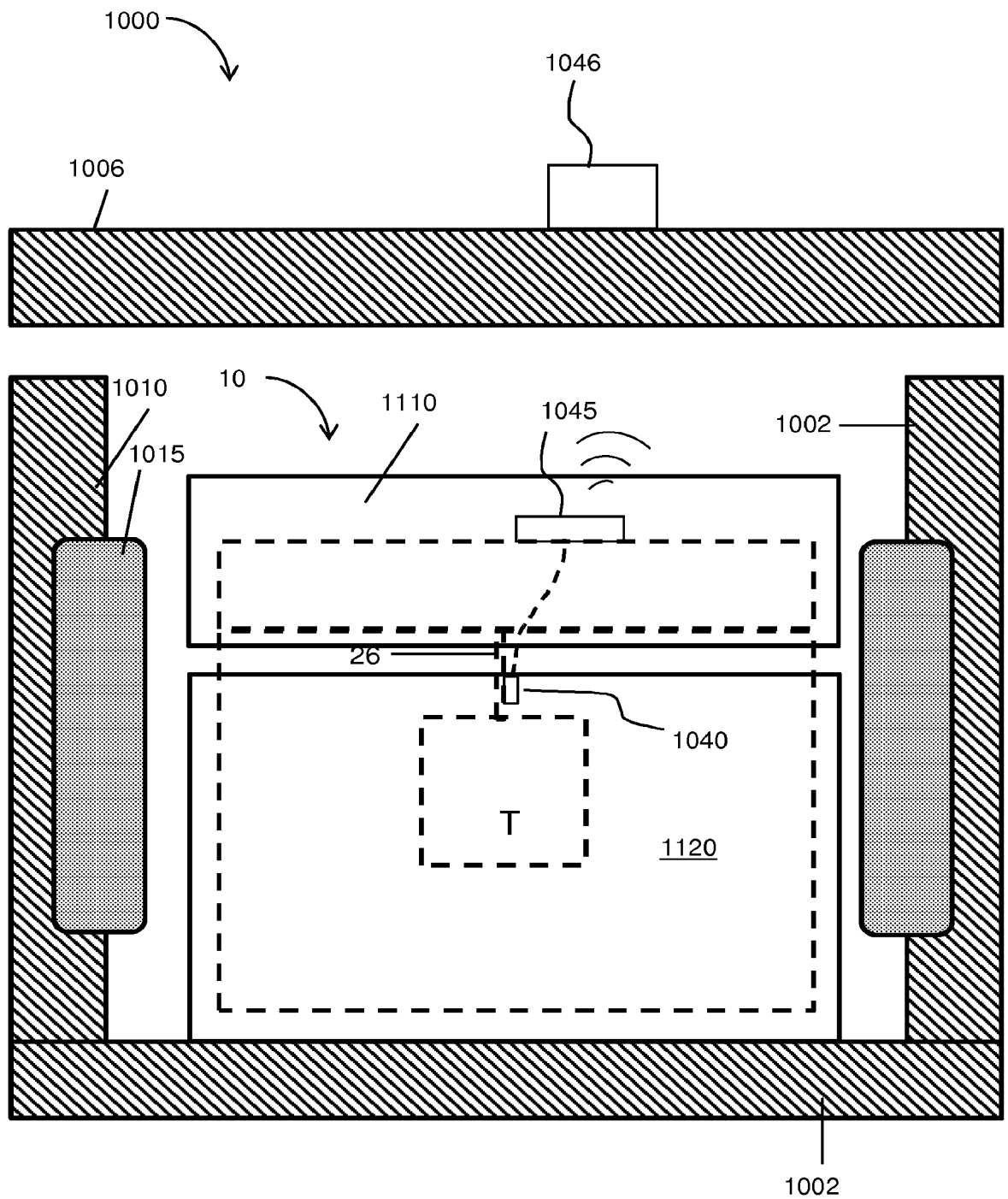
FIG. 37 shows an embodiment of a hypothermic transport system of the invention, including a self-purging preservation apparatus, a sterile canister surrounding the preservation apparatus, an insulated transport container, and cooling media for maintaining the temperature of the tissue being transported.

In another embodiment, a system of the invention may include an intermediate sterile canister 1100, including a sterile lid 1110 and a sterile bottom 1120, as shown in FIG. 37. The sterile container provides an extra layer of protection for the transported tissues and also allows the preservation apparatus 10 to stay in a sterile field during the entirety of the transport. When used, for example, for organ harvest and transport, a pre-sterilized preservation apparatus 10 and a pre-sterilized sterile canister 1100 will be brought into the sterile field of the operating room in which the harvest is conducted. The organ will be harvested, placed into the preservation apparatus 10 and the apparatus will be filled with preservation fluid as described previously. The filled preservation apparatus 10 will then be placed into the sterile canister 1100 and the sterile canister sealed, to maintain a sterile field around the preservation apparatus. A sterile tech will then hand the sterile canister, including the filled preservation container to a non-sterile tech who will place the sterile canister in the insulated transport container 1000. Once the assembled apparatus arrives at its destination, a non-sterile tech will remove the sterile container 1100 (with a non-sterile exterior) and remove the sterile lid 1100 from the sterile bottom 1120 and present the (still sterile) preservation apparatus 10 in the sterile bottom 1120 to a sterile surgical tech who will simply lift the sterile preservation apparatus 10 from the sterile bottom 1120 and take it into the sterile field, where the organ will be transplanted.

Time is of the essence during organ transport. Thus, the inclusion of sterile container 1100 can save several critical minutes that would otherwise be required to sterilize the exterior of the preservation apparatus 10 before it is moved into the sterile field. Additionally, including sterile container 1100 reduces the risk of contamination of the organ with disinfectant.

Figure 38A:
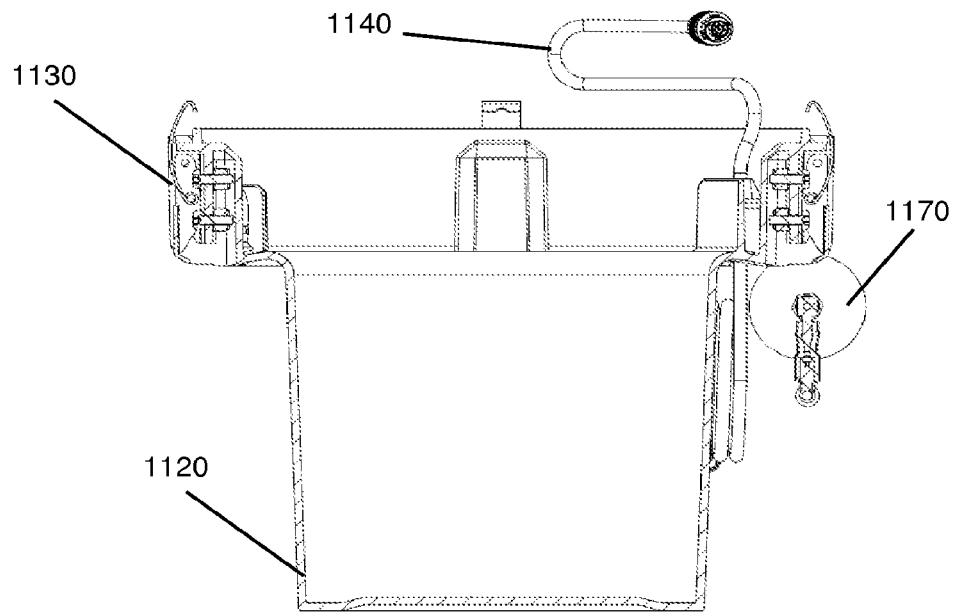
FIG. 38A is a cut-away view of an embodiment of a sterile transport canister designed to surround the preservation apparatus and maintain a sterile field during transport.
Figure 38B:
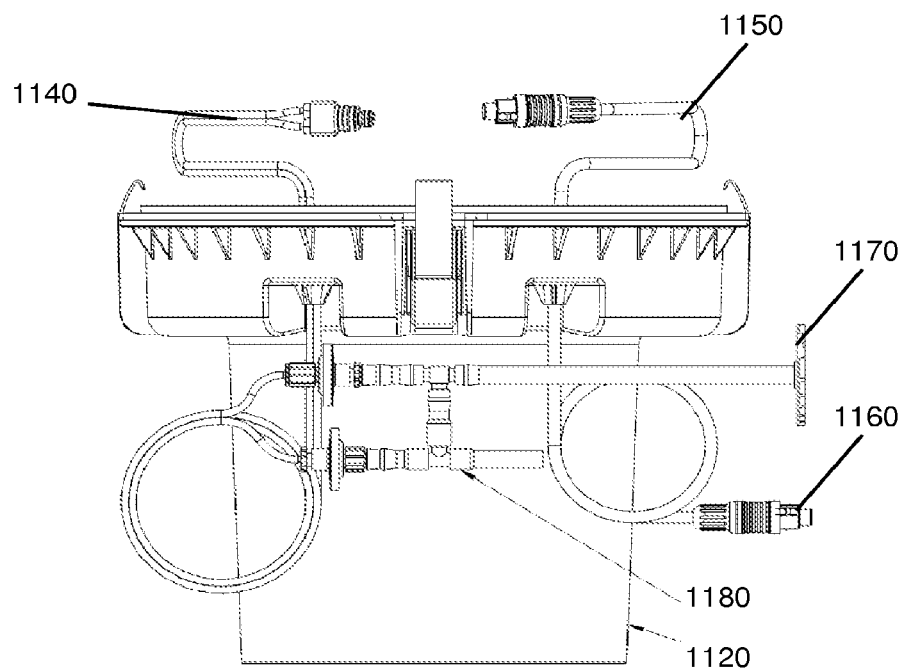
FIG. 38B is a front view of the sterile canister shown in cut-away in FIG. 38A. The sterile canister has tubes and connectors that allow the preservation apparatus to be connected to a supply of compressed gas external to the canister.

Regarding FIGS. 38 A and B, sterile container 1100 may include sterile connectors (1140 and 1150) that are connected to the preservation apparatus 10 before the sterile lid 1110 is sealed to the sterile bottom 1120 with closures 1130. The sterile connectors can be used to interface a supply of oxygen-containing gas to the pumping chamber, to provide power to the sensors and solenoid(s) in the preservation apparatus, and to receive data, such as temperature, pressure, oxygen content, etc. As shown in FIG. 38B, sterile connectors 1140 and 1150 have corresponding connections on the outside of the sterile canister 1100, thus allowing the respective connections to be interfaced with receptacles in the insulated transport container 1000 (not shown). For example, as shown in 38B, input connector 1160 provides a fluid and/or electrical and/or signal path to connector 1150 that is connected to preservation apparatus 10. In turn, connector 1140 provides an exit path for fluids (e.g., gasses and/or liquids) to leave the preservation apparatus 10. As shown in FIG. 38B, connector 1140 is coupled to branching manifold 1180 that allows less dense fluids (typically gas) to leave the device via sterile vent 1170. Branching manifold 1180 additionally includes a liquid trap that allows small amounts of liquid (e.g., preservation fluid) to be neatly trapped for disposal. However, in the event of a substantial overpressure in the preservation apparatus 10, sterile vent 1170 also provides a path for pressure relief including preservation fluid.

Figure 39:
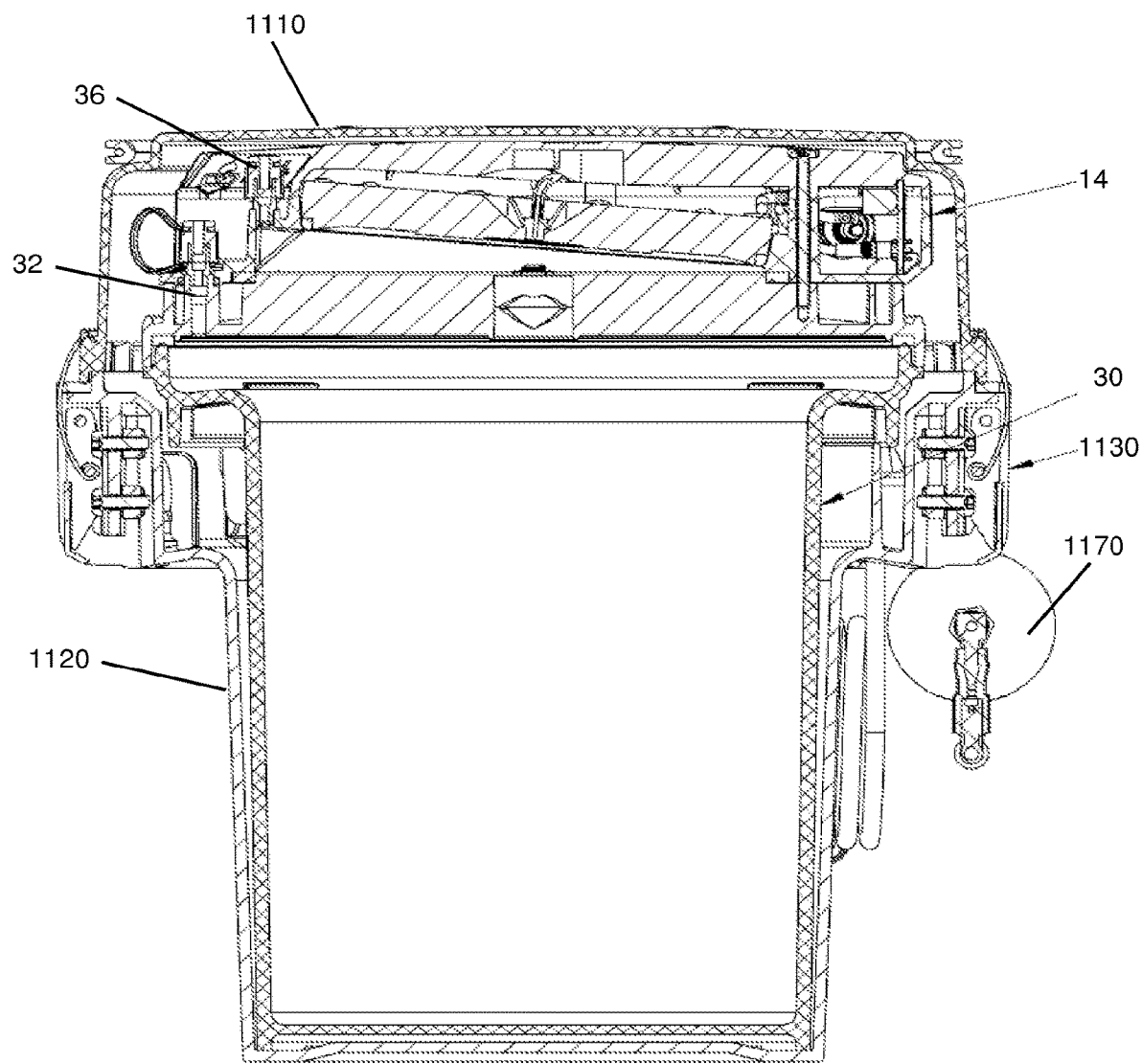
FIG. 39 is a cut-away view of an embodiment of the preservation apparatus inside the sterile canister.
Figure 40:
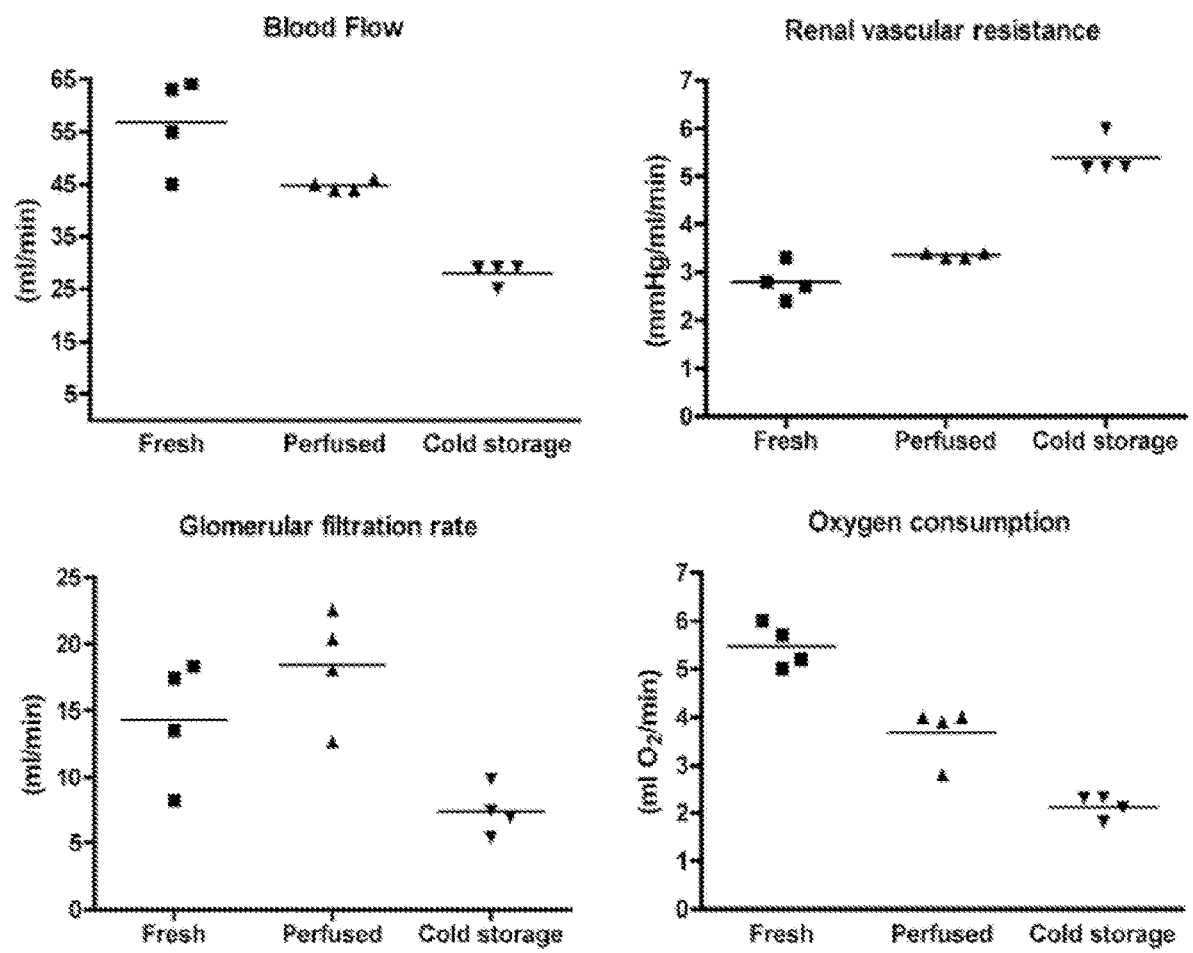
FIG. 40 shows measurements of blood flow, renal vascular resistance, glomerular filtration rate and oxygen consumption for fresh canine kidneys (■), canine kidneys hypothermicaly stored for 24 hours with perfusion (▲), and canine kidneys hypothermicly stored for 24 hours without perfusion (▼).

A detailed embodiment of preservation apparatus 10 inside sterile canister 1110 is shown in FIG. 39, and shows the optional location of the fill port 32 and the vent port 36 of the preservation lid inside the sterile lid 1110. As shown in FIG. 39, once closures 1130 are closed, sterile lid 1110 and sterile bottom 1120 maintain a sterile field around the preservation apparatus, but provide a sterile vent 1170 for release of fluids, as discussed above.

Like the perfusion apparatus, the sterile canister will typically be constructed from a sterilizable material, i.e., made of a material that can be sterilized by steam (autoclave) or with UV irradiation, or another form of sterilization. Sterilization will prevent tissues from becoming infected with viruses, bacteria, etc., during transport. In a typical embodiment the sterile canister will be delivered in a sterile condition and sealed in sterile packaging. In some embodiments, the sterile canister apparatus will be re-sterilized prior to reuse, for example at a hospital. In other embodiments, the sterile canister will be disposable.

Thus, using the system for hypothermic transport of tissues of the invention, it is possible to transport a biological sample (e.g. tissue, organs, or body fluids) over distances while maintaining a temperature of 2-8° C. Systems of the invention will enable medical professionals to keep tissues (e.g. organs) in a favorable hypothermic environment for extended periods of time, thereby allowing more time between harvest and transplant. As a result of the invention, a greater number of donor organs will be available thereby saving lives.

Although various embodiments have been described as having particular features and/or combinations of components, other embodiments are possible having any combination or sub-combination of any features and/or components from any of the embodiments described herein. The specific configurations of the various components can also be varied. For example, the size and specific shape of the various components can be different than the embodiments shown, while still providing the functions as described herein. Thus, the breadth and scope of the invention should not be limited by any of the above-described embodiments. The previous description of the embodiments is provided to enable any person skilled in the art to make or use the invention. While the invention has been particularly shown and described with reference to embodiments thereof, it will be understood by those skilled in the art that various changes in form and details may be made therein without departing from the spirit and scope of the invention.

Additional system and method of the invention are disclosed in the Examples below, which should not be viewed as limiting the invention in any way.

EXAMPLE

Example 1—Viability of Hypothermically Stored Kidneys with and without Perfusion The benefits of pulsatile cold tissue storage over static cold tissue storage were evaluated in canines. Both methods of storage were compared to freshly harvested organs.

Kidney Harvest

Adult canines weighing about 25 to 30 kg were anesthetized with 25 ml/kg of sodium pentobarbital by an intravenous injection. The subject animals were intubated and ventilated with 40% oxygen to maintain normal arterial blood oxygenation. Subject animals were then placed in a supine position and a midline incision was made in the lower abdominal cavity so that both kidneys were exposed. Following heparinization, catheters were inserted into the descending aorta above, and the inferior vena cava just below the kidneys. The aorta and inferior vena cava were crossed clamped above and below the catheters and an infusion of cold University of Wisconsin Solution (UWS) at 4° C. was initiated. Infusions continued until all blood was cleared from the organ. During infusion, cold saline, at 4° C., was poured over the kidneys and the excess removed by suction. The aorta and inferior vena cava were ligated at the cross clamp and then cut, as were the ureters. The kidneys were quickly dissected free and placed on ice for catheterization of the ureters. The ureters were catheterized with a 2 inch 18 gage catheters. The aorta was also catheterized.

Static Storage

Four canine kidneys were attached via aortic catheter to an adapter coupled to the lid of a self-purging preservation apparatus. The transport container additionally included a basket designed to support the organs. The organs were immersed into cold (4° C.) freshly prepared University of Wisconsin Solution (preservation solution). While the self-purging preservation apparatus was capable of supplying pulsatile preservation solution, it was not used. That is, the kidneys were stored statically. The self-purging preservation apparatus was then placed into an insulated transport case into which eutectic cold packs had been previously placed. Temperature was continuously monitored during 24 hours of storage. The average temperature during storage was 4.5° C.

Pulsatile Storage

Four canine kidneys were attached via aortic catheter to an adapter coupled to the lid of a self-purging preservation apparatus. The aortic catheters were attached to the adapter so that that the aorta could receive pressurized preservation solution. The transport container additionally included a basket designed to support the organs. The organs were then immersed into cold (4° C.) freshly prepared University of Wisconsin Solution (preservation solution). The self-purging preservation apparatus was pressurized with 100% $O_2$ at 2.5 to 3.0 psi and set to perfuse the kidneys at 70 pulses/min. Temperature and perfusion pressure were continuously monitored. The partial pressure of oxygen ($pO_2$) in the flowing preservation solution was measured at 15 minute intervals, both into and out of the organ. The average temperature during storage was 5.0° C.; the average perfusion pressure was 16.0 mmHg; the average preservation solution flow was 37.8 ml/min, the average $O_2$ delivery was 1.2 ml/min; the average $O_2$ consumption was 0.29 ml/min; and the average Renal Vascular Resistance (RVR; perfusion pressure×flow) was 0.43 mmHg/ml/min.

Evaluation of Kidney Viability

Following the preservation period, the kidneys were removed from the preservation device and connected to a Langendorff device to evaluate kidney function. Four additional kidneys were harvested and evaluated with the Langendorff device as a control. Each kidney were perfused with a 50:50 mixture of warm (37° C.) oxygenated (100% $O_2$) K—H solution containing inulin (15 mg/100 ml) and autologous blood. Perfusion was initiated slowly and incremented at 5 minute intervals until a mean arterial pressure of 150 mmHg was achieved. Urine, arterial and venous samples were collected from each kidney after 90 minutes in triplicate for inulin clearance and urine output measurement. Inulin was measured using the method of Waser as modified by Brown and Nolph. See Brown and Nolph, "Chemical measurements of inulin concentrations in peritoneal dialysis solution," *Clin. Chim. Acta,* 1977; 76: 103-12, incorporated herein by reference. The partial pressure of oxygen in the blood/K—H perfusate entering the renal arteries and exiting the renal veins was measured on a TruPoint Irma™ blood gas machine. Organ perfusion was measured by collecting the outflow from the renal veins during a 15 second time interval and corrected to flow/minute. Renal vascular resistance was calculated by dividing the perfusion pressure measured at the renal artery by the renal vein outflow in ml/min. Glomerular Filtration Rate (GFR) was calculated as the product of the urine inulin concentration and urine flow divided by the arterial plasma inulin concentration.

The results of the Langendorff measurements are shown graphically in FIG. 37. The temperature during function measurements on the Langendorff was 37.0±0.1° C. for all kidneys. Perfusion pressure for all kidneys was set at 150 mmHg. Renal vascular resistance (average) for freshly recovered kidneys was 2.8±0.4 mmHg/ml/min, 3.4±0.1 mmHg/ml/min for pulsatile stored kidneys, and 5.4±0.4 mmHg/ml/min for static stored kidneys. The RVR differences between the freshly recovered and pulsatile stored kidneys were not statistically significant, but the statically stored kidneys demonstrated a statistically higher RVR ($p<0.05$) (See FIG. 37).

Oxygen consumption (average) during testing by freshly recovered kidneys was 5.5±0.4 ml $O_2$/min, 3.7±0.6 ml $O_2$/min by pulsatile stored preserved kidneys, and 2.1±0.3 ml $O_2$/min by statically stored kidneys. GFR (average) was 14.3±4.6 ml/g/min for the freshly recovered kidneys, 18.4±4.3 ml/min for the pulsatile preserved organs, and 7.4±1.8 ml/min for the statically stored organs.

Looking at the results of FIG. 37, there was a statistical difference ($p<0.05$) between freshly-recovered and pulsatile stored kidneys in oxygen consumption but no statistical difference in GFR. Additionally, while blood flow and RVR were, on average, worse in the pulsatile storage kidneys as compared to the freshly recovered kidneys, the average for the pulsatile storage kidneys was within the range of the fresh kidneys. The data suggest that kidneys may be stored and/or transported for up to 24 hours using cold pulsatile storage without a substantial decrease in functionality.

In contrast, the static storage kidneys fared worse than both the fresh kidneys and the pulsatile storage kidneys in all aspects. In particular the static stored kidneys showed a significantly lower ($p<0.05$) oxygen consumption and GFR than either freshly recovered or pulsatile stored preservation groups, with a marked increase in RVR (See FIG. 37).

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

The invention claimed is:

1. A transport container comprising:
 a sample storage chamber configured to receive a biological sample;
 an adapter for coupling the biological sample inside the storage chamber;
 a lid assembly comprising a chamber, a fill port, a vent between the chamber and an exterior of the transport container, and a valve between the chamber and the sample storage chamber,
 wherein the lid assembly is removably coupleable to the sample storage chamber and, when the lid assembly is coupled to the sample storage chamber, the lid assembly is positioned at an inclined angle from a first side to a second side of the storage container and the valve and vent are positioned to direct fluids in the sample chamber to the valve, thereby allowing gases to be purged from the sample chamber through the valve to the chamber and from the chamber through the vent to the exterior of the transport container as the sample chamber is filled with fluid through the fill port, and
 wherein the fill port is separate from the adapter and provides a direct fluid path between the exterior of the transport container, through the lid assembly, to the sample storage chamber during operation.

2. The transport container of claim 1, wherein the chamber is a pumping chamber having a semi-permeable membrane disposed between the pumping chamber and the sample storage chamber at an inclined angle with respect to a horizontal axis when the transport container is placed on a horizontal surface.

3. The transport container of claim 2, wherein the semi-permeable membrane is inclined at an angle between approximately 1°-30° with respect to the horizontal axis.

4. The transport container of claim 2, wherein the valve is a ball check valve allows fluid flow from the sample storage chamber to the pumping chamber.

5. The transport container of claim 2, further comprising a source of oxygen-containing gas.

6. The transport container of claim 5, wherein the source of oxygen-containing gas is in fluid communication with a first side of the semi-permeable membrane and configured to provide a force against the semi-permeable membrane, thereby causing a second side of the semi-permeable membrane to push against a fluid in the sample storage chamber and to cause the fluid to circulate inside the transport container.

7. The transport container of claim 5, wherein the source of oxygen-containing gas is a compressed gas cylinder.

8. The transport container of claim 2, wherein the adapter couples the biological sample to the pumping chamber.

9. The transport container of claim 1, further comprising a temperature sensor, a pressure sensor, or an oxygen sensor.

10. The transport container of claim 1 further comprising a sensor configured to determine oxygen consumption rate for the biological sample.

11. The transport container of claim 1 wherein one or more of the sample storage chamber and the lid assembly is insulated.

12. The transport container of claim 2, wherein the semi-permeable membrane is planar.

13. The transport container of claim 1, wherein the fill port is proximal to a side of the storage container.

* * * * *